United States Patent
Yu et al.

(10) Patent No.: US 10,441,548 B2
(45) Date of Patent: Oct. 15, 2019

(54) AGGREGATING MICROPARTICLES FOR MEDICAL THERAPY

(71) Applicant: GRAYBUG VISION, INC., Redwood City, CA (US)

(72) Inventors: Yun Yu, Baltimore, MD (US); Joshua Kays, Baltimore, MD (US); Ming Yang, Lutherville-Timonium, MD (US); Jeffrey L. Cleland, San Carlos, CA (US)

(73) Assignee: Graybug Vision, Inc., Redwood City, CA (US)

( * ) Notice: Subject to any disclaimer, the term of this patent is extended or adjusted under 35 U.S.C. 154(b) by 0 days.

(21) Appl. No.: 15/349,985

(22) Filed: Nov. 11, 2016

(65) Prior Publication Data

US 2017/0135960 A1  May 18, 2017

Related U.S. Application Data

(60) Provisional application No. 62/276,530, filed on Jan. 8, 2016, provisional application No. 62/257,608, filed on Nov. 19, 2015, provisional application No. 62/254,707, filed on Nov. 12, 2015.

(51) Int. Cl.
| | |
|---|---|
| *A61K 9/50* | (2006.01) |
| *A61K 9/00* | (2006.01) |
| *A61P 27/02* | (2006.01) |
| *A61K 9/16* | (2006.01) |
| *A61K 47/10* | (2017.01) |
| *A61K 31/404* | (2006.01) |
| *A61K 31/382* | (2006.01) |
| *A61K 31/5377* | (2006.01) |
| *A61K 31/542* | (2006.01) |
| *A61P 27/06* | (2006.01) |
| *A61K 47/36* | (2006.01) |
| *A61K 47/26* | (2006.01) |

(52) U.S. Cl.
CPC .......... *A61K 9/5089* (2013.01); *A61K 9/0048* (2013.01); *A61K 9/1641* (2013.01); *A61K 9/1647* (2013.01); *A61K 9/5026* (2013.01); *A61K 9/5031* (2013.01); *A61K 31/382* (2013.01); *A61K 31/404* (2013.01); *A61K 31/5377* (2013.01); *A61K 31/542* (2013.01); *A61K 47/10* (2013.01); *A61P 27/02* (2018.01); *A61P 27/06* (2018.01); *A61K 9/0019* (2013.01); *A61K 47/26* (2013.01); *A61K 47/36* (2013.01)

(58) Field of Classification Search
CPC ... A61K 9/5089; A61K 9/5026; A61K 9/5031
See application file for complete search history.

(56) References Cited

U.S. PATENT DOCUMENTS

| | | |
|---|---|---|
| 4,460,563 A | 7/1984 | Calanchi |
| 4,794,000 A | 12/1988 | Ecanow |
| 4,911,920 A | 3/1990 | Jani et al. |
| 4,997,443 A | 3/1991 | Walthall et al. |
| 4,997,652 A | 3/1991 | Wong |
| 5,013,556 A | 5/1991 | Woodle et al. |
| 5,019,400 A | 5/1991 | Gombotz et al. |
| 5,286,495 A | 2/1994 | Batich et al. |
| 5,344,701 A | 9/1994 | Gagnon et al. |
| 5,441,722 A | 8/1995 | Eng et al. |
| 5,502,092 A | 3/1996 | Barrows et al. |
| 5,565,215 A | 10/1996 | Gref et al. |
| 5,612,052 A | 3/1997 | Shalaby |
| 5,624,677 A | 4/1997 | El-Rashidy et al. |
| 5,612,053 A | 5/1997 | Baichwal et al. |
| 5,855,615 A | 1/1999 | Bley et al. |
| 5,866,155 A | 2/1999 | Laurencin et al. |
| 5,869,103 A | 2/1999 | Yeh et al. |
| 5,916,586 A | 6/1999 | Desai et al. |
| 5,945,126 A | 8/1999 | Thanoo et al. |
| 6,007,845 A | 12/1999 | Domb et al. |
| 6,129,761 A | 10/2000 | Hubbell |
| 6,201,072 B1 | 3/2001 | Rathi et al. |
| 6,270,802 B1 | 8/2001 | Thanoo et al. |
| 6,287,588 B1 | 9/2001 | Shih et al. |
| 6,290,729 B1 | 9/2001 | Slepian et al. |
| 6,306,169 B1 | 10/2001 | Lee et al. |
| 6,361,798 B1 | 3/2002 | Thanoo et al. |
| 6,413,539 B1 | 7/2002 | Shalaby |
| 6,495,164 B1 | 12/2002 | Ramstack et al. |
| 6,534,084 B1 | 3/2003 | Vyakarnam et al. |
| 6,566,406 B1 | 5/2003 | Pathak et al. |
| 6,573,293 B2 | 6/2003 | Tang et al. |
| 6,589,549 B2 | 7/2003 | Shih et al. |
| 6,632,457 B1 | 11/2003 | Sawhney |

(Continued)

FOREIGN PATENT DOCUMENTS

| | | |
|---|---|---|
| CN | 101081296 A | 8/2014 |
| EP | 2403335 B1 | 8/2014 |

(Continued)

OTHER PUBLICATIONS

Sahoo, et al., Residual polyvinyl alcohol associated with poly (D,L-lactide-coglycolide) nanoparticles affects their physical properties and cellular uptake (Journal of Controlled Release 82 (2002) 105-114.*

(Continued)

*Primary Examiner* — H. Sarah Park

(74) *Attorney, Agent, or Firm* — Knowles Intellectual Property Strategies, LLC

(57) ABSTRACT

The present invention is a surface treated drug-loaded solid (e.g., non-porous) microparticle that aggregates in vivo to form a consolidated larger particle for medical therapy. In one embodiment, the particles are used for ocular therapy. Processes for producing the surface treated microparticle and injectable formulations which include the surface treated microparticle are also provided. When used in the eye, long-term consistent intraocular delivery can be achieved without disrupting vision and minimizing undesirable inflammatory responses.

78 Claims, 15 Drawing Sheets

(56) References Cited

U.S. PATENT DOCUMENTS

| | | | |
|---|---|---|---|
| 6,703,047 B2 | 3/2004 | Sawheny et al. |
| 6,706,289 B2 | 3/2004 | Lewis et al. |
| 6,818,018 B1 | 11/2004 | Sawhney |
| 6,841,617 B2 | 1/2005 | Jeong et al. |
| 7,211,275 B2 | 5/2007 | Ying et al. |
| 7,501,179 B2 | 3/2009 | Song et al. |
| 7,585,075 B2 | 8/2009 | Marmo |
| 7,828,844 B2 | 11/2010 | Marmo et al. |
| 7,883,520 B2 | 2/2011 | Gaeckle et al. |
| 7,998,108 B2 | 8/2011 | Nazzaro et al. |
| 8,167,941 B2 | 5/2012 | Boyd et al. |
| 8,192,408 B2 | 6/2012 | Nazzaro et al. |
| 8,252,307 B2 | 8/2012 | Ashton |
| 8,268,342 B2 * | 9/2012 | Panda .................... A61L 15/40 |
| | | | 424/426 |
| 8,277,830 B2 | 10/2012 | de Jean, Jr. et al. |
| 8,298,578 B2 | 10/2012 | de Jean, Jr. et al. |
| 8,399,006 B2 | 3/2013 | de Jean, Jr. et al. |
| 8,409,606 B2 | 4/2013 | Sawhney et al. |
| 8,409,607 B2 | 4/2013 | Hughes et al. |
| 8,414,646 B2 | 4/2013 | de Jean, Jr. et al. |
| 8,492,334 B2 | 7/2013 | Lavik et al. |
| 8,574,613 B2 | 11/2013 | Guo et al. |
| 8,574,659 B2 | 11/2013 | Guo et al. |
| 8,623,395 B2 | 1/2014 | de Jean, Jr. et al. |
| 8,628,801 B2 | 1/2014 | Garreta et al. |
| 8,632,809 B2 | 1/2014 | Asgharian et al. |
| 8,663,674 B2 | 3/2014 | Wen et al. |
| 8,685,435 B2 | 4/2014 | Nivaggioli et al. |
| 8,715,346 B2 | 5/2014 | de Jean, Jr. et al. |
| 8,795,712 B2 | 8/2014 | de Jean, Jr. et al. |
| 8,808,727 B2 | 8/2014 | de Jean, Jr. et al. |
| 8,815,284 B2 | 8/2014 | Guo et al. |
| 8,871,241 B2 | 10/2014 | Chou et al. |
| 8,889,193 B2 | 11/2014 | McDonnell et al. |
| 8,905,963 B2 | 12/2014 | de Jean, Jr. et al. |
| 8,939,948 B2 | 1/2015 | de Jean, Jr. et al. |
| 8,957,034 B2 | 2/2015 | Hanes et al. |
| 8,962,577 B2 | 2/2015 | Hanes et al. |
| 8,993,615 B2 | 3/2015 | Zack et al. |
| 9,023,896 B2 | 5/2015 | Ashton et al. |
| 9,033,911 B2 | 5/2015 | de Jean, Jr. et al. |
| 9,044,319 B2 | 6/2015 | Matheny |
| 9,050,765 B2 | 6/2015 | Boyd et al. |
| 9,056,057 B2 | 6/2015 | Popov et al. |
| 9,066,779 B2 | 6/2015 | de Jean, Jr. et al. |
| 9,095,506 B2 | 8/2015 | Spanda et al. |
| 9,107,748 B2 | 8/2015 | de Jean, Jr. et al. |
| 9,114,070 B2 | 8/2015 | Hara et al. |
| 9,125,735 B2 | 9/2015 | de Jean, Jr. et al. |
| 9,125,807 B2 | 9/2015 | Sawhney et al. |
| 9,161,903 B2 | 10/2015 | Drapeau et al. |
| 9,161,938 B2 | 10/2015 | Huang et al. |
| 9,162,981 B2 | 10/2015 | Zack et al. |
| 9,205,150 B2 | 12/2015 | Jarrett et al. |
| 9,222,060 B2 | 12/2015 | Barbe et al. |
| 9,327,037 B2 | 5/2016 | Suk et al. |
| 9,382,229 B2 | 7/2016 | Zack et al. |
| 9,415,020 B2 | 8/2016 | Ensign et al. |
| 9,533,068 B2 | 1/2017 | Kashiwabuchi et al. |
| 9,669,136 B2 | 6/2017 | Friedman et al. |
| 9,775,906 B2 | 10/2017 | Sawhney et al. |
| 2002/0183858 A1 | 12/2002 | Contiliano et al. |
| 2004/0175429 A1 | 9/2004 | Alavattam |
| 2004/0209807 A1 | 10/2004 | Quay et al. |
| 2004/0234611 A1 | 11/2004 | Ahlheim et al. |
| 2004/0258763 A1 | 12/2004 | Bell |
| 2005/0042294 A1 | 2/2005 | Thanoo et al. |
| 2005/0048123 A1 | 3/2005 | Su et al. |
| 2005/0101676 A1 | 5/2005 | Fahl et al. |
| 2005/0249773 A1 | 10/2005 | Maspero et al. |
| 2006/0083781 A1 | 4/2006 | Shastri et al. |
| 2006/0246145 A1 | 11/2006 | Chang et al. |
| 2006/0263335 A1 | 11/2006 | France et al. |
| 2007/0149593 A1 | 6/2007 | Ghosh et al. |
| 2007/0231360 A1 | 10/2007 | Peyman |
| 2008/0166411 A1 | 6/2008 | Shah et al. |
| 2008/0187568 A1 | 8/2008 | Sawhney et al. |
| 2008/0241248 A1 | 10/2008 | France et al. |
| 2008/0305172 A1 | 12/2008 | Ahlheim et al. |
| 2009/0203709 A1 | 8/2009 | Steinberg et al. |
| 2010/0063135 A1 | 3/2010 | Dande et al. |
| 2010/0063175 A1 | 3/2010 | Ginty et al. |
| 2010/0074957 A1 | 3/2010 | Robinson et al. |
| 2010/0124565 A1 | 5/2010 | Spada et al. |
| 2010/0143479 A1 | 7/2010 | Thanoo et al. |
| 2010/0227865 A1 | 9/2010 | Riggs-Sauthier et al. |
| 2010/0247669 A1 | 9/2010 | Eliasof et al. |
| 2011/0123446 A1 | 5/2011 | DeSimone et al. |
| 2011/0142936 A1 | 6/2011 | Campbell et al. |
| 2012/0052041 A1 | 3/2012 | Basu et al. |
| 2012/0063997 A1 | 3/2012 | Hunter et al. |
| 2012/0071865 A1 | 3/2012 | Jarrett et al. |
| 2012/0269894 A1 | 10/2012 | Ahlheim et al. |
| 2013/0071349 A1 | 3/2013 | Robinston et al. |
| 2013/0071462 A1 | 3/2013 | Jarrett et al. |
| 2013/0122064 A1 | 5/2013 | Ahlheim et al. |
| 2013/0183244 A1 | 7/2013 | Hanes et al. |
| 2013/0272994 A1 | 10/2013 | Fu et al. |
| 2013/0316001 A1 | 11/2013 | Popov et al. |
| 2013/0316006 A1 | 11/2013 | Popov et al. |
| 2014/0107025 A1 | 4/2014 | Wirostko |
| 2014/0178475 A1 | 6/2014 | Figueiredo et al. |
| 2014/0248358 A1 | 9/2014 | Figueiredo et al. |
| 2014/0249158 A1 | 9/2014 | Figueiredo et al. |
| 2014/0276482 A1 | 9/2014 | Astafieva et al. |
| 2014/0294986 A1 | 10/2014 | Liu et al. |
| 2014/0323407 A1 | 10/2014 | Francois et al. |
| 2014/0329913 A1 | 11/2014 | Hanes et al. |
| 2015/0086484 A1 | 3/2015 | Hanes et al. |
| 2015/0099805 A1 | 4/2015 | Hughes |
| 2015/0140106 A1 | 5/2015 | Mousa |
| 2015/0147406 A1 | 5/2015 | Robinson et al. |
| 2015/0157562 A1 | 6/2015 | Hughes |
| 2016/0038407 A1 | 2/2016 | Drapeau et al. |
| 2016/0106587 A1 | 4/2016 | Jarrett et al. |
| 2016/0166504 A1 | 6/2016 | Jarrett et al. |
| 2016/0310417 A1 | 10/2016 | Prausnitz et al. |
| 2016/0317438 A1 | 11/2016 | Ashton |
| 2016/0324836 A1 | 11/2016 | Ashton |
| 2016/0331738 A1 | 11/2016 | Jarrett et al. |
| 2017/0020729 A1 | 1/2017 | Jarrett et al. |
| 2017/0080092 A1 | 3/2017 | Cleland et al. |
| 2017/0143636 A1 | 5/2017 | Jarett et al. |
| 2018/0333282 A1 | 11/2018 | Sawhney et al. |

FOREIGN PATENT DOCUMENTS

| | | | | |
|---|---|---|---|---|
| EP | 3006050 B1 | 2/2018 | | |
| GB | 929401 | 6/1963 | | |
| GB | 929406 | 6/1963 | | |
| JP | 2016-132616 A | 7/2016 | | |
| KR | 2015-0117745 A | 10/2015 | | |
| WO | WO 1996/20698 A2 | 7/1996 | | |
| WO | WO-9620698 A2 * | 7/1996 | ........... | A61K 9/5153 |
| WO | WO 1999/01498 A1 | 1/1999 | | |
| WO | WO 1999/25391 A2 | 5/1999 | | |
| WO | WO 2000/64953 A1 | 11/2000 | | |
| WO | WO 2000/64977 A1 | 11/2000 | | |
| WO | WO 2001/40767 A1 | 6/2001 | | |
| WO | WO 2002/38127 A2 | 5/2002 | | |
| WO | WO 2002/053189 A2 | 7/2002 | | |
| WO | WO 2003/000237 A2 | 1/2003 | | |
| WO | WO 2004/084968 A1 | 10/2004 | | |
| WO | WO 2005/112884 A1 | 12/2005 | | |
| WO | WO 2006/044660 A2 | 4/2006 | | |
| WO | WO 2006/116107 A2 | 11/2006 | | |
| WO | WO 2007/065933 A1 | 6/2007 | | |
| WO | WO 2007/068489 A1 | 6/2007 | | |
| WO | WO 2008/030557 A2 | 3/2008 | | |
| WO | WO 2008/041001 A1 | 4/2008 | | |
| WO | WO 2008/093094 A2 | 8/2008 | | |
| WO | WO 2008/093095 A2 | 8/2008 | | |
| WO | WO 2009/089070 A2 | 7/2009 | | |

(56) References Cited

FOREIGN PATENT DOCUMENTS

| | | |
|---|---|---|
| WO | WO 2010/100506 A2 | 9/2010 |
| WO | WO 2012/054923 A2 | 4/2012 |
| WO | WO 2012/061703 A1 | 5/2012 |
| WO | WO 2013/112434 A1 | 8/2013 |
| WO | WO 2013/166385 A1 | 11/2013 |
| WO | WO 2013/177367 A2 | 11/2013 |
| WO | WO 2013/188283 A1 | 12/2013 |
| WO | WO 2015/077300 A1 | 5/2015 |
| WO | WO 2015/172149 A1 | 11/2015 |
| WO | WO 2016/025215 A1 | 2/2016 |
| WO | WO 2016/100380 A1 | 6/2016 |
| WO | WO 2016/100392 A1 | 6/2016 |
| WO | WO 2016/118506 A1 | 7/2016 |

OTHER PUBLICATIONS

Ayalasomayajula, S.P. and Kompella, U.B., "Subconjunctivally administered celecoxib-PLGA microparticles sustain retinal drug levels and alleviate diabetes-induced oxidative stress in a rat model", *Eur. J. Pharm.*, 511, 191-198 (2005).
Baiardo et al. "Thermal and Mechanical Properties of Plasticized Poly(L-lactic acid)" Journal of Applied Polymer Science, 90, 1731-1738 (2003).
Bible et al. "Attachment of stem cells to scaffold particles for intra-cerebral transplantation", *Nat. Protoc.*, 10, 1440-1453, (2009).
Cattel et al. "From conventional to stealth liposomes a new frontier in cancer chemotherapy," Tumori, 83(3):237-249 (2003).
Garbuzenko et al. "Effect of grafted PEG on liposome size on compressibility and packing of lipid bilayer," Chem Phys Lipids, 135:117-129 (2005).
Hedberg, et al. "Controlled release of an osteogenic peptide from injectable biodegradable polymeric composites" Journal of Controlled Release, 84, 137-150 (2002).
Hou, et al. "In Situ Gelling Hydrogels Incorporating Microparticles as Drug Delivery Carriers for Regenerative Medicine" Journal of Pharmaceutical Sciences, 97, 3972-3980 (2008).
Hutmacher D.W. "Scaffolds in tissue engineering bone and cartilage." Biomaterials, 21, 2529-2543 (2000).
Immordino et al. "Stealth liposomes: review of the basic science, rationale, and clinical applications, existing and potential," Int J Nanomed., 1(3):297-315 (2006).
International Search Report and Written Opinion for International Application No. PCT/US2016/061706; International Filing Date: Nov. 11, 2016; dated Mar. 16, 2017; 12 pages.
Jacobs et al. Polymer Delivery Systems Concepts in Polymeric Delivery Systems; El-Nokaly, M., et al.; ACS Symposium Series; American Chemical Society: Washington, DC, 1993.
Kempen, et al. Controlled drug release from a novel injectable biodegradable microsphere/scaffold composite based on poly(propylene fumarate).
Kim et al. "Biodegradable polymeric microspheres with "open/closed" pores for sustained release of human growth hormone" *J. of Controlled Release*, 112, 167-174, (2006).
Lai et al. "Rapid transport of large polymeric nanoparticles in fresh undiluted human mucas" PNAS, 104, 1482-1487 (2007).
Peeters, et al. "Can ultrasound solve the transport barrier of the neural retina," Pharma Res., 25(11):2657-65 (2008).
Qutachi et al. "Injectable and porous PLGA microspheres that form highly porous scaffolds at body temperature", *Acta Biomaterialia*, 10, 5080-5098, (2014).
Rahman et al. "PLGA/PEG-hydrogel composite scaffolds with controllable mechanical properties" *J. of Biomedical Materials Research*, 101, 648-655, (2013).
Sawhney et al. "Bioerodible Hydrogels Based on Photopolymerized Poly(ethyleneglycol)-co-poly(α-hydroxy acid) Diacrylate Macromers" Macromolecules, 26, 581-587 (1993).
Takahashi, H. et al. "A Novel Vascular Endothelial Growth Factor Receptor 2 Inhibitor, SU11248, Suppresses Choroidal Neovascularization In Vitro" Journal of Ocular Pharmacology and Therapeutics, 22, 213-219, (2006).

van de Ven et al. "Rapid tumoritropic accumulation of systemically injected plateloid particles and their biodistribution" J Control Release, 158(1), 148-55 (2012).
Yang et al. "The Design of Scaffolds for Use in Tissue Engineering. Part I. Traditional Factors" Tissue Engineering, 7, 679-689 (2001).
Anderson et al. "Biodegradation and biocompatibility of PLA and PLGA microspheres" Advanced Drug Delivery Reviews, 28, 5-24 (1997).
Fuchs et al. "Sunitinib-eluting beads for chemoembolization: methods for in vitro evaluation of drug release" International Journal of Pharmaceutics 482, 68-74 (2015).
Herrero-Vanrell et al. "The potential of using biodegradable microspheres in retinal diseases and othe rintraocular pathologies" Progress in Retinal and Eye Research 42, 27-43 (2014).
Li et al. "Microencapsulation by solvent evaporation: state of the art for process engineering approaches" International Journal of Pharmaceutics 363, 26-39 (2008).
Makadia et al. "Poly Lactic-co-Glycolic Acid (PLGA) as Biodegradable Controlled Drug Delivery Carrier" Polymers (Basel). 3, 1377-1397 (2011).
Ramazani et al. "Sunitinib microspheres based on [PDLLA-PEG-PDLLA]-b-PLLA multi-block copolymers for ocular delivery" European Journal of Pharmaceutics and Biopharmaceutics 95, 368-377 (2015).
Ungaro et al. "Microsphere-integrated collagen scaffolds for tissue engineering: effect of microspheres formulation and scaffold properties on protein release kinetics" J Control Release, 113(2):128-136 (2006).
Wang et al. "Combination of hyaluronic acid hydrogel scaffold and PLGA microspheres for supporting survival of neural stem cells." Pharm Res. 28(6): 1406-1414 (2011).
Welsbie et al. "Functional genomic screening identified dual leucine zipper kinase as a key mediator of retinal ganglion cell death" PNAS, 110(10):4045-4050 (2013).
Zhao, Z "Preparation and characterization of sunitinib-loaded microspheres for arterial embolization" Journal of Chinese Pharmaceutical Sciences 23, 558-564 (2014).
Amparo F. et al. "Safety and efficacy of the multitargeted receptor kinase inhibitor pazopanib in the treatment of corneal neovascularization" Invest Ophthalmol Vis Sci. 2013; 54(1), 537-44.
Benny, O. "Local Delivery of Poly Lactic-co-glycolic Acid Microspheres Containing Imatinib Mesylate Inhibits Intracranial Xenograft Glioma Growth" Clin Cancer Res 2009; 15(4), 1222-1231.
Gaudana, R. et al. "Recent Perspectives in Ocular Drug Delivery" Pharm Res. 2009; 26(5), 1197-1216.
Jeyanthi et al. "Effect of solvent removal technique on the matrix characteristics of polylactide/glycolide microspheres for peptide delivery" Journal of Controlled Release 1996; 38, 235-244.
Kirby, G. et al. "PLGA-Based Microparticles for the Sustained Release of BMP-2" Polymers 2011; 3(1), 571-586.
Luan X et al. "Key parameters affecting the initial release (burst) and encapsulation efficiency of peptide-containing poly(lactide-co-glycolide) microparticles," International Journal of Pharmaceutics, 2006; 324(2), 168-175.
Yang et al. "Effect of preparation conditions on morphology and release profiles of biodegradable polymeric microspheres containing protein fabricated by double-emulsion method" Chemical Engineering Science 2000; 55, 2223-2236.
Wagh et al. "Polymers used in ocular dosage form and drug delivery systems" Asian Journal of Pharmaceutics, 2008, 2(1), 12-17.
Bundgaard, H. et al. "N-Sulfonyl Imidates as a Novel Prodrug Form for an Ester Function or a Sulfonamide Group" *J. Med. Chem*, 1988, 31, 2066-2069.
US, 2018-0326078, A1, U.S. Appl. No. 15/976,847, Graybug Vision, Inc., Nov. 15, 2018.
Prajapati et al. "Current Knowledge on biodegradable micropspheres in drug delivery" Expert Opinion on Drug Delivery 2015, 12:8, 1283.

* cited by examiner

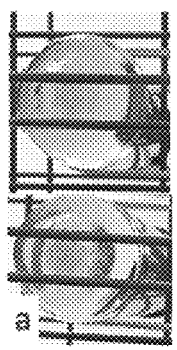 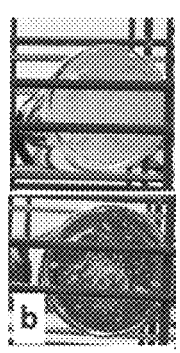  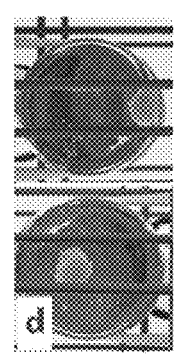
FIG. 8A  FIG. 8B  FIG. 8C  FIG. 8D
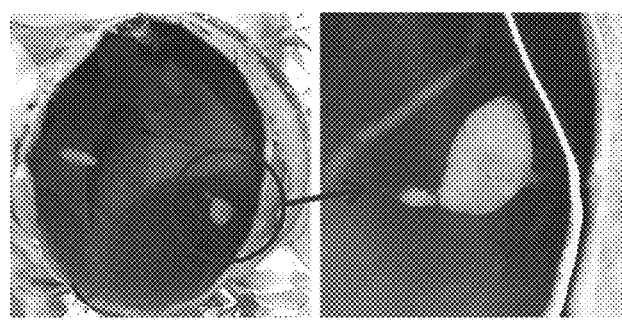
FIG. 9

AGGREGATING MICROPARTICLES FOR MEDICAL THERAPY

CROSS-REFERENCE TO RELATED APPLICATIONS

This application claims the benefit of priority to U.S. Application No. 62/254,707 filed Nov. 12, 2015, U.S. Application No. 62/257,608 filed Nov. 19, 2015, and U.S. Application No. 62/276,530 filed Jan. 8, 2016, which are incorporated by reference herein for all purposes.

FIELD OF THE INVENTION

The present invention is a surface treated drug-loaded solid (e.g., non-porous) microparticle that aggregates in vivo to form a consolidated larger particle for medical therapy. In one embodiment, the particles are used for ocular therapy. Processes for producing the surface treated microparticle and injectable formulations, including the surface treated microparticle, are also provided. When used in the eye, long-term consistent intraocular delivery can be achieved that minimizes disruption of vision and minimizes undesirable inflammatory responses.

BACKGROUND

The structure of the eye can be divided into two segments: the anterior and posterior. The anterior segment comprises the front third of the eye and includes the structures in front of the vitreous humor: the cornea, iris, ciliary body, and lens. The posterior segment includes the back two-thirds of the eye and includes the sclera, choroid, retinal pigment epithelium, neural retina, optic nerve, and vitreous humor.

Important diseases affecting the anterior segment of the eye include glaucoma, allergic conjunctivitis, anterior uveitis, and cataracts. Diseases affecting the posterior segment of the eye include dry and wet age-related macular degeneration (AMD), cytomegalovirus (CMV) infection, diabetic retinopathy, choroidal neovascularization, acute macular neuroretinopathy, macular edema (such as cystoid macular edema and diabetic macular edema), Behcet's disease, retinal disorders, diabetic retinopathy (including proliferative diabetic retinopathy), retinal arterial occlusive disease, central retinal vein occlusion, uveitic retinal disease, retinal detachment, ocular trauma, damage caused by ocular laser treatment or photodynamic therapy, photocoagulation, radiation retinopathy, epiretinal membrane disorders, branch retinal vein occlusion, anterior ischemic optic neuropathy, non-retinopathy diabetic retinal dysfunction and retinitis pigmentosa. Glaucoma is sometimes also considered a posterior ocular condition because a therapeutic goal of glaucoma treatment is to prevent or reduce the loss of vision due to damage or loss of retinal cells or optic nerve cells.

Typical routes of drug administration to the eye include topical, systemic, intravitreal, intraocular, intracameral, subconjunctival, subtenon, retrobulbar, and posterior juxtascleral. (Gaudana, R., et al., "Ocular Drug Delivery", *The American Association of Pharmaceutical Scientist Journal*, 12(3)348-360, 2010).

A number of types of delivery systems have been developed to deliver therapeutic agents to the eye. Such delivery systems include conventional (solution, suspension, emulsion, ointment, inserts, and gels), vesicular (liposomes, niosomes, discomes, and pharmacosomes), advanced materials (scleral plugs, gene delivery, siRNA, and stem cells), and controlled-release systems (implants, hydrogels, dendrimers, iontophoresis, collagen shields, polymeric solutions, therapeutic contact lenses, cyclodextrin carriers, microneedles, microemulsions, and particulates (microparticles and nanoparticles)).

Treatment of posterior segment diseases remains a daunting challenge for formulation scientists. Drug delivery to the posterior segment of the eye is typically achieved via an intravitreal injection, the periocular route, implant, or by systemic administration. Drug delivery to the posterior segment by way of the periocular route can involve the application of a drug solution to the close proximity of the sclera, which results in high retinal and vitreal concentrations.

Intravitreal injection is often carried out with a 30 gauge or less needle. While intravitreal injections offer high concentrations of drug to the vitreous chamber and retina, they can be associated with various short term complications such as retinal detachment, endophthalmitis and intravitreal hemorrhages. Experience shows that injection of small particles can lead to the rapid dispersal of the particles which can obstruct vision (experienced by the patient as "floaties" or "floaters") and the rapid removal of the particles from the injection site (which can occur via the lymphatic drainage system or by phagocytosis). In addition, immunogenicity can occur upon recognition of the microspheres by macrophages and other cells and mediators of the immune system.

Complications in periocular injections include rises in intraocular pressure, cataract, hyphema, strabismus, and corneal decompensation. Transscleral delivery with periocular administration is seen as an alternative to intravitreal injections. However, ocular barriers such as the sclera, choroid, retinal pigment epithelium, lymphatic flow, and general blood flow can compromise efficacy. Systemic administration, which is not advantageous given the ratio of the volume of the eye to the entire body, can lead to potential systemic toxicity.

A number of companies have developed microparticles for treatment of eye disorders. For example, Allergan has disclosed a biodegradable microsphere to deliver a therapeutic agent that is formulated in a high viscosity carrier suitable for intraocular injection or to treat a non-ocular disorder (U.S. publication 2010/0074957 and U.S. publication 2015/0147406 claiming priority to a series of applications back to Dec. 16, 2003). In one embodiment, the '957 application describes a biocompatible, intraocular drug delivery system that includes a plurality of biodegradable microspheres, a therapeutic agent, and a viscous carrier, wherein the carrier has a viscosity of at least about 10 cps at a shear rate of 0.1/second at 25° C.

Allergan has also disclosed a composite drug delivery material that can be injected into the eye of a patient that includes a plurality of microparticles dispersed in a media, wherein the microparticles contain a drug and a biodegradable or bioerodible coating and the media includes the drug dispersed in a depot-forming material, wherein the media composition may gel or solidify on injection into the eye (WO 2013/112434 A1, claiming priority to Jan. 23, 2012). Allergan states that this invention can be used to provide a depot means to implant a solid sustained drug delivery system into the eye without an incision. In general, the depot on injection transforms to a material that has a viscosity that may be difficult or impossible to administer by injection.

In addition, Allergan has disclosed biodegradable microspheres between 40 and 200 μm in diameter, with a mean diameter between 60 and 150 μm that are effectively retained in the anterior chamber of the eye without producing hyperemia (US 2014/0294986). The microspheres contain a drug effective for an ocular condition with greater than seven day release following administration to the anterior chamber of the eye. The administration of these large particles is intended to overcome the disadvantages of injecting 1-30 µm particles which are generally poorly tolerated.

Regentec Limited has filed a series of patent applications on the preparation of porous particles that can be used as tissue scaffolding (WO 2004/084968 and U.S. publication 2006/0263335 (filed Mar. 27, 2003) and U.S. publication 2008/0241248 (filed Sep. 20, 2005) and WO 2008/041001 (filed Oct. 7, 2006)). The porosity of the particles must be sufficient to receive cells to be held in the particle. The cells can be added to the matrix at, or prior to, implantation of the matrix or afterward in the case of recruitment from endogenous cells in situ. Regentec also published an article on tissue scaffolding with porous particles (Qutachi et al. "Injectable and porous PLGA microspheres that form highly porous scaffolds at body temperature", *Acta Biomaterialia*, 10, 5080-5098, (2014)).

In addition, Regentec Limited also filed patent applications on the preparation of large porous particles that can be used in drug delivery (WO 2010/100506 and U.S. publication 2012/0063997 (filed Mar. 5, 2009)). The porosity of the particles allows for quick delivery of the therapeutic agent. The particles are intended to form a scaffold that fills the space in which they are injected by a trigger such as a change in temperature.

Additional references pertaining to highly porous microparticles include publications by Rahman and Kim. Rahman et al. "PLGA/PEG-hydrogel composite scaffolds with controllable mechanical properties" *J. of Biomedical Materials Research*, 101, 648-655, (2013) describes hydrogels of approximately 50 percent porosity and their corresponding mechanical properties. Kim et al. "Biodegradable polymeric microspheres with "open/closed" pores for sustained release of human growth hormone" *J. of Controlled Release*, 112, 167-174, (2006) describes PLGA polymers with pores for the delivery of human growth hormone.

EP 2125048 filed by Locate Therapeutics Limited (filed Feb. 1, 2007) as well as WO 2008/093094, U.S. publication 2010/0063175 (filed Feb. 1, 2007), and WO 2008/093095 (filed Feb. 1, 2007) filed by Regentec Limited disclose the preparation of particles that are not necessarily porous but that when exposed to a trigger (such as temperature) form a tissue scaffold useful in the repair of damaged or missing tissue in a host.

U.S. Pat. No. 9,161,903 issued on Oct. 20, 2015 to Warsaw Orthopedic and U.S. publication 2016/0038407 filed by Warsaw Orthopedic Inc. disclose a flowable composition for injection at a target tissue site beneath the skin that includes a flowable composition that hardens at or near the target tissue site.

Bible et al. "Attachment of stem cells to scaffold particles for intra-cerebral transplantation", *Nat. Protoc.*, 10, 1440-1453, (2009) describes a detailed process to make microparticles of PLGA that do not clump or aggregate.

U.S. Patent Application Publication 2011/0123446 filed by Liquidia Technologies titled "Degradable compounds and methods of use thereof, particularly with particle replication in non-wetting templates" describes degradable polymers that utilize a silyl core and can form rapidly degrading matrixes.

Additional references pertaining to particles for ocular delivery include the following. Ayalasomayajula, S. P. and Kompella, U. B. have disclosed the subconjunctival administration of celecoxib-poly(lactide co-glycolide) (PLGA) microparticles in rats (Ayalasomayajula, S. P. and Kompella, U. B., "Subconjunctivally administered celecoxib-PLGA microparticles sustain retinal drug levels and alleviate diabetes-induced oxidative stress in a rat model", *Eur. J. Pharm.*, 511, 191-198 (2005)). Danbiosyst UK Ltd., has disclosed a microparticle comprising a mixture of a biodegradable polymer, a water soluble polymer of 8,000 Daltons or higher and an active agent (U.S. Pat. No. 5,869,103). Poly-Med, Inc. has disclosed compositions comprising a hydrogel mass and a carrier having a biological active agent deposited on the carrier (U.S. Pat. No. 6,413,539). MacroMed Inc. has disclosed the use of an agent delivery system comprising a microparticle and a biodegradable gel (U.S. Pat. Nos. 6,287,588 and 6,589,549). Novartis has disclosed ophthalmic depot formulations for periocular or subconjunctival administration where the pharmacologically acceptable polymer is a polylactide-co-glycolide ester of a polyol (U.S. publication 2004/0234611, U.S. publication 2008/0305172, U.S. publication 2012/0269894, and U.S. publication 2013/0122064). The Universidad De Navarra has disclosed oral pegylated nanoparticles for carrying biologically active molecules comprising a pegylated biodegradable polymer (U.S. Pat. No. 8,628,801). Surmodics, Inc. has disclosed microparticles containing matrices for drug delivery (U.S. Pat. No. 8,663,674). Minu, L.L.C., has disclosed the use of an agent in microparticle of nanoparticle form to facilitate transmembrane transport. Emory University and Georgia Tech Research Corporation have disclosed particles dispersed in a non-Newtonian fluid that facilitates the migration of the therapeutic particles from the insertion site in the suprachoroidal space to the treatment site (U.S. 2016/0310417). Pfizer has disclosed nanoparticles as injectable depot formulations (U.S. publication 2008/0166411). Abbott has disclosed a pharmaceutical dosage form that comprises a pharmaceutically acceptable polymer for the delivery of a tyrosine kinase inhibitor (U.S. publication 2009/0203709). The Brigham and Woman's Hospital, Inc. has disclosed modified poly(lactic-co-glycolic) polymers having therapeutic agents covalently bound to the polymer (U.S. 2012/0052041). BIND Therapeutics, Inc. has disclosed therapeutic nanoparticles comprising about 50 to 99.75 weight percent of a diblock poly (lactic) acid-poly(ethylene)glycol copolymer or a diblock poly (lactic acid-co-glycolic acid)-poly(ethylene)glycol copolymer wherein the therapeutic nanoparticle comprises 10 to about 30 weight percent poly (ethylene)glycol (U.S. publication 2014/0178475). Additional publications assigned to BIND Therapeutics, Inc. include U.S. publication 2014/0248358 and U.S. publication 2014/0249158. Allergan has disclosed the use of biodegradable microspheres containing a drug to treat an ocular condition (U.S. publication 2010/0074957, U.S. publication 2014/0294986, U.S. publication 2015/0147406, EP 1742610, and WO 2013/112434). Allergan has also disclosed a biocompatible implant containing a prostamide component, which can exist in particle form, and a biodegradable polymer that allows for slow release of the drug over the course of 1 week to 6 months for the treatment of an ocular condition, such as glaucoma (U.S. application 2015/0157562 and U.S. application 2015/0099805). Jade Therapeutics has disclosed formulations containing an active agent and a polymer matrix that can be delivered directly to the target tissue or placed in a suitable delivery device (U.S. publication 2014/0107025). Bayer Healthcare has disclosed a topical ophthalmological pharmaceutical composition comprising sunitinib and at least one pharmaceutically acceptable vehicle (WO 2013/188283). pSivida Us, Inc. has disclosed biodegradable drug eluting particles comprising a microporous or mesoporous silicon body for intraocular use (U.S. Pat. No. 9,023,896). Additional patents assigned to pSivida Us, Inc. include: U.S. Pat. Nos. 8,871,241; 8,815,284; 8,574,659; 8,574,613; 8,252,307; 8,192,408 and 7,998,108. ForSight Vision4, Inc. has disclosed therapeutic devices for implantation in the eye (U.S. Pat. No. 8,808,727). Additional patents assigned to ForSight Vision4, Inc. include: U.S. Pat. Nos. 9,125,735; 9,107,748; 9,066,779; 9,050,765; 9,033,911; 8,939,948; 9,905,963; 8,795,712; 8,715,346; 8,623,395; 8,414,646; 8,399,006; 8,298,578; 8,277,830; 8,167,941; 7,883,520; 7,828,844 and 7,585,075. The Nagoya Industrial Science Research Institute has recently disclosed the use to liposomes to deliver a drug to the posterior segment of the eye (U.S. Pat. No. 9,114,070).

In order to treat ocular diseases, and in particular diseases of the posterior segment, the drug must be delivered in therapeutic levels and for a sufficient duration to achieve efficacy. This seemingly straightforward goal is difficult to achieve in practice.

The object of this invention is to provide compositions and methods to treat ocular disorders. Another objective is to provide drug delivering microparticles for sustained administration of therapeutic materials generally in vivo.

SUMMARY

The present invention provides mildly surface treated solid biodegradable microparticles that on injection in vivo, aggregate to a larger particle (pellet) in a manner that reduces unwanted side effects of the smaller particles and are suitable for long term (for example, up to, or alternatively at least, three months, four months, five months, six months or seven months or longer) sustained delivery of a therapeutic agent. In one embodiment, the mildly surface treated solid biodegradable microparticles are suitable for ocular injection, at which point the particles aggregate to form a pellet that remains outside the visual axis so as not to significantly impair vision. The particles can aggregate into one or several pellets. The size of the aggregate depends on the concentration and volume of the microparticle suspensions injected and the diluent in which the microparticles are suspended.

In one embodiment, the invention is thus surface-modified solid aggregating microparticles that include at least one biodegradable polymer, wherein the surface-modified solid aggregating microparticles have a solid core, include a therapeutic agent, have a modified surface which has been treated under mild conditions at a temperature at or less than about 18° C. to remove surface surfactant, are sufficiently small to be injected in vivo, and are capable of aggregating in vivo to form at least one pellet of at least 500 µm in vivo to provide sustained drug delivery in vivo for at least one month, two months, three months, four months, five months, six months or seven months or more. The surface modified solid aggregating microparticles are suitable, for example, for an intravitreal injection, implant, including an ocular implant, periocular delivery, or delivery in vivo outside of the eye.

In one embodiment, the surface-modified solid aggregating microparticles described herein, upon injection in vivo, aggregate in vivo to form at least one pellet of at least 500 µm in vivo to provide sustained drug delivery in vivo for at least one month, two months, three months, four months, five months, six months or seven months or more.

In another embodiment, the invention is an injectable material that includes the microparticles of the present invention in a pharmaceutically acceptable carrier for administration in vivo. The injectable material may include a compound that inhibits aggregation of microparticles prior to injection and/or a viscosity enhancer and/or a salt. In one embodiment, the injectable material has a range of concentration of the surface-modified solid aggregating microparticles of about 50 to 700 mg/ml. In certain examples, the injectable material has a concentration of the surface-modified solid aggregating microparticles that is not more than about 50, 100, 150, 200, 250, 300, 350, 400, 450, 500, 550, 600, 650 or 700 mg/ml. In one embodiment, the injectable material has a concentration of the surface-modified solid aggregating microparticles of about 200-400 mg/ml, 150-450 or 100-500 mg/ml. In certain embodiments, the injectable material has about up to 150, 200, 300 or 400 mg/ml.

The present invention further includes a process for the preparation of surface-modified solid aggregating microparticles that includes (i) a first step of preparing microparticles comprising one or more biodegradable polymers by dissolving or dispersing the polymer(s) and a therapeutic agent in one or more solvents to form a polymer and therapeutic agent solution or dispersion, mixing the polymer and the therapeutic agent solution or dispersion with an aqueous phase containing a surfactant to produce solvent-laden microparticles and then removing the solvent(s) to produce polymer microparticles that contain the therapeutic agent, polymer and surfactant; and (ii) a second step of mildly treating the surface of microparticles of step (i) at a temperature at or below about 18, 15, 10, 8 or 5° C. optionally up to about 1, 2, 3, 4, 5, 10, 30, 40, 50, 60, 70, 80, 90 100, 11, 120 or 140 minutes with an agent that removes surface surfactant, surface polymer, or surface oligomer in a manner that does not significantly produce internal pores; and (iii) isolating the surface treated microparticles.

The process can be achieved in a continuous manufacturing line or via one step or in step-wise fashion. In one embodiment, wet biodegradable microparticles can be used without isolation to manufacture surface treated solid biodegradable microparticles. In one embodiment, the surface treated solid biodegradable microparticles do not significantly aggregate during the manufacturing process. In another embodiment, the surface treated solid biodegradable microparticles do not significantly aggregate when resuspended and loaded into a syringe. In some embodiments, the syringe is approximately 30, 29, 28, 27, 26 or 25 gauge, with either normal or thin wall.

In yet another embodiment, a method for the treatment of an ocular disorder is provided that includes administering to a host in need thereof mildly surface-modified solid aggregating microparticles that include an effective amount of a therapeutic agent, wherein the surface-modified solid aggregating microparticles are injected into the eye and aggregate in vivo to form at least one pellet of at least 500 µm that provides sustained drug delivery for at least approximately one, two, three, four, five, six or seven or more months in such a manner that the pellet stays substantially outside the visual axis so as not to significantly impair vision. In one embodiment, the surface treated solid biodegradable microparticles release about 1 to about 20 percent, about 1 to about 15 percent, about 1 to about 10 percent, or about 5 to 20 percent, for example, up to about 1, 5, 10, 15 or 20 percent, of the therapeutic agent over the first twenty-four hour period. In one embodiment, the surface treated solid biodegradable microparticles release less therapeutic agent in vivo in comparison to non-treated solid biodegradable microparticles over up to about 1, 2, 3, 4, 5, 6, 7 day or even up to about a 1, 2, 3, 4, or 5 month period. In one embodiment, the surface treated solid biodegradable microparticles induce less inflammation in vivo in comparison to non-treated solid biodegradable microparticles over the course of treatment.

This invention addresses the problem of intraocular therapy using small drug loaded particles (for example, 20 to 40 μm, 10 to 30, 20 to 30, or 25 to 30 μm average diameter, or for example, not greater than about 20, 25, 26, 27, 28, 29, 30, 35 or 40 μm average diameter (Dv)) that tend to disperse in the eye due to body movement and/or aqueous flow in the vitreous. The dispersed microparticles can cause vision disruption and aggravation from floaters, inflammation, etc. The microparticles of the invention aggregate in vivo to form at least one pellet of at least 500 m and minimize vision disruption and inflammation. Further, the aggregated pellet of the surface treated microparticles is biodegradable so the aggregated pellet of the surface treated microparticles does not have to be surgically removed.

In one embodiment, the surface treatment includes treating microparticles with aqueous base, for example, sodium hydroxide and a solvent (such as an alcohol, for example ethanol or methanol, or an organic solvent such as DMF, DMSO or ethyl acetate) as otherwise described above. More generally, a hydroxide base is used, for example, potassium hydroxide. An organic base can also be used. In other embodiments, the surface treatment as described above is carried out in aqueous acid, for example hydrochloric acid. In one embodiment, the surface treatment includes treating microparticles with phosphate buffered saline and ethanol.

In some embodiments, the surface treatment is carried out at a temperature of not more than 5, 6, 7, 8, 9, 10, 11, 12, 13, 14, 15, 16, 17 or 18° C. at a reduced temperature of about 5 to about 18° C., about 5 to about 16° C., about 5 to about 15° C., about 0 to about 10° C., about 0 to about 8° C., or about 1 to about 5° C., about 5 to about 20° C., about 1 to about 10° C., about 0 to about 15° C., about 0 to about 10° C., about 1 to about 8° C., or about 1 to about 5° C. Each combination of each of these conditions is considered independently disclosed as if each combination were separately listed.

The pH of the surface treatment will of course vary based on whether the treatment is carried out in basic, neutral or acidic conditions. When carrying out the treatment in base, the pH may range from about 7.5 to about 14, including not more than about 8, 9, 10, 11, 12, 13 or 14. When carrying out the treatment in acid, the pH may range from about 6.5 to about 1, including not less than 1, 2, 3, 4, 5, or 6. When carrying out under neutral conditions, the pH may typically range from about 6.4 or 6.5 to about 7.4 or 7.5.

A key aspect of the present invention is that the treatment, whether done in basic, neutral or acidic conditions, includes a selection of the combination of the time, temperature, pH agent and solvent that causes a mild treatment that does not significantly damage the particle in a manner that forms pores, holes or channels. Each combination of each of these conditions is considered independently disclosed as if each combination were separately listed.

The treatment conditions should simply mildly treat the surface in a manner that allows the particles to remain as solid particles, be injectable without undue aggregation or clumping, and form at least one aggregate particle of at least 500 μm.

In one embodiment, the surface treatment includes treating microparticles with an aqueous solution of pH=6.6 to 7.4 or 7.5 and ethanol at a reduced temperature of about 1 to about 10° C., about 1 to about 15° C., about 5 to about 15° C., or about 0 to about 5° C. In one embodiment, the surface treatment includes treating microparticles with an aqueous solution of pH=6.6 to 7.4 or 7.5 and an organic solvent at a reduced temperature of about 0 to about 10° C., about 5 to about 8° C., or about 0 to about 5° C. In one embodiment, the surface treatment includes treating microparticles with an aqueous solution of pH=1 to 6.6 and ethanol at a reduced temperature of about 0 to about 10° C., about 0 to about 8° C., or about 0 to about 5° C. In one embodiment, the surface treatment includes treating microparticles with an organic solvent at a reduced temperature of about 0 to about 18° C., about 0 to about 16° C., about 0 to about 15° C., about 0 to about 10° C., about 0 to about 8° C., or about 0 to about 5° C. The decreased temperature of processing (less than room temperature, and typically less than 18° C.) assists to ensure that the particles are only "mildly" surface treated.

Pharmaceutical and biologic therapeutic agents can be delivered in a controlled fashion using the invention. In one embodiment, the pharmaceutical agent is a tyrosine kinase inhibitor such as sunitinib. One goal of the invention is to provide for the sustained release of pharmaceutically active compounds to the eye, and in particular the posterior of the eye, over a period of at least about one, two, three, four, five, six, seven months or more in a manner that maintains at least a concentration of a drug in the eye that is effective for the disorder to be treated. In one embodiment, the drug is administered in a surface treated microparticle that provides for a sustained release that is substantially linear. In another embodiment, the release is not linear; however, even the lowest concentration of release over the designated time period is at or above a therapeutically effective dose.

In one embodiment, the surface treated microparticle includes poly(lactic-co-glycolic acid) (PLGA). In another embodiment, the surface treated microparticle includes a polymer or copolymer that has at least PLGA and PLGA-polyethylene glycol (PEG) (referred to as PLGA-PEG). In one embodiment, the surface treated microparticle includes poly(lactic acid) (PLA). In another embodiment, the surface treated microparticle includes a polymer or copolymer that has at least PLA and PLA-polyethylene glycol (PEG) (referred to as PLA-PEG). In one embodiment, the surface treated microparticle includes polycaprolactone (PCL). In another embodiment, the surface treated microparticle includes a polymer or copolymer that has at least PCL and PCL-polyethylene glycol (PEG) (referred to as PCL-PEG). In another embodiment, the surface treated microparticle includes at least PLGA, PLGA-PEG and polyvinyl alcohol (PVA). In another embodiment, the surface treated microparticle includes at least PLA, PLA-PEG and polyvinyl alcohol (PVA). In another embodiment, the surface treated microparticle includes at least PCL, PCL-PEG and polyvinyl alcohol (PVA). In other embodiments, any combination of PLA, PLGA or PCL can be mixed with any combination of PLA-PEG, PLGA-PEG or PCL-PEG, with or without PVA, and each combination of each of these conditions is considered independently disclosed as if each were separately listed.

In one embodiment, the polyvinyl alcohol is a partially hydrolyzed polyvinyl acetate. For example, the polyvinyl acetate is at least about 78% hydrolyzed so that the polyvinyl acetate is substantially hydrolyzed. In one example, the polyvinyl acetate is at least about 88% to 98% hydrolyzed so that the polyvinyl acetate is substantially hydrolyzed.

In one embodiment, the surface treated microparticle including a pharmaceutically active compound contains from about 80 percent or 89 percent to about 99 percent PLGA, for example, at least about 80, 85, 90, 95, 96, 97, 98 or 99 percent PLGA. In other embodiments, PLA or PCL is used in place of PLGA. In yet other embodiments, a combination of PLA, PLGA and/or PCL is used.

In certain examples, the surface treated microparticle includes from about 0.5 percent to about 10 percent PLGA-PEG, about 0.5 percent to about 5 percent PLGA-PEG, about 0.5 percent to about 4 percent PLGA-PEG, about 0.5 percent to about 3 percent PLGA-PEG, or about 0.1 percent to about 1, 2, 5, or 10 percent PLGA-PEG. In other embodiments, PLA-PEG or PCL-PEG is used in place of PLGA-PEG. In other embodiments, any combination of PLGA-PEG, PLA-PEG or PCL-PEG is used in the polymeric composition with any combination of PLGA, PLA or PCL. Each combination is considered specifically described as if set out individually herein. In one embodiment, the polymeric formulation includes up to about 1, 2, 3, 4, 5, 6, 10, or 14% of the selected pegylated polymer.

In some examples, the microparticle contains from about 0.01 percent to about 0.5 percent PVA (polyvinyl alcohol), about 0.05 percent to about 0.5 percent PVA, about 0.1 percent to about 0.5 percent PVA, or about 0.25 percent to about 0.5 percent PVA. In some examples, the microparticle contains from about 0.001 percent to about 1 percent PVA, about 0.005 percent to about 1 percent PVA, about 0.075 percent to about 1 percent PVA, or about 0.085 percent to about 1 percent PVA. In some examples, the microparticle contains from about 0.01 percent to about 5.0 percent PVA, about 0.05 percent to about 5.0 percent PVA, about 0.1 percent to about 5.0 percent PVA, about 0.50 percent to about 5.0 percent PVA. In some examples, the microparticle contains from about 0.10 percent to about 1.0 percent PVA or about 0.50 percent to about 1.0 percent. In some embodiments, the microparticle contains up to about 0.10, 0.15, 0.20, 0.25, 0.30, 0.40 or 0.5% PVA. Any molecular weight PVA can be used that achieves the desired results. In one embodiment, the PVA has a molecular weight of up to about 10, 15, 20, 25, 30, 35 or 40 kd. In some embodiments, the PVA is partially hydrolyzed polyvinyl acetate, including but not limited to, up to about 70, 75, 80, 85, 88, 90 or even 95% hydrolyzed polyvinyl acetate. In one embodiment, the PVA is about 88% hydrolyzed polyvinyl acetate. In one embodiment, the PVA polymer has a molecule weight of 20,000 to 40,000 g/mol. In one embodiment, the PVA polymer has a molecular weight of 24,000 to 35,000 g/mol.

In one embodiment, the PLGA polymer has a molecular weight of 30,000 to 60,000 g/mol (also kilodalton, kDa or kD). In one embodiment, the PLGA polymer has a molecular weight of 40,000 to 50,000 g/mol (for example 40,000; 45,000 or 50,000 g/mol). In one embodiment, the PLA polymer has a molecular weight of 30,000 to 60,000 g/mol (for example 40,000; 45,000 or 50,000 g/mol). In one embodiment, the PCL polymer is used in the same range of kDa as described for PLGA or PLA.

In one embodiment, a surface treated microparticle comprises a pharmaceutically active compound. The encapsulation efficiency of the pharmaceutically active compound in the microparticle can range widely based on specific microparticle formation conditions and the properties of the therapeutic agent, for example from about 20 percent to about 90 percent, about 40 percent to about 85 percent, about 50 percent to about 75 percent. In some embodiments, the encapsulation efficiency is for example, up to about 50, 55, 60, 65, 70, 75 or 80 percent.

The amount of pharmaceutical active compound in the surface treated microparticle is dependent on the molecular weight, potency, and pharmacokinetic properties of the pharmaceutical active compound.

In one embodiment, the pharmaceutically active compound is present in an amount of at least 1.0 weight percent to about 40 weight percent based on the total weight of the surface treated microparticle. In some embodiments, the pharmaceutically active compound is present in an amount of at least 1.0 weight percent to about 35 weight percent, at least 1.0 weight percent to about 30 weight percent, at least 1.0 weight percent to about 25 weight percent, or at least 1.0 weight percent to about 20 weight percent based on the total weight of the surface treated microparticle. Nonlimiting examples of weight of active material in the microparticle are at least about 5, 6, 7, 8, 9, 10, 11, 12, 13, 14 or 15% by weight. In one example, the microparticle has about 10% by weight of active compound.

In one embodiment, the invention provides a process for producing a microparticle comprising a microparticle and a pharmaceutically active compound encapsulated in the microparticle; which process comprises:

(a) preparing a solution or suspension (organic phase) comprising: (i) PLGA or PLA (ii) PLGA-PEG or PLA-PEG (iii) a pharmaceutically active compound and (iv) one or more organic solvents;

(b) preparing an emulsion in an aqueous polyvinyl alcohol (PVA) solution (aqueous phase) by adding the organic phase into the aqueous phase and mixing at about 3,000 to about 10,000 rpm for about 1 to about 30 minutes;

(c) hardening the emulsion including solvent-laden microparticles including the pharmaceutically active compound by stirring at about room temperature until solvent substantially evaporates;

(d) centrifuging the microparticle including a pharmaceutically active compound;

(e) removing the solvent and washing the microparticle including the pharmaceutically active compound with water;

(f) filtering the microparticle including the pharmaceutically active compound to remove aggregates or particles larger than the desired size;

(g) optionally lyophilizing the microparticle comprising the pharmaceutically active compound and storing the microparticle as a dry powder in a manner that maintains stability for up to about 6, 8, 10, 12, 20, 22, or 24 months or more.

BRIEF DESCRIPTION OF THE FIGURES

FIG. 8A illustrates the in vitro aggregation of surface treated microparticles (STMP) in 5-fold diluted ProVisc at a concentration of 100 mg/mL into 4 mL of PBS after incubation at 37° C. for 2 hours (top) and after incubation at 37° C. for 2 hours followed by shaking at 250 rpm for 2 minutes on an orbital shaker (bottom) (Example 17).

FIG. 8B illustrates the in vitro aggregation of surface treated microparticles (STMP) in 5-fold diluted ProVisc at a concentration of 100 mg/mL into 4 mL of HA (5 mg/mL solution) after incubation at 37° C. for 2 hours (top) and after incubation at 37° C. for 2 hours followed by shaking at 250 rpm for 2 minutes on an orbital shaker (bottom) (Example 17).

FIG. 8C illustrates the in vitro aggregation of surface treated microparticles (STMP) in 5-fold diluted ProVisc at a concentration of 200 mg/mL into 4 mL of PBS after incubation at 37° C. for 2 hours followed by shaking at 250 rpm for 2 minutes on an orbital shaker (bottom) (Example 17).

FIG. 8D illustrates the in vitro aggregation of surface treated microparticles (STMP) in 5-fold diluted ProVisc at a concentration of 200 mg/mL into 4 mL of HA (5 mg/mL solution) after incubation at 37° C. for 2 hours followed by shaking at 250 rpm for 2 minutes on an orbital shaker (bottom) (Example 17).

FIG. 9 illustrates photos of aggregates of particles in an ex vivo cow eye 2 hours after injection (Example 18).

DETAILED DESCRIPTION

I. Terminology

Figure 1:
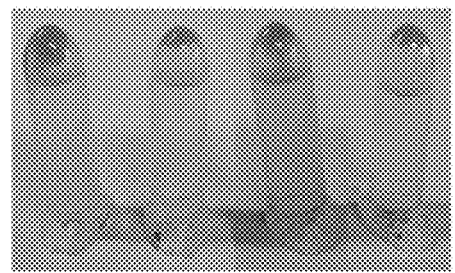
FIG. 1 illustrates the aggregation of non-surface treated microparticles (NSTMP) (S-1 and S-5) and surface treated microparticles (STMP) (S-3 and S-8) after injection into PBS and incubation at 37° C. for 2 hours. The NSTMP, S-1 and S-5, started to disperse immediately when the tubes were inverted after the 2 hour-incubation, while the STMP, S-3 and S-8, remained aggregated at the bottom of the tubes without dispersion throughout the entire period of observation (about 10 minutes). Samples from left to right are S-1, S-3, S-5 and S-8 (Example 5).

Although specific terms are employed herein, they are used in a generic and descriptive sense only and not for purposes of limitation. Unless otherwise defined, all technical and scientific terms used herein have the same meaning as commonly understood by one of ordinary skill in the art to which this presently described subject matter belongs.

Compounds are described using standard nomenclature. Unless defined otherwise, all technical and scientific terms used herein have the same meaning as is commonly understood by one of skill in the art to which this invention belongs.

The terms "a" and "an" do not denote a limitation of quantity, but rather denote the presence of at least one of the referenced item.

Recitation of ranges of values are merely intended to serve as a shorthand method of referring individually to each separate value falling within the range, unless otherwise indicated herein, and each separate value is incorporated into the specification as if it were individually recited herein. The endpoints of all ranges are included within the range and are independently combinable. All methods described herein can be performed in a suitable order unless otherwise indicated herein or otherwise clearly contradicted by context. The use of examples, or exemplary language (e.g., "such as"), is intended merely to better illustrate the invention and does not pose a limitation on the scope of the invention unless otherwise claimed.

The term "carrier" refers to a diluent, excipient, or vehicle.

A "dosage form" means a unit of administration of a composition that includes a surface treated microparticle and a therapeutically active compound. Examples of dosage forms include injections, suspensions, liquids, emulsions, implants, particles, spheres, creams, ointments, inhalable forms, transdermal forms, buccal, sublingual, topical, gel, mucosal, and the like. A "dosage form" can also include, for example, a surface treated microparticle comprising a pharmaceutically active compound in a carrier.

The term "microparticle" means a particle whose size is measured in micrometers (m). Typically, the microparticle has an average diameter of from about 1 µm to 100 µm. In some embodiments, the microparticle has an average diameter of from about 1 µm to 60 µm, for instance from about 1 µm to 40 µm; from about 10 µm to 40 µm; from about 20 µm to 40 µm; from about 25 µm to 40 µM; from about 20 µm to 35 µm. For example, the microparticle may have an average diameter of from 20 µm to 40 µm. As used herein, the term "microsphere" means a substantially spherical microparticle.

A "patient" or "host" or "subject" is typically a human, however, may be more generally a mammal. In an alternative embodiment it can refer to, for example, a cow, sheep, goat, horse, dog, cat, rabbit, rat, mouse, bird and the like.

The term "mild" or "mildly" when used to describe the surface modification of the microparticles means that the modification (typically the removal of surfactant from the surface, as opposed to the inner core, of the particle) is less severe, pronounced or extensive than when carried out at room temperature with the otherwise same conditions. In general, the surface modification of the solid microparticles of the present invention is carried out in a manner that does not create significant channels or large pores that would significantly accelerate the degradation of the microparticle in vivo, yet serves to soften and decrease the hydrophilicity of the surface to facilitate in vivo aggregation.

The term "solid" as used to characterize the mildly surface treated microparticle means that the particle is substantially continuous in material structure as opposed to heterogeneous with significant channels and large pores that would undesirably shorten the time of biodegradation.

II. Mildly Surface Treated Aggregating Microparticles and Methods

The present invention provides mildly surface treated solid biodegradable microparticles that on injection in vivo, aggregate to a larger particle (pellet) in a manner that reduces unwanted side effects of the smaller particles and are suitable for long term (for example, up to or at least three month, up to four month, up to five month, up to six months, up to seven months or longer) sustained delivery of a therapeutic agent. In one embodiment, the lightly surface treated solid biodegradable microparticles are suitable for ocular injection, at which point the particles aggregate to form a pellet and thus remains outside the visual axis as not to significantly impair vision. The particles can aggregate into one or several pellets. The size of the aggregate depends on the mass (weight) of the particles injected.

The mildly surface treated biodegradable microparticles provided herein are distinguished from "scaffold" microparticles, which are used for tissue regrowth via pores that cells or tissue material can occupy. In contrast, the present microparticles are designed to be solid materials of sufficiently low porosity that they can aggregate to form a larger combined particle that erodes primarily by surface erosion for long term controlled drug delivery.

The surface modified solid aggregating microparticles of the present invention are suitable, for example, for intravitreal injection, implant, periocular delivery, or delivery in vivo outside the eye.

The surface modified solid aggregating microparticles of the present invention are also suitable for systemic, parenteral, transmembrane, transdermal, buccal, subcutaneous, endosinusial, intra-abdominal, intra-articular, intracartilaginous, intracerebral, intracoronal, dental, intradiscal, intramuscular, intratumor, topical, or vaginal delivery in any manner useful for in vivo delivery.

In one embodiment, the invention is thus surface-modified solid aggregating microparticles that include at least one biodegradable polymer, wherein the surface-modified solid aggregating microparticles have a solid core, include a therapeutic agent, have a modified surface which has been treated under mild conditions at a temperature at or less than about 18° C. to remove surface surfactant, are sufficiently small to be injected in vivo, and aggregate in vivo to form at least one pellet of at least 500 µm in vivo in a manner that provides sustained drug delivery in vivo for at least one, two, three, four, five, six or seven months or more. The surface modified solid aggregating microparticles are suitable, for example, for an intravitreal injection, implant, including an ocular implant, periocular delivery or delivery in vivo outside of the eye.

Alternatively, the surface treatment is conducted at a temperature at or less than about 10° C., 8° C. or 5° C.

The surface treatment can be carried out at any pH that achieves the desired purpose. Nonlimiting examples of the pH are between about 6 and about 8, 6.5 and about 7.5, about 1 and about 4; about 4 and about 6; and 6 and about 8. In one embodiment the surface treatment can be conducted at a pH between about 8 and about 10. In one embodiment the surface treatment can be conducted at a pH between about 10.0 and about 13.0. In one embodiment the surface treatment can be conducted at a pH between about 12 and about 14. In one embodiment the surface treatment can be conducted with an organic solvent. In one embodiment the surface treatment can be conducted with ethanol. In other various embodiments, the surface treatment is carried out in a solvent selected from methanol, ethyl acetate and ethanol. Nonlimiting examples are ethanol with an aqueous organic base; ethanol and aqueous inorganic base; ethanol and sodium hydroxide; ethanol and potassium hydroxide; an aqueous acidic solution in ethanol; aqueous hydrochloric acid in ethanol; and aqueous potassium chloride in ethanol.

Examples of solid cores included in the present invention include solid cores comprising a biodegradable polymer with less than 10 percent porosity, 8 percent porosity, 7 percent porosity, 6 percent porosity, 5 percent porosity, 4 percent porosity, 3 percent porosity, or 2 percent porosity. Porosity as used herein is defined by ratio of void space to total volume of the surface-modified solid aggregating microparticle.

The surface-modified solid aggregating microparticles of the present invention provides sustained delivery for at least one month, or at least two months, or at least three months, or at least four months, or at least five months, or at least six months, or at least seven months.

The therapeutic agent delivered by the surface-modified solid aggregating microparticle is in one embodiment a pharmaceutical drug or a biologic. In nonlimiting examples, the pharmaceutical drugs include sunitinib, another tyrosine kinase inhibitor, an anti-inflammatory drug, an antibiotic, an immunosuppressing agent, an anti-VEGF agent, an anti-PDGF agent, or other therapeutic agents as described below.

In one embodiment the surface-modified solid aggregating microparticle has a mean diameter between 10 and 60 µm, 20 and 50 µm, 20 and 40 µm, 20 and 30 µm, 25 and 40 µm, or 25 and 35 µm.

Further, the surface-modified solid aggregating microparticles of the disclosed invention can aggregate to produce at least one pellet when administered in vivo that has a diameter of at least about 300, 400, 500 µm, 600 µm, 700 µm, 1 mm, 1.5 mm, 2 mm, 3 mm, 4 mm, or 5 mm.

In one embodiment the surface-modified solid aggregating microparticles of the present invention produces a pellet in vivo that releases the therapeutic agent without a burst of more than about 10 percent or 15 percent of total payload over a one week, or a five, four, three, two day or one day period.

In some embodiments, the long term controlled drug delivery is accomplished by a combination of surface erosion of an aggregated microparticle over several months (for example, one, two, three, or four months or more) followed by erosion of remaining parts of the aggregated microparticle, followed by slow release of active material from in vivo proteins to which it has bound over the period of long term release from the aggregated particle. In another embodiment, the microparticle degrades substantially by surface erosion over a period of at least about one, two, three, four, five or six months or more.

In another embodiment the surface-modified solid aggregating microparticles of the present invention have a drug loading of 1-40 percent, 5-25 percent, or 5-15 percent weight/weight.

Examples of polymeric compositions included in surface-modified solid aggregating microparticles of the present invention include, but are not limited to, poly(lactide co-glycolide), poly(lactide-co-glycolide) covalently linked to polyethylene glycol, more than one biodegradable polymer or copolymer mixed together, for example, a mixture of poly(lactide-co-glycolide) and poly(lactide-co-glycolide) covalently linked to polyethylene glycol, poly(lactic acid), a surfactant, such as polyvinyl alcohol (which can be hydrolyzed polyvinyl acetate).

In another embodiment, the invention is an injectable material that includes the microparticles of the present invention in a pharmaceutically acceptable carrier for administration in vivo. The injectable material may include a compound that inhibits aggregation of microparticles prior to injection and/or a viscosity enhancer and/or a salt. In one embodiment, the injectable material has a range of concentration of the surface-modified solid aggregating microparticles of about 50-700 mg/ml, 500 or less mg/ml, 400 or less mg/ml, 300 or less mg/ml, 200 or less mg/ml, or 150 or less mg/ml.

The present invention further includes a process for the preparation of surface-modified solid aggregating microparticles that includes
  (i) a first step of preparing microparticles comprising one or more biodegradable polymers by dissolving or dispersing the polymer(s) and a therapeutic agent in one or more solvents to form a polymer and therapeutic agent solution or dispersion, mixing the polymer and the therapeutic agent solution or dispersion with an aqueous phase containing a surfactant to produce solvent-laden microparticles and then removing the solvent(s) to produce microparticles that contain the therapeutic agent, polymer and surfactant; and
  (ii) a second step of mildly surface-only treating the microparticles of step (i) at a temperature at or below about 18° C. for optionally up to about 140, 120, 110, 100, 90, 80, 70, 60, 50, 40, 30, 10, 8, 5, 4, 3, 2, or 1 minutes with an agent that removes surface surfactant, surface polymers, or surface oligomers in a manner that does not significantly produce internal pores; and
  (iii) isolating the surface treated microparticles.

In certain embodiments step (ii) above is carried out at a temperature below 17° C., 15° C., 10° C., or 5° C. Further, step (iii) is optionally carried out at a temperature below 25° C., below 17° C., 15° C., 10° C., 8° C. or 5° C. Step (ii), for example, can be carried out for less than 8, less than 6, less than 4, less than 3, less than 2, or less than 1 minutes. In one embodiment, step (ii) is carried out for less than 60, 50, 40, 30, 20, or 10 minutes.

In one embodiment, the process of manufacturing surface-modified solid aggregating microparticles includes using an agent that removes surface surfactant. Nonlimiting examples include for example, those selected from: aqueous acid, phosphate buffered saline, water, aqueous NaOH, aqueous hydrochloric acid, aqueous potassium chloride, alcohol or ethanol.

In one embodiment, the process of manufacturing surface-modified solid aggregating microparticles includes using an agent that removes surface surfactant which comprises, for example, a solvent selected from an alcohol, for example, ethanol; ether, acetone, acetonitrile, DMSO, DMF, THF, dimethylacetamide, carbon disulfide, chloroform, 1,1- dichloroethane, dichloromethane, ethyl acetate, heptane, hexane, methanol, methyl acetate, methyl t-butyl ether (MTBE), pentane, propanol, 2-propanol, toluene, N-methyl pyrrolidinone (NMP), acetamide, piperazine, triethylenediamine, diols, and $CO_2$.

The agent that removes the surface surfactant can comprise a basic buffer solution. Further, the agent that removes surface surfactant can comprises a base selected from sodium hydroxide, lithium hydroxide, potassium hydroxide, calcium hydroxide, magnesium hydroxide, lithium amide, sodium amide, barium carbonate, barium hydroxide, barium hydroxide hydrate, calcium carbonate, cesium carbonate, cesium hydroxide, lithium carbonate, magnesium carbonate, potassium carbonate, sodium carbonate, strontium carbonate, ammonia, methylamine, ethylamine, propylamine, isopropylamine, dimethylamine, diethylamine, dipropylamine, diisopropylamine, trimethylamine, triethylamine, tripropylamine, triisopropylamine, aniline, methylaniline, dimethylaniline, pyridine, azajulolidine, benzylamine, methylbenzylamine, dimethylbenzylamine, DABCO, 1,5-diazabicyclo[4.3.0]non-5-ene, 1,8-diazabicyclo[5.4.0]non-7-ene, 2,6-lutidine, morpholine, piperidine, piperazine, Proton-sponge, 1,5,7-Triazabicyclo[4.4.0]dec-5-ene, tripelennamine, ammonium hydroxide, triethanolamine, ethanolamine, and Trizma.

In one embodiment, the process of manufacturing surface-modified solid aggregating microparticles includes using an agent that removes surface surfactant, for example, those selected from the following: aqueous acid, phosphate buffered saline, water, or NaOH in the presence of a solvent such as an alcohol, for example, ethanol, ether, acetone, acetonitrile, DMSO, DMF, THF, dimethylacetamide, carbon disulfide, chloroform, 1,1-dichloroethane, dichloromethane, ethyl acetate, heptane, hexane, methanol, methyl acetate, methyl t-butyl ether (MTBE), pentane, ethanol, propanol, 2-propanol, toluene, N-methyl pyrrolidinone (NMP), acetamide, piperazine, triethylenediamine, diols, and $CO_2$.

In one embodiment, the agent that removes the surface surfactant can comprise an aqueous acid. The agent that removes the surface surfactant can comprise an acid derived from inorganic acids including, but not limited to, hydrochloric, hydrobromic, sulfuric, sulfamic, phosphoric, nitric and the like; or organic acids including, but not limited to, acetic, propionic, succinic, glycolic, stearic, lactic, malic, tartaric, citric, ascorbic, pamoic, maleic, hydroxymaleic, phenylacetic, glutamic, benzoic, salicylic, mesylic, esylic, besylic, sulfanilic, 2-acetoxybenzoic, fumaric, toluenesulfonic, methanesulfonic, ethane disulfonic, oxalic, isethionic, HOOC—$(CH_2)_n$—COOH where n is 0-4, and the like.

In one embodiment, the agent that removes surface surfactant is not a degrading agent of the biodegradable polymer under the conditions of the reaction. The hydrophilicity of the microparticles can be decreased by removing surfactant.

In one embodiment, the process of manufacturing surface-modified solid aggregating microparticles comprises using an agent that removes surface surfactant that comprises a solvent selected from an alcohol, for example, ethanol, ether, acetone, acetonitrile, DMSO, DMF, THF, dimethylacetamide, carbon disulfide, chloroform, 1,1-dichloroethane, dichloromethane, ethyl acetate, heptane, hexane, methanol, methyl acetate, methyl t-butyl ether (MTBE), pentane, ethanol, propanol, 2-propanol, toluene, N-methyl pyrrolidinone (NMP), acetamide, piperazine, triethylenediamine, diols, and $CO_2$. In a typical embodiment the process of surface treating, comprises an agent that removes surface surfactant that comprises ethanol.

The encapsulation efficiency of the process of manufacturing surface-modified solid aggregating microparticles depends on the microparticle forming conditions and the properties of the therapeutic agent. In certain embodiments, the encapsulation efficiency can be greater than about 50 percent, greater than about 75 percent, greater than about 80 percent, or greater than about 90 percent.

In one embodiment, the process of manufacturing surface-modified solid aggregating microparticles includes 75/25 PLGA as a biodegradable polymer.

In an alternative embodiment, the process of manufacturing surface-modified solid aggregating microparticles is carried out below about a pH of 14 and above a pH of 12, below a pH of 12 and above a pH of 10, below a pH of about 10 and above a pH of 8, below about a pH of 8 and above a pH of about 6, neutral pH, below about a pH of 7 and above a pH of 4, below about a pH of 4 and above a pH of about 1.0.

In one embodiment, step (ii) above is carried out for a time of about less than 140, 120, 110, 100, 90, 60, 40, 30, 20, 10, 3, 2, or 1 minutes.

In yet another embodiment, a method for the treatment of an ocular disorder is provided that includes administering to a host in need thereof surface-modified solid aggregating microparticles that include an effective amount of a therapeutic agent, wherein the therapeutic agent containing surface-modified solid aggregating microparticles are injected into the eye and in vivo aggregate to form at least one pellet of at least 500 µm that provides sustained drug delivery for at least one, two, or three, four, five, six, seven or more months in such a manner that the pellet stays substantially outside the visual axis as not to significantly impair vision.

In an alternative embodiment, the weight percent of surface-modified solid aggregating microparticles that are not aggregated into a larger pellet in vivo is about 10 percent or less, 7 percent or less, 5 percent or less, or 2 percent or less by total weight administered.

In one embodiment, the surface-modified solid aggregating microparticles do not cause substantial inflammation in the eye.

In another embodiment, the surface-modified solid aggregating microparticles do not cause an immune response in the eye.

In one embodiment, the surface-modified microparticles of the present invention, as described herein, are used to treat a medical disorder which is glaucoma, a disorder mediated by carbonic anhydrase, a disorder or abnormality related to an increase in intraocular pressure (IOP), a disorder mediated by nitric oxide synthase (NOS), or a disorder requiring neuroprotection such as to regenerate/repair optic nerves. In another embodiment more generally, the disorder treated is allergic conjunctivitis, anterior uveitis, cataracts, dry or wet age-related macular degeneration (AMD), or diabetic retinopathy.

Another embodiment is provided that includes the administration of a surface treated microparticle comprising an effective amount of a pharmaceutically active compound or a pharmaceutically acceptable salt thereof, optionally in a pharmaceutically acceptable carrier, to a host to treat an ocular or other disorder that can benefit from topical or local delivery. The therapy can be delivery to the anterior or posterior chamber of the eye. In specific aspects, a surface treated microparticle comprising an effective amount of a pharmaceutically active compound is administered to treat a disorder of the cornea, conjunctiva, aqueous humor, iris, ciliary body, lens sclera, choroid, retinal pigment epithelium, neural retina, optic nerve, or vitreous humor.

Any of the compositions described can be administered to the eye as described further herein in any desired form of administration, including via intravitreal, intrastromal, intracameral, subtenon, sub-retinal, retrobulbar, peribulbar, suprachoroidal, subchoroidal, conjunctival, subconjunctival, episcleral, posterior juxtascleral, circumcorneal, tear duct injections, or through a mucus, mucin, or a mucosal barrier, in an immediate or controlled release fashion.

In one embodiment the disclosure provides a beta-adrenergic antagonist for ocular therapy, which can be released from a surface treated microparticle while maintaining efficacy over an extended time such as up to at least 1, 2, 3, 4, 5, 6, or 7 months.

In one embodiment the disclosure provides a prostaglandin analog for ocular therapy, which can be released from a surface treated microparticle while maintaining efficacy over an extended time such as up to at least 1, 2, 3, 4, 5, 6, or 7 months.

In one embodiment the disclosure provides an adrenergic agonist for ocular therapy, which can be released from a surface treated microparticle while maintaining efficacy over an extended time such as up to at least 1, 2, 3, 4, 5, 6, or 7 months.

In one embodiment the disclosure provides a carbonic anhydrase inhibitor for ocular therapy, which can be released from a surface treated microparticle while maintaining efficacy over an extended time such as up to at least 1, 2, 3, 4, 5, 6, or 7 months.

In one embodiment the disclosure provides a parasympathomimetic agent for ocular therapy, which can be released from a surface treated microparticle while maintaining efficacy over an extended time such as up to at least 1, 2, 3, 4, 5, 6, or 7 months.

In one embodiment the disclosure provides a dual anti-VEGF/anti-PDGF agent for ocular therapy, which can be released from a surface treated microparticle while maintaining efficacy over an extended time such as up to at least 1, 2, 3, 4, 5, 6, or 7 months.

Methods of treating or preventing ocular disorders, including glaucoma, a disorder mediated by carbonic anhydrase, a disorder or abnormality related to an increase in intraocular pressure (IOP), a disorder mediated by nitric oxide synthase (NOS), a disorder requiring neuroprotection such as to regenerate/repair optic nerves, allergic conjunctivitis, anterior uveitis, cataracts, dry or wet age-related macular degeneration (AMD) or diabetic retinopathy are disclosed comprising administering a therapeutically effective amount of a surface treated microparticle comprising a pharmaceutically active compound to a host, including a human, in need of such treatment. In one embodiment, the host is a human.

In another embodiment, an effective amount of a surface treated microparticle comprising a pharmaceutically active compound is provided to decrease intraocular pressure (IOP) caused by glaucoma. In an alternative embodiment, the surface treated microparticle comprising a pharmaceutically active compound can be used to decrease intraocular pressure (IOP), regardless of whether it is associated with glaucoma.

In one embodiment, the disorder is associated with an increase in intraocular pressure (IOP) caused by potential or previously poor patient compliance to glaucoma treatment. In yet another embodiment, the disorder is associated with potential or poor neuroprotection through neuronal nitric oxide synthase (NOS). The surface treated microparticle comprising a pharmaceutically active compound provided herein may thus dampen or inhibit glaucoma in a host, by administration of an effective amount in a suitable manner to a host, typically a human, in need thereof.

Methods for the treatment of a disorder associated with glaucoma, increased intraocular pressure (IOP), optic nerve damage caused by either high intraocular pressure (IOP) or neuronal nitric oxide synthase (NOS) are provided that includes the administration of an effective amount of a surface treated microparticle comprising a pharmaceutically active compound are also disclosed.

In one aspect of the present invention, an effective amount of a pharmaceutically active compound as described herein is incorporated into a surface treated microparticle, e.g., for convenience of delivery and/or sustained release delivery. The use of materials in micrometer scale provides one the ability to modify fundamental physical properties such as solubility, diffusivity, and drug release characteristics. These micrometer scale agents may provide more effective and/or more convenient routes of administration, lower therapeutic toxicity, extend the product life cycle, and ultimately reduce healthcare costs. As therapeutic delivery systems, surface treated microparticles can allow targeted delivery and sustained release.

In another aspect of the present invention, the surface treated microparticle is coated with a surface agent. The present invention further comprises a method of producing surface treated microparticles comprising a pharmaceutically active compound. The present invention further comprises methods of using the surface treated microparticles comprising a pharmaceutically active compound to treat a patient.

In one embodiment, surface treated microparticles including a pharmaceutically active compound are obtained by forming an emulsion and using a bead column as described in, for example, U.S. Pat. No. 8,916,196.

In one embodiment, surface treated microparticles including a pharmaceutically active compound are obtained by using a vibrating mesh or microsieve.

In one embodiment, surface treated microparticles including a pharmaceutically active compound are obtained by using slurry sieving.

The processes of producing microspheres described herein are amenable to methods of manufacture that narrow the size distribution of the resultant particles. In one embodiment, the particles are manufactured by a method of spraying the material through a nozzle with acoustic excitation (vibrations) to produce uniform droplets. A carrier stream can also be utilized through the nozzle to allow further control of droplet size. Such methods are described in detail in: Berkland, C., K. Kim, et al. (2001). "Fabrication of PLG microspheres with precisely controlled and monodisperse size distributions." *J Control Release* 73(1): 59-74; Berkland, C., M. King, et al. (2002). "Precise control of PLG microsphere size provides enhanced control of drug release rate." *J Control Release* 82(1): 137-147; Berkland, C., E. Pollauf, et al. (2004). "Uniform double-walled polymer microspheres of controllable shell thickness." *J Control Release* 96(1): 101-111.

In another embodiment, microparticles of uniform size can be manufactured by methods that utilize microsieves of the desired size. The microsieves can either be used directly during production to influence the size of microparticles formed, or alternatively post production to purify the microparticles to a uniform size. The microsieves can either be mechanical (inorganic material) or biological in nature (organic material such as a membrane). One such method is described in detail in U.S. Pat. No. 8,100,348.

In one embodiment, the surface treated microparticles comprise a therapeutically active compound and have a particle size of 25<Dv50<40 rpm, Dv90<45 µm.

In one embodiment, the surface treated microparticles comprise a therapeutically active compound and have a particle size of Dv10>10 µm.

In one embodiment, the surface treated microparticles comprise a therapeutically active compound and have only residual solvents that are pharmaceutically acceptable.

In one embodiment, the surface treated microparticles comprise a therapeutically active compound and afford a total release of greater than eighty percent by day 14.

In one embodiment, the surface treated microparticles comprise a therapeutically active agent and have syringeability with a regular-walled 26, 27, 28, 29 or 30 gauge needle of 200 mg/ml with no clogging of the syringe.

In one embodiment, the surface treated microparticles comprise a therapeutically active agent and have syringeability with a thin-walled 26, 27, 28, 29 or 30 gauge needle of 200 mg/ml with no clogging of the syringe.

In one embodiment, the surface treated microparticles comprises sunitinib have a particle size of 25<Dv50<40 µm, Dv90<45 µm.

In one embodiment, the surface treated microparticles comprising sunitinib have a particle size of Dv10>10 µm.

In one embodiment, the surface treated microparticles comprising sunitinib have only residual solvents that are pharmaceutically acceptable.

In one embodiment, the surface treated microparticles comprising sunitinib afford a total release of greater than eighty percent by day 14.

In one embodiment, the surface treated microparticles comprising sunitinib have syringeability with a regular-walled 26, 27, 28, 29 or 30 gauge needle of 200 mg/ml with no clogging of the syringe.

In one embodiment, the surface treated microparticles comprising sunitinib have syringeability with a thin-walled 26, 27, 28, 29 or 30 gauge needle of 200 mg/ml with no clogging of the syringe.

In one embodiment, the surface treated microparticles comprising sunitinib have an endotoxin level of less than 0.02 EU/mg.

In one embodiment, the surface treated microparticles comprising sunitinib have a bioburden level of less than 10 CFU/g.

Biodegradable Polymers

The surface treated microparticles can include one or more biodegradable polymers or copolymers. The polymers should be biocompatible in that they can be administered to a patient without an unacceptable adverse effect. Biodegradable polymers are well known to those in the art and are the subject of extensive literature and patents. The biodegradable polymer or combination of polymers can be selected to provide the target characteristics of the microparticles, including the appropriate mix of hydrophobic and hydrophilic qualities, half-life and degradation kinetics in vivo, compatibility with the therapeutic agent to be delivered, appropriate behavior at the site of injection, etc.

For example, it should be understood by one skilled in the art that by manufacturing a microparticle from multiple polymers with varied ratios of hydrophobic, hydrophilic, and biodegradable character that the properties of the microparticle can be designed for the target use. As an illustration, a microparticle manufactured with 90 percent PLGA and 10 percent PEG is more hydrophilic than a microparticle manufactured with 95 percent PLGA and 5 percent PEG. Further, a microparticle manufactured with a higher content of a less biodegradable polymer will in general degrade more slowly. This flexibility allows microparticles of the present invention to be tailored to the desired level of solubility, rate of release of pharmaceutical agent, and rate of degradation.

In certain embodiments, the microparticle includes a poly($\alpha$-hydroxyacid). Examples of poly($\alpha$-hydroxyacids) include poly lactic acid (PLA), polyglycolic acid (PGA), poly(D,L-lactide-co-glycolide)(PLGA), and poly D,L-lactic acid (PDLLA). polyesters, poly ($\epsilon$-caprolactone), poly (3-hydroxy-butyrate), poly (s-caproic acid), poly (p-dioxanone), poly (propylene fumarate), poly (ortho esters), polyol/diketene acetals, addition polymers, polyanhydrides, poly (sebacic anhydride) (PSA), poly (carboxybis-carboxyphenoxyphosphazene) (PCPP), poly [bis (p-carboxyphenoxy) methane] (PCPM), copolymers of SA, CPP and CPM (as described in Tamat and Langer in *Journal of Biomaterials Science Polymer* Edition, 3, 315-353, 1992 and by Domb in Chapter 8 of *The Handbook of Biodegradable Polymers*, Editors Domb A J and Wiseman R M, Harwood Academic Publishers), and poly (amino acids).

In one embodiment, the microparticle includes about at least 90 percent hydrophobic polymer and about not more than 10 percent hydrophilic polymer. Examples of hydrophobic polymers include polyesters such as poly lactic acid (PLA), polyglycolic acid (PGA), poly(D,L-lactide-co-glycolide)(PLGA), and poly D,L-lactic acid (PDLLA); polycaprolactone; polyanhydrides, such as polysebacic anhydride, poly(maleic anhydride); and copolymers thereof. Examples of hydrophilic polymers include poly(alkylene glycols) such as polyethylene glycol (PEG), polyethylene oxide (PEO), and poly(ethylene glycol) amine; polysaccharides; poly(vinyl alcohol) (PVA); polypyrrolidone; polyacrylamide (PAM); polyethylenimine (PEI); poly(acrylic acid); poly(vinylpyrolidone) (PVP); or a copolymer thereof.

In one embodiment, the microparticle includes about at least 85 percent hydrophobic polymer and at most 15 percent hydrophilic polymer.

In one embodiment, the microparticle includes about at least 80 percent hydrophobic polymer and at most 20 percent hydrophilic polymer.

In one embodiment, the microparticle includes PLGA.

In one embodiment, the microparticle includes a copolymer of PLGA and PEG.

In one embodiment, the microparticle includes a copolymer of PLA and PEG.

In one embodiment, the microparticle comprises PLGA and PLGA-PEG, and combinations thereof.

In one embodiment, the microparticle comprises PLA and PLA-PEG.

In one embodiment, the microparticle includes PVA.

In one embodiment, the microparticles include PLGA, PLGA-PEG, PVA, or combinations thereof.

In one embodiment, the microparticles include the biocompatible polymers PLA, PLA-PEG, PVA, or combinations thereof.

In one embodiment, the microparticles have a mean size of about 25 µm to about 30 µm and a median size of about 29 µm to about 31 µm before surface treatment.

In one embodiment, the microparticles after surface treatment have about the same mean size and median size. In another embodiment, the microparticles after surface treatment have a mean size which is larger than the median size. In another embodiment, the microparticles after surface treatment have a mean size which is smaller than the median size.

In one embodiment, the microparticles have a mean size of about 25 µm to about 30 µm or 30 to 33 µm and a median size of about 31 µm to about 33 µm after surface treatment with approximately 0.0075 M NaOH/ethanol to 0.75 M NaOH/ethanol (30:70, v:v).

In one embodiment, the microparticles have a mean size of about 25 µm to about 30 µm or 30 to 33 µm and a median size of about 31 µm to about 33 µm after surface treatment with approximately 0.75 M NaOH/ethanol to 2.5 M NaOH/ethanol (30:70, v:v).

In one embodiment, the microparticles have a mean size of about 25 µm to about 30 µm or 30 to 33 µm and a median size of about 31 µm to about 33 µm after surface treatment with approximately 0.0075 M HCl/ethanol to 0.75 M NaOH/ethanol (30:70, v:v).

In one embodiment, the microparticles have a mean size of about 25 µm to about 30 µm or 30 to 33 µm and a median size of about 31 µm to about 33 µm after surface treatment with approximately 0.75 M NaOH/ethanol to 2.5 M HCl/ethanol (30:70, v:v).

In one embodiment, a surface-modified solid aggregating microparticle is manufactured using a wet microparticle.

In one embodiment, the surface-modified solid aggregating microparticle can release a therapeutic agent over a longer period of time when compared to a non-surface treated microparticle.

In one embodiment, a surface-modified solid aggregating microparticle contains less surfactant than a microparticle prior to the surface modification.

In one embodiment, a surface-modified solid aggregating microparticle is more hydrophobic than a microparticle prior to the surface modification.

In one embodiment, a surface-modified solid aggregating microparticle is less inflammatory than a non-surface treated microparticle.

In one embodiment, the agent that removes the surface surfactant of a surface-modified solid aggregating microparticle comprises a solvent that partially dissolves or swells the surface-modified solid aggregating microparticle.

In one aspect of the present invention, an effective amount of a pharmaceutically active compound as described herein is incorporated into a surface treated microparticle, e.g., for convenience of delivery and/or sustained release delivery. The use of materials provides the ability to modify fundamental physical properties such as solubility, diffusivity, and drug release characteristics. These micrometer scale agents may provide more effective and/or more convenient routes of administration, lower therapeutic toxicity, extend the product life cycle, and ultimately reduce healthcare costs. As therapeutic delivery systems, surface treated microparticles can allow targeted delivery and sustained release.

Surfactants

In one embodiment, the manufacture of the microparticle includes a surfactant. Examples of surfactants include, for example, polyoxyethylene glycol, polyoxypropylene glycol, decyl glucoside, lauryl glucoside, octyl glucoside, polyoxyethylene glycol octylphenol, Triton X-100, glycerol alkyl ester, glyceryl laurate, cocamide MEA, cocamide DEA, dodecyldimethylamine oxide, and poloxamers. Examples of poloxamers include, poloxamers 188, 237, 338 and 407. These poloxamers are available under the trade name Pluronic® (available from BASF, Mount Olive, N.J.) and correspond to Pluronic® F-68, F-87, F-108 and F-127, respectively. Poloxamer 188 (corresponding to Pluronic® F-68) is a block copolymer with an average molecular mass of about 7,000 to about 10,000 Da, or about 8,000 to about 9,000 Da, or about 8,400 Da. Poloxamer 237 (corresponding to Pluronic® F-87) is a block copolymer with an average molecular mass of about 6,000 to about 9,000 Da, or about 6,500 to about 8,000 Da, or about 7,700 Da. Poloxamer 338 (corresponding to Pluronic® F-108) is a block copolymer with an average molecular mass of about 12,000 to about 18,000 Da, or about 13,000 to about 15,000 Da, or about 14,600 Da. Poloxamer 407 (corresponding to Pluronic® F-127) is a polyoxyethylene-polyoxypropylene triblock copolymer in a ratio of between about E101 P56 E101 to about E106 P70 E106, or about E101 P56E101, or about E106 P70 E106, with an average molecular mass of about 10,000 to about 15,000 Da, or about 12,000 to about 14,000 Da, or about 12,000 to about 13,000 Da, or about 12,600 Da.

Additional examples of surfactants that can be used in the invention include, but are not limited to, polyvinyl alcohol (which can be hydrolyzed polyvinyl acetate), polyvinyl acetate, Vitamin E-TPGS, poloxamers, cholic acid sodium salt, dioctyl sulfosuccinate sodium, hexadecyltrimethyl ammonium bromide, saponin, TWEEN® 20, TWEEN® 80, sugar esters, Triton X series, L-a-phosphatidylcholine (PC), 1,2-dipalmitoylphosphatidycholine (DPPC), oleic acid, sorbitan trioleate, sorbitan mono-oleate, sorbitan monolaurate, polyoxyethylene (20) sorbitan monolaurate, polyoxyethylene (20) sorbitan monooleate, natural lecithin, oleyl polyoxyethylene (2) ether, stearyl polyoxyethylene (2) ether, lauryl polyoxyethylene (4) ether, block copolymers of oxyethylene and oxypropylene, synthetic lecithin, diethylene glycol dioleate, tetrahydrofurfuryl oleate, ethyl oleate, isopropyl myristate, glyceryl monooleate, glyceryl monostearate, glyceryl monoricinoleate, cetyl alcohol, stearyl alcohol, cetylpyridinium chloride, benzalkonium chloride, olive oil, glyceryl monolaurate, corn oil, cotton seed oil, sunflower seed oil, lecithin, oleic acid, and sorbitan trioleate.

It should be recognized by one skilled in the art that some surfactants can be used as polymers in the manufacture of the microparticle. It should also be recognized by one skilled in the art that in some manufacture the microparticle may retain a small amount of surfactant which allows further modification of properties as desired.

III. Examples of Disorders to be Treated

In one embodiment, the composition includes a surface treated microparticle which comprises: a surface treated microparticle and a pharmaceutically active compound encapsulated in the surface treated microparticle optionally in combination with a pharmaceutically acceptable carrier, excipient, or diluent. In one embodiment, the composition is a pharmaceutical composition for treating an eye disorder or eye disease.

Non-limiting exemplary eye disorders or diseases treatable with the composition include age related macular degeneration, alkaline erosive keratoconjunctivitis, allergic conjunctivitis, allergic keratitis, anterior uveitis, Behcet's disease, blepharitis, blood-aqueous barrier disruption, chorioiditis, chronic uveitis, conjunctivitis, contact lens-induced keratoconjunctivitis, corneal abrasion, corneal trauma, corneal ulcer, crystalline retinopathy, cystoid macular edema, dacryocystitis, diabetic keratopathy, diabetic macular edema, diabetic retinopathy, dry eye disease, dry age-related macular degeneration, eosinophilic granuloma, episcleritis, exudative macular edema, Fuchs' Dystrophy, giant cell arteritis, giant papillary conjunctivitis, glaucoma, glaucoma surgery failure, graft rejection, herpes zoster, inflammation after cataract surgery, iridocorneal endothelial syndrome, iritis, keratoconjunctivitis sicca, keratoconjunctivitis inflammatory disease, keratoconus, lattice dystrophy, map-dotfingerprint dystrophy, necrotic keratitis, neovascular diseases involving the retina, uveal tract or cornea, for example, neovascular glaucoma, corneal neovascularization, neovascularization resulting following a combined vitrectomy and lensectomy, neovascularization of the optic nerve, and neovascularization due to penetration of the eye or contusive ocular injury, neuroparalytic keratitis, non-infectious uveitis ocular herpes, ocular lymphoma, ocular rosacea, ophthalmic infections, ophthalmic pemphigoid, optic neuritis, panuveitis, papillitis, pars planitis, persistent macular edema, phacoanaphylaxis, posterior uveitis, post-operative inflammation, proliferative diabetic retinopathy, proliferative sickle cell retinopathy, proliferative vitreoretinopathy, retinal artery occlusion, retinal detachment, retinal vein occlusion, retinitis pigmentosa, retinopathy of prematurity, rubeosis iritis, scleritis, Stevens-Johnson syndrome, sympathetic ophthalmia, temporal arteritis, thyroid associated ophthalmopathy, uveitis, vernal conjunctivitis, vitamin A insufficiency-induced keratomalacia, vitritis, and wet age-related macular degeneration.

IV. Therapeutically Active Agents to be Delivered

A wide variety of therapeutic agents can be delivered in a long term sustained manner in vivo using the present invention.

A "therapeutically effective amount" of a pharmaceutical composition/combination of this invention means an amount effective, when administered to a patient, to provide a therapeutic benefit such as an amelioration of symptoms of the selected disorder, typically an ocular disorder. In certain aspects, the disorder is glaucoma, a disorder mediated by carbonic anhydrase, a disorder or abnormality related to an increase in intraocular pressure (IOP), a disorder mediated by nitric oxide synthase (NOS), a disorder requiring neuroprotection such as to regenerate/repair optic nerves, allergic conjunctivitis, anterior uveitis, cataracts, dry or wet age-related macular degeneration (AMD), or diabetic retinopathy.

A "pharmaceutically acceptable salt" is formed when a therapeutically active compound is modified by making an inorganic or organic, non-toxic, acid or base addition salt thereof. Salts can be synthesized from a parent compound that contains a basic or acidic moiety by conventional chemical methods. Generally, such a salt can be prepared by reacting a free acid form of the compound with a stoichiometric amount of the appropriate base (such as Na, Ca, Mg, or K hydroxide, carbonate, bicarbonate, or the like), or by reacting a free base form of the compound with a stoichiometric amount of the appropriate acid. Such reactions are typically carried out in water or in an organic solvent, or in a mixture of the two. Generally, non-aqueous media like ether, ethyl acetate, ethanol, isopropanol, or acetonitrile are typical, where practicable. Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts and the quaternary ammonium salts of the parent compound formed, for example, from non-toxic inorganic or organic acids. For example, conventional non-toxic acid salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, mesylic, esylic, besylic, sulfanilic, 2-acetoxybenzoic, fumaric, toluenesulfonic, methanesulfonic, ethane disulfonic, oxalic, isethionic, HOOC—$(CH_2)_n$—COOH where n is 0-4, and the like. Lists of additional suitable salts may be found, e.g., in *Remington's Pharmaceutical Sciences*, 17th ed., Mack Publishing Company, Easton, Pa., p. 1418 (1985).

In one embodiment, the surface treated microparticle of the present invention can comprise a compound for the treatment of glaucoma, for instance a beta-adrenergic antagonists, a prostaglandin analog, an adrenergic agonist, a carbonic anhydrase inhibitor, a parasympathomimetic agent, a dual anti-VEGF/Anti-PDGF therapeutic or a dual leucine zipper kinase (DLK) inhibitor. In another embodiment, the surface treated microparticle of the present invention can comprise a compound for the treatment of diabetic retinopathy. Such compounds may be administered in lower doses according to the invention as they may be administered at the site of the ocular disease.

Examples of beta-adrenergic antagonists include, but are not limited to, timolol (Timoptic®), levobunolol (Betagan®), carteolol (Ocupress®), and metipranolol (OptiPranolol®).

Examples of prostaglandin analogs include, but are not limited to, latanoprost (Xalatan®), travoprost (Travatan®), bimatoprost (Lumigan®) and tafluprost (Zioptan™).

Examples of adrenergic agonists include, but are not limited to, brimonidine (Alphagan®), epinephrine, dipivefrin (Propine®) and apraclonidine (Lopidine®).

Examples of carbonic anhydrase inhibitors include, but are not limited to, dorzolamide (Trusopt®), brinzolamide (Azopt®), acetazolamide (Diamox®) and methazolamide (Neptazane®), see structures below:

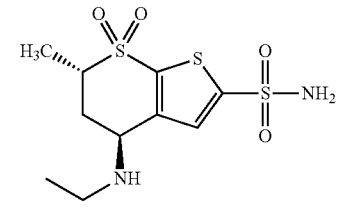

dorzolamide

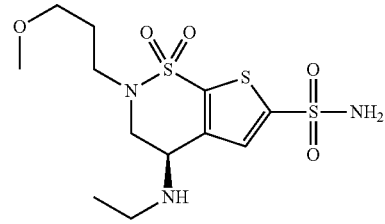

brinzolamide

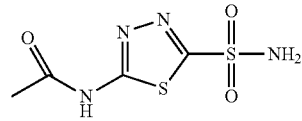

acetazolamide

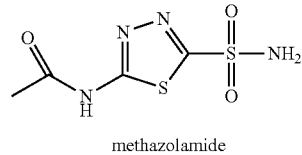

methazolamide

An example of a parasympathomimetic includes, but is not limited to, pilocarpine.

DLK inhibitors include, but are not limited to, Crizotinib, KW-2449 and Tozasertib, see structure below.

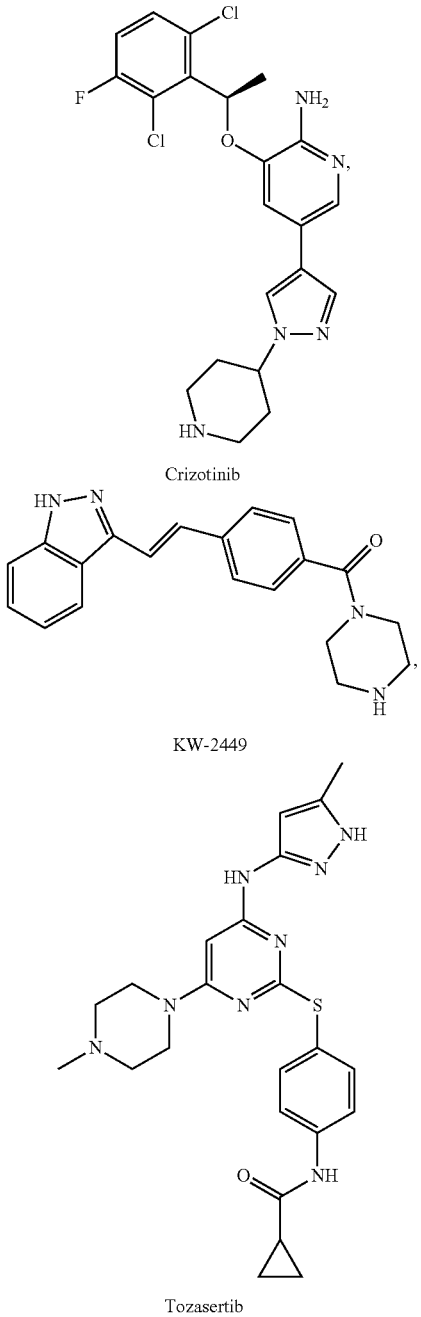

Drugs used to treat diabetic retinopathy include, but are not limited to, ranibizumab (Lucentis®).

In one embodiment, the dual anti-VEGF/Anti-PDGF therapeutic is sunitinib malate (Sutent®). As de In one embodiment, the compound is a treatment for glaucoma and can be used as an effective amount to treat a host in need of glaucoma treatment.

In another embodiment, the compound acts through a mechanism other than those associated with glaucoma to treat a disorder described herein in a host, typically a human.

In one embodiment, the therapeutic agent is selected from a phosphoinositide 3-kinase (PI3K) inhibitor, a Bruton's tyrosine kinase (BTK) inhibitor, or a spleen tyrosine kinase (Syk) inhibitor, or a combination thereof.

PI3K inhibitors that may be used in the present invention are well known. Examples of PI3 kinase inhibitors include but are not limited to Wortmannin, demethoxyviridin, perifosine, idelalisib, Pictilisib, Palomid 529, ZSTK474, PWT33597, CUDC-907, and AEZS-136, duvelisib, GS-9820, BKM120, GDC-0032 (Taselisib) (2-[4-[2-(2-Isopropyl-5-methyl-1,2,4-triazol-3-yl)-5,6-dihydroimidazo[1,2-d][1,4]benzoxazepin-9-yl]pyrazol-1-yl]-2-methylpropanamide), MLN-1117 ((2R)-1-Phenoxy-2-butanyl hydrogen (S)-methylphosphonate; or Methyl(oxo) {[(2R)-1-phenoxy-2-butanyl]oxy}phosphonium)), BYL-719 ((2 S)—N1-[4-Methyl-5-[2-(2,2,2-trifluoro-1,1-dimethylethyl)-4-pyridinyl]-2-thiazolyl]-1,2-pyrrolidinedicarboxamide), GSK2126458 (2,4-Difluoro-N-{2-(methyloxy)-5-[4-(4-pyridazinyl)-6-quinolinyl]-3-pyridinyl}benzenesulfonamide) (omipalisib), TGX-221 ((+)-7-Methyl-2-(morpholin-4-yl)-9-(1-phenylaminoethyl)-pyrido[1,2-a]-pyrimidin-4-one), GSK2636771 (2-Methyl-1-(2-methyl-3-(trifluoromethyl)benzyl)-6-morpholino-1H-benzo[d]imidazole-4-carboxylic acid dihydrochloride), KIN-193 ((R)-2-((1-(7-methyl-2-morpholino-4-oxo-4H-pyrido[1,2-a]pyrimidin-9-yl)ethyl)amino)benzoic acid), TGR-1202/RP5264, GS-9820 ((S)-1-(4-((2-(2-aminopyrimidin-5-yl)-7-methyl-4-mohydroxypropan-1-one), GS-1101 (5-fluoro-3-phenyl-2-([S)]-1-[9H-purin-6-ylamino]-propyl)-3H-quinazolin-4-one), AMG-319, GSK-2269557, SAR245409 (N-(4-(N-(3-((3,5-dimethoxyphenyl)amino)quinoxalin-2-yl)sulfamoyl)phenyl)-3-methoxy-4 methylbenzamide), BAY80-6946 (2-amino-N-(7-methoxy-8-(3-morpholinopropoxy)-2,3-dihydroimidazo[1,2-c]quinaz), AS 252424 (5-[1-[5-(4-Fluoro-2-hydroxy-phenyl)-furan-2-yl]-meth-(Z)-ylidene]-thiazolidine-2,4-dione), CZ 24832 (5-(2-amino-8-fluoro-[1,2,4]triazolo[1,5-a]pyridin-6-yl)-N-tert-butylpyridine-3-sulfonamide), Buparlisib (5-[2,6-Di(4-morpholinyl)-4-pyrimidinyl]-4-(trifluoromethyl)-2-pyridinamine), GDC-0941 (2-(1H-Indazol-4-yl)-6-[[4-(methylsulfonyl)-1-piperazinyl]methyl]-4-(4-morpholinyl)thieno[3,2-d]pyrimidine), GDC-0980 ((S)-1-(4-((2-(2-aminopyrimidin-5-yl)-7-methyl-4-morpholinothieno[3,2-d]pyrimidin-6 yl)methyl)piperazin-1-yl)-2-hydroxypropan-1-one (also known as RG7422)), SF1126 ((8S,14S,17S)-14-(carboxymethyl)-8-(3-guanidinopropyl)-17-(hydroxymethyl)-3,6,9,12,15-pentaoxo-1-(4-(4-oxo-8-phenyl-4H-chromen-2-yl)morpholino-4-ium)-2-oxa-7,10,13,16-tetraazaoctadecan-18-oate), PF-05212384 (N-[4-[[4-(Dimethylamino)-1-piperidinyl]carbonyl]phenyl]-N-[4-(4,6-di-4-morpholinyl-1,3,5-triazin-2-yl)phenyl]urea) (gedatolisib), LY3023414, BEZ235 (2-Methyl-2-{4-[3-methyl-2-oxo-8-(quinolin-3-yl)-2,3-dihydro-1H-imidazo[4,5-c]quinolin-1-yl]phenyl}propanenitrile) (dactolisib), XL-765 (N-(3-(N-(3-(3,5-dimethoxyphenylamino)quinoxalin-2-yl)sulfamoyl)phenyl)-3-methoxy-4-methylbenzamide), and GSK1059615 (5-[[4-(4-Pyridinyl)-6-quinolinyl]methylene]-2,4-thiazolidenedione), PX886 ([(3aR,6E,9S,9aR,10R,11aS)-6-[[bis(prop-2-enyl)amino]methylidene]-5-hydroxy-9-(methoxymethyl)-9a,11a-dimethyl-1,4,7-trioxo-2,3,3a,9,10,11-hexahydroindeno[4,5h]isochromen-10-yl] acetate (also known as sonolisib)), LY294002, AZD8186, PF-4989216, pilaralisib, GNE-317, PI-3065, PI-103, NU7441 (KU-57788), HS 173, VS-5584 (SB2343), CZC24832, TG100-115, A66, YM201636, CAY10505, PIK-75, PIK-93, AS-605240, BGT226 (NVP-BGT226), AZD6482, voxtalisib, alpelisib, IC-87114, TGI100713, CH5132799, PKI-402, copanlisib (BAY 80-6946), XL147, PIK-90, PIK-293, PIK-294, 3-MA (3-methyladenine), AS-252424, AS-604850, apitolisib (GDC-0980; RG7422), and the structure described in WO2014/071109 having the formula:

Compound 292

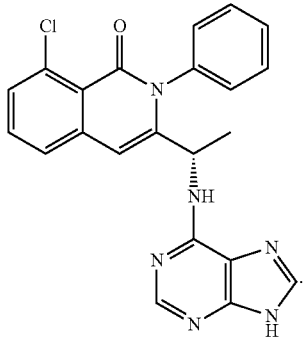

BTK inhibitors for use in the present invention are well known. Examples of BTK inhibitors include ibrutinib (also known as PCI-32765)(Imbmvica™)(1-[(3R)-3-[4-amino-3-(4-phenoxy-phenyl)pyrazolo[3,4-d]pyrimidin-1-yl]piperidin-1-yl]prop-2-en-1-one), dianilinopyrimidine-based inhibitors such as AVL-101 and AVL-291/292 (N-(3-((5-fluoro-2-((4-(2-methoxyethoxy)phenyl)amino)pyrimidin-4-yl)amino)phenyl)acrylamide) (Avila Therapeutics) (US Patent publication No 2011/0117073, incorporated herein in its entirety), Dasatinib ([N-(2-chloro-6-methylphenyl)-2-(6-(4-(2-hydroxyethyl)piperazin-1-yl)-2-methylpyrimidin-4-ylamino)thiazole-5-carboxamide], LFM-A13 (alpha-cyano-beta-hydroxy-beta-methyl-N-(2,5-ibromophenyl) propenamide), GDC-0834 ([R—N-(3-(6-(4-(1,4-dimethyl-3-oxopiperazin-2-yl)phenylamino)-4-methyl-5-oxo-4,5-dihydropyrazin-2-yl)-2-methylphenyl)-4,5,6,7-tetrahydrobenzo[b]thiophene-2-carboxamide], CGI-560 4-(tert-butyl)-N-(3-(8-(phenylamino)imidazo[1,2-a]pyrazin-6-yl) phenyl)benzamide, CGI-1746 (4-(tert-butyl)-N-(2-methyl-3-(4-methyl-6-((4-(morpholine-4-carbonyl)phenyl)amino)-5-oxo-4,5-dihydropyrazin-2-yl)phenyl)benzamide), CNX-774 (4-(4-((4-((3-acrylamidophenyl)amino)-5-fluoropyrimidin-2-yl)amino)phenoxy)-N-methylpicolinamide), CTA056 (7-benzyl-1-(3-(piperidin-1-yl)propyl)-2-(4-(pyridin-4-yl)phenyl)-1H-imidazo[4,5-g] quinoxalin-6(5H)-one), GDC-0834 ((R)—N-(3-(6-((4-(1,4-dimethyl-3-oxopiperazin-2-yl)phenyl)amino)-4-methyl-5-oxo-4,5-dihydropyrazin-2-yl)-2-methylphenyl)-4,5,6,7-tetrahydrobenzo[b]thiophene-2-carboxamide), GDC-0837 ((R)—N-(3-(6-((4-(1,4-dimethyl-3-oxopiperazin-2-yl)phenyl)amino)-4-methyl-5-oxo-4,5-dihydropyrazin-2-yl)-2-methylphenyl)-4,5,6,7-tetrahydrobenzo[b]thiophene-2-carboxamide), HM-71224, ACP-196, ONO-4059 (Ono Pharmaceuticals), PRT062607 (4-((3-(2H-1,2,3-triazol-2-yl)phenyl)amino)-2-(((1R,2S)-2-aminocyclohexyl)amino) pyrimidine-5-carboxamide hydrochloride), QL-47 (1-(1-acryloylindolin-6-yl)-9-(1-methyl-1H-pyrazol-4-yl)benzo[h][1,6]naphthyridin-2(1H)-one), and RN486 (6-cyclopropyl-8-fluoro-2-(2-hydroxymethyl-3-{1-methyl-5-[5-(4-methyl-piperazin-1-yl)-pyridin-2-ylamino]-6-oxo-1,6-dihydro-pyridin-3-yl}-phenyl)-2H-isoquinolin-1-one), and other molecules capable of inhibiting BTK activity, for example those BTK inhibitors disclosed in Akinleye et al, Journal of Hematology & Oncology, 2013, 6:59, the entirety of which is incorporated herein by reference.

Syk inhibitors for use in the present invention are well known, and include, for example, Cerdulatinib (4-(cyclopropylamino)-2-((4-(4-(ethylsulfonyl)piperazin-1-yl)phenyl)amino)pyrimidine-5-carboxamide), entospletinib (6-(1H-indazol-6-yl)-N-(4-morpholinophenyl)imidazo[1,2-a] pyrazin-8-amine), fostamatinib ([6-({5-Fluoro-2-[(3,4,5-trimethoxyphenyl)amino]-4-pyrimidinyl}amino)-2,2-dimethyl-3-oxo-2,3-dihydro-4H-pyrido[3,2-b][1,4]oxazin-4-yl]methyl dihydrogen phosphate), fostamatinib disodium salt (sodium (6-((5-fluoro-2-((3,4,5-trimethoxyphenyl) amino)pyrimidin-4-yl)amino)-2,2-dimethyl-3-oxo-2H-pyrido[3,2-b][1,4]oxazin-4(3H)-yl)methyl phosphate), BAY 61-3606 (2-(7-(3,4-Dimethoxyphenyl)-imidazo[1,2-c]pyrimidin-5-ylamino)-nicotinamide HCl), RO9021 (6-[(1R, 2S)-2-Amino-cyclohexylamino]-4-(5,6-dimethyl-pyridin-2-ylamino)-pyridazine-3-carboxylic acid amide), imatinib (Gleevac; 4-[(4-methylpiperazin-1-yl)methyl]-N-(4-methyl-3-{[4-(pyridin-3-yl)pyrimidin-2-yl]amino}phenyl)benzamide), staurosporine, GSK143 (2-(((3R,4R)-3-aminotetrahydro-2H-pyran-4-yl)amino)-4-(p-tolylamino)pyrimidine-5-carboxamide), PP2 (1-(tert-butyl)-3-(4-chlorophenyl)-1H-pyrazolo[3,4-d]pyrimidin-4-amine), PRT-060318 (2-(((1R, 2S)-2-aminocyclohexyl)amino)-4-(m-tolylamino) pyrimidine-5-carboxamide), PRT-062607 (4-((3-(2H-1,2,3-triazol-2-yl)phenyl)amino)-2-(((1R,2S)-2-aminocyclohexyl)amino)pyrimidine-5-carboxamide hydrochloride), R112 (3,3'-((5-fluoropyrimidine-2,4-diyl) bis(azanediyl))diphenol), R348 (3-Ethyl-4-methylpyridine), R406 (6-((5-fluoro-2-((3,4,5-trimethoxyphenyl)amino)pyrimidin-4-yl)amino)-2,2-dimethyl-2H-pyrido[3,2-b][1,4] oxazin-3(4H)-one), piceatannol (3-Hydroxyresveratol), YM193306 (Singh et al. Discovery and Development of Spleen Tyrosine Kinase (SYK) Inhibitors, J. Med. Chem. 2012, 55, 3614-3643), 7-azaindole, piceatannol, ER-27319 (Singh et al. Discovery and Development of Spleen Tyrosine Kinase (SYK) Inhibitors, J. Med. Chem. 2012, 55, 3614-3643 incorporated in its entirety herein), Compound D (Singh et al. Discovery and Development of Spleen Tyrosine Kinase (SYK) Inhibitors, J. Med. Chem. 2012, 55, 3614-3643 incorporated in its entirety herein), PRT060318 (Singh et al. Discovery and Development of Spleen Tyrosine Kinase (SYK) Inhibitors, J. Med. Chem. 2012, 55, 3614-3643 incorporated in its entirety herein), luteolin (Singh et al. Discovery and Development of Spleen Tyrosine Kinase (SYK) Inhibitors, J. Med. Chem. 2012, 55, 3614-3643 incorporated in its entirety herein), apigenin (Singh et al. Discovery and Development of Spleen Tyrosine Kinase (SYK) Inhibitors, J. Med. Chem. 2012, 55, 3614-3643 incorporated in its entirety herein), quercetin (Singh et al. Discovery and Development of Spleen Tyrosine Kinase (SYK) Inhibitors, J. Med. Chem. 2012, 55, 3614-3643 incorporated in its entirety herein), fisetin (Singh et al. Discovery and Development of Spleen Tyrosine Kinase (SYK) Inhibitors, J. Med. Chem. 2012, 55, 3614-3643 incorporated in its entirety herein), myricetin (Singh et al. Discovery and Development of Spleen Tyrosine Kinase (SYK) Inhibitors, J. Med. Chem. 2012, 55, 3614-3643 incorporated in its entirety herein), morin (Singh et al. Discovery and Development of Spleen Tyrosine Kinase (SYK) Inhibitors, J. Med. Chem. 2012, 55, 3614-3643 incorporated in its entirety herein).

In one embodiment, the therapeutic agent is a MEK inhibitor. MEK inhibitors for use in the present invention are well known, and include, for example, trametinib/GSK1120212 (N-(3-{3-Cyclopropyl-5-[(2-fluoro-4-iodophenyl)amino]-6,8-dimethyl-2,4,7-trioxo-3,4,6,7-tetrahydropyrido[4,3-d]pyrimidin-1(2H-yl}phenyl)acetamide), selumetinib (6-(4-bromo-2-chloroanilino)-7-fluoro-N-(2-hydroxyethoxy)-3-methylbenzimidazole-5-carboxamide), pimasertib/AS703026/MSC 1935369 ((S)—N-(2,3-dihydroxypropyl)-3-((2-fluoro-4-iodophenyl)amino)isonicotinamide), XL-518/GDC-0973 (1-({3,4-difluoro-2-[(2-fluoro-4-iodophenyl)amino]phenyl}carbonyl)-3-[(2S)-piperidin-2-yl]azetidin-3-ol), refametinib/BAY869766/RDEA1 19 (N-(3,4-difluoro-2-(2-fluoro-4-iodophenylamino)-6-methoxyphenyl)-1-(2,3-dihydroxypropyl)cyclopropane-1-sulfonamide), PD-0325901 (N-[(2R)-2,3-Dihydroxypropoxy]-3,4-difluoro-2-[(2-fluoro-4-iodophenyl)amino]-benzamide), TAK733 ((R)-3-(2,3-Dihydroxypropyl)-6-fluoro-5-(2-fluoro-4-iodophenylamino)-8-methylpyrido[2,3-d]pyrimidine-4,7 (3H,8H)-dione), MEK162/ARRY438162 (5-[(4-Bromo-2-fluorophenyl)amino]-4-fluoro-N-(2-hydroxyethoxy)-1-methyl-1H-benzimidazole-6-carboxamide), R05126766 (3-[[3-Fluoro-2-(methyl sulfamoylamino)-4-pyridyl]methyl]-4-methyl-7-pyrimidin-2-yloxychromen-2-one), WX-554, R04987655/CH4987655 (3,4-difluoro-2-((2-fluoro-4-iodophenyl)amino)-N-(2-hydroxyethoxy)-5-((3-oxo-1,2-oxazinan-2yl)methyl)benzamide), or AZD8330 (2-((2-fluoro-4-iodophenyl)amino)-N-(2 hydroxyethoxy)-1,5-dimethyl-6-oxo-1,6-dihydropyridine-3-carboxamide), U0126-EtOH, PD184352 (CI-1040), GDC-0623, BI-847325, cobimetinib, PD98059, BIX 02189, BIX 02188, binimetinib, SL-327, TAK-733, PD318088, and additional MEK inhibitors as described below.

In one embodiment, the therapeutic agent is a Raf inhibitor. Raf inhibitors for use in the present invention are well known, and include, for example, Vemurafinib (N-[3-[[5-(4-Chlorophenyl)-1H-pyrrolo[2,3-b]pyridin-3-yl]carbonyl]-2,4-difluorophenyl]-1-propanesulfonamide), sorafenib tosylate (4-[4-[[4-chloro-3-(trifluoromethyl)phenyl]carbamoylamino]phenoxy]-N-methylpyridine-2-carboxamide; 4-methylbenzenesulfonate), AZ628 (3-(2-cyanopropan-2-yl)-N-(4-methyl-3-(3-methyl-4-oxo-3,4-dihydroquinazolin-6-ylamino)phenyl)benzamide), NVP-BHG712 (4-methyl-3-(1-methyl-6-(pyridin-3-yl)-1H-pyrazolo[3,4-d]pyrimidin-4-ylamino)-N-(3-(trifluoromethyl)phenyl)benzamide), RAF-265 (1-methyl-5-[2-[5-(trifluoromethyl)-1H-imidazol-2-yl]pyridin-4-yl]oxy-N-[4-(trifluoromethyl)phenyl]benzimidazol-2-amine), 2-Bromoaldisine (2-Bromo-6,7-dihydro-1H,5H-pyrrolo[2,3-c]azepine-4,8-dione), Raf Kinase Inhibitor IV (2-chloro-5-(2-phenyl-5-(pyridin-4-yl)-1H-imidazol-4-yl)phenol), Sorafenib N-Oxide (4-[4-[[[[4-Chloro-3 (trifluoroMethyl)phenyl]aMino]carbonyl]aMino]phenoxy]-N-Methyl-2pyridinecarboxaMide 1-Oxide), PLX-4720, dabrafenib (GSK2118436), GDC-0879, RAF265, AZ 628, SB590885, ZM336372, GW5074, TAK-632, CEP-32496, LY3009120, and GX818 (Encorafenib).

In one embodiment, the therapeutic agent is a programmed death protein 1 (PD-1) inhibitor, a programmed death protein ligand 1 (PDL1) inhibitor, or a programmed death protein ligand 2 (PDL2) inhibitor. PD-1, PDL1, and PDL2 inhibitors are known in the art, and include, for example, nivolumab (BMS), pembrolizumab (Merck), pidilizumab (CureTech/Teva), AMP-244 (Amplimmune/GSK), BMS-936559 (BMS), and MEDI4736 (Roche/Genentech), and MPDL3280A (Genentech).

In one embodiment, a therapeutic agent can be administered in a sustained fashion.

In one embodiment, the therapeutic agent is a monoclonal antibody (MAb). Some MAbs stimulate an immune response that destroys cancer cells. Similar to the antibodies produced naturally by B cells, these MAbs "coat" the cancer cell surface, triggering its destruction by the immune system. For example, bevacizumab targets vascular endothelial growth factor (VEGF), a protein secreted by tumor cells and other cells in the tumor's microenvironment that promotes the development of tumor blood vessels. When bound to bevacizumab, VEGF cannot interact with its cellular receptor, preventing the signaling that leads to the growth of new blood vessels. Similarly, cetuximab and panitumumab target the epidermal growth factor receptor (EGFR), and trastuzumab targets the human epidermal growth factor receptor 2 (HER-2). MAbs that bind to cell surface growth factor receptors prevent the targeted receptors from sending their normal growth-promoting signals. They may also trigger apoptosis and activate the immune system to destroy tumor cells.

Other agents may include, but are not limited to, at least one of tamoxifen, midazolam, letrozole, bortezomib, anastrozole, goserelin, an mTOR inhibitor, a PI3 kinase inhibitor as described above, a dual mTOR-PI3K inhibitor, a MEK inhibitor, a RAS inhibitor, ALK inhibitor, an HSP inhibitor (for example, HSP70 and HSP 90 inhibitor, or a combination thereof), a BCL-2 inhibitor as described above, apopototic inducing compounds, an AKT inhibitor, including but not limited to, MK-2206, GSK690693, Perifosine, (KRX-0401), GDC-0068, Triciribine, AZD5363, Honokiol, PF-04691502, and Miltefosine, a PD-1 inhibitor as described above including but not limited to, Nivolumab, CT-011, MK-3475, BMS936558, and AMP-514 or a FLT-3 inhibitor, including but not limited to, P406, Dovitinib, Quizartinib (AC220), Amuvatinib (MP-470), Tandutinib (MLN518), ENMD-2076, and KW-2449, or a combination thereof. Examples of mTOR inhibitors include but are not limited to rapamycin and its analogs, everolimus (Afinitor), temsirolimus, ridaforolimus, sirolimus, and deforolimus. Examples of MEK inhibitors include but are not limited to tametinib/GSK1120212 (N-(3-{3-Cyclopropyl-5-[(2-fluoro-4-iodophenyl)amino]-6,8-dimethyl-2,4,7-trioxo-3,4,6,7-tetrahydropyrido[4,3-d]pyrimidin-1(2H-yl}phenyl)acetamide), selumetinob (6-(4-bromo-2-chloroanilino)-7-fluoro-N-(2-hydroxyethoxy)-3-methylbenzimidazole-5-carboxamide), pimasertib/AS703026/MSC1935369 ((S)—N-(2,3-dihydroxypropyl)-3-((2-fluoro-4-iodophenyl)amino)isonicotinamide), XL-518/GDC-0973 (1-({3,4-difluoro-2-[(2-fluoro-4-iodophenyl)amino]phenyl}carbonyl)-3-[(2S)-piperidin-2-yl]azetidin-3-ol) (cobimetinib), refametinib/BAY869766/RDEAl19 (N-(3,4-difluoro-2-(2-fluoro-4-iodophenylamino)-6-methoxyphenyl)-1-(2,3-dihydroxypropyl)cyclopropane-1-sulfonamide), PD-0325901 (N-[(2R)-2,3-Dihydroxypropoxy]-3,4-difluoro-2-[(2-fluoro-4-iodophenyl)amino]-benzamide), TAK733 ((R)-3-(2,3-Dihydroxypropyl)-6-fluoro-5-(2-fluoro-4-iodophenylamino)-8-methylpyrido[2,3d]pyrimidine-4,7(3H,8H)-dione), MEK162/ARRY438162 (5-[(4-Bromo-2-fluorophenyl)amino]-4-fluoro-N-(2-hydroxyethoxy)-1-methyl-1H-benzimidazole-6 carboxamide), R05126766 (3-[[3-Fluoro-2-(methylsulfamoylamino)-4-pyridyl]methyl]-4-methyl-7-pyrimidin-2-yloxychromen-2-one), WX-554, R04987655/CH4987655 (3,4-difluoro-2-((2-fluoro-4-iodophenyl)amino)-N-(2-hydroxyethoxy)-5-((3-oxo-1,2-oxazinan-2 yl)methyl)benzamide), or AZD8330 (2-((2-fluoro-4-iodophenyl)amino)-N-(2-hydroxyethoxy)-1,5-dimethyl-6-oxo-1,6-dihydropyridine-3-carboxamide). Examples of RAS inhibitors include but are not limited to Reolysin and siG12D LODER. Examples of ALK inhibitors include but are not limited to Crizotinib, Ceritinib (Zykadia), AP26113, and LDK378. HSP inhibitors include but are not limited to Geldanamycin or 17-N-Allylamino-17-demethoxygeldanamycin (17AAG), and Radicicol.

In certain aspects, the therapeutic agent is an anti-inflammatory agent, a chemotherapeutic agent, a radiotherapeutic, an additional therapeutic agent, or an immunosuppressive agent.

In one embodiment, a chemotherapeutic is selected from, but not limited to, imatinib mesylate (Gleevac®), dasatinib (Sprycel®), nilotinib (Tasigna®), bosutinib (Bosulif®), trastuzumab (Herceptin®), trastuzumab-DM1, pertuzumab (Perjeta™), lapatinib (Tykerb®), gefitinib (Iressa®), erlotinib (Tarceva®), cetuximab (Erbitux®), panitumumab (Vectibix®), vandetanib (Caprelsa®), vemurafenib (Zelboraf®), vorinostat (Zolinza®), romidepsin (Istodax®), bexarotene (Tagretin®), alitretinoin (Panretin®), tretinoin (Vesanoid®), carfilizomib (Kyprolis™), pralatrexate (Folotyn®), bevacizumab (Avastin®), ziv-aflibercept (Zaltrap®), sorafenib (Nexavar®), sunitinib (Sutent®), pazopanib (Votrient®), regorafenib (Stivarga®), and cabozantinib (Cometriq™).

Additional chemotherapeutic agents include, but are not limited to, a radioactive molecule, a toxin, also referred to as cytotoxin or cytotoxic agent, which includes any agent that is detrimental to the viability of cells, and liposomes or other vesicles containing chemotherapeutic compounds. General anticancer pharmaceutical agents include: vincristine (Oncovin®) or liposomal vincristine (Marqibo®), daunorubicin (daunomycin or Cerubidine®) or doxorubicin (Adriamycin®), cytarabine (cytosine arabinoside, ara-C, or Cytosar®), L-asparaginase (Elspar®) or PEG-L-asparaginase (pegaspargase or Oncaspar®), etoposide (VP-16), teniposide (Vumon®), 6-mercaptopurine (6-MP or Purinethol®), Methotrexate, cyclophosphamide (Cytoxan®), Prednisone, dexamethasone (Decadron), imatinib (Gleevec®), dasatinib (Sprycel®), nilotinib (Tasigna®), bosutinib (Bosulif®), and ponatinib (Iclusig™). Examples of additional suitable chemotherapeutic agents include but are not limited to 1-dehydrotestosterone, 5-fluorouracil decarbazine, 6-mercaptopurine, 6-thioguanine, actinomycin D, adriamycin, aldesleukin, an alkylating agent, allopurinol sodium, altretamine, amifostine, anastrozole, anthramycin (AMC)), an anti-mitotic agent, cis-dichlorodiamine platinum (II) (DDP) cisplatin), diamino dichloro platinum, anthracycline, an antibiotic, an antimetabolite, asparaginase, BCG live (intravesical), betamethasone sodium phosphate and betamethasone acetate, bicalutamide, bleomycin sulfate, busulfan, calcium leucouorin, calicheamicin, capecitabine, carboplatin, lomustine (CCNU), carmustine (BSNU), chlorambucil, cisplatin, cladribine, colchicin, conjugated estrogens, cyclophosphamide, cyclothosphamide, cytarabine, cytarabine, cytochalasin B, cytoxan, dacarbazine, dactinomycin, dactinomycin (formerly actinomycin), daunirubicin HCL, daunorucbicin citrate, denileukin diftitox, Dexrazoxane, Dibromomannitol, dihydroxy anthracin dione, docetaxel, dolasetron mesylate, doxorubicin HCL, dronabinol, E. coli L-asparaginase, emetine, epoetin-α, Erwinia L-asparaginase, esterified estrogens, estradiol, estramustine phosphate sodium, ethidium bromide, ethinyl estradiol, etidronate, etoposide citrororum factor, etoposide phosphate, filgrastim, floxuridine, fluconazole, fludarabine phosphate, fluorouracil, flutamide, folinic acid, gemcitabine HCL, glucocorticoids, goserelin acetate, gramicidin D, granisetron HCL, hydroxyurea, idarubicin HCL, ifosfamide, interferon α-2b, irinotecan HCL, letrozole, leucovorin calcium, leuprolide acetate, levamisole HCL, lidocaine, lomustine, maytansinoid, mechlorethamine HCL, medroxyprogesterone acetate, megestrol acetate, melphalan HCL, mercaptipurine, mesna, methotrexate, methyltestosterone, mithramycin, mitomycin C, mitotane, mitoxantrone, nilutamide, octreotide acetate, ondansetron HCL, paclitaxel, pamidronate disodium, pentostatin, pilocarpine HCL, plimycin, polifeprosan 20 with carmustine implant, porfimer sodium, procaine, procarbazine HCL, propranolol, rituximab, sargramostim, streptozotocin, tamoxifen, taxol, teniposide, tenoposide, testolactone, tetracaine, thioepa chlorambucil, thioguanine, thiotepa, topotecan HCL, toremifene citrate, trastuzumab, tretinoin, valrubicin, vinblastine sulfate, vincristine sulfate, and vinorelbine tartrate.

Additional therapeutic agents can include bevacizumab, sutinib, sorafenib, 2-methoxyestradiol or 2ME2, finasunate, vatalanib, vandetanib, aflibercept, volociximab, etaracizumab (MEDI-522), cilengitide, erlotinib, cetuximab, panitumumab, gefitinib, trastuzumab, dovitinib, figitumumab, atacicept, rituximab, alemtuzumab, aldesleukine, atlizumab, tocilizumab, temsirolimus, everolimus, lucatumumab, dacetuzumab, HLL1, huN901-DM1, atiprimod, natalizumab, bortezomib, carfilzomib, marizomib, tanespimycin, saquinavir mesylate, ritonavir, nelfinavir mesylate, indinavir sulfate, belinostat, panobinostat, mapatumumab, lexatumumab, dulanermin, ABT-737, oblimersen, plitidepsin, talmapimod, P276-00, enzastaurin, tipifarnib, perifosine, imatinib, dasatinib, lenalidomide, thalidomide, simvastatin, celecoxib, bazedoxifene, AZD4547, rilotumumab, oxaliplatin (Eloxatin), PD0332991 (palbociclib), ribociclib (LEE011), amebaciclib (LY2835219), HDM201, fulvestrant (Faslodex), exemestane (Aromasin), PIM447, ruxolitinib (INC424), BGJ398, necitumumab, pemetrexed (Alimta), and ramucirumab (IMC-1121B).

In one aspect of the present invention, an immunosuppressive agent is used, preferably selected from the group consisting of a calcineurin inhibitor, e.g. a cyclosporin or an ascomycin, e.g. Cyclosporin A (NEORAL®), FK506 (tacrolimus), pimecrolimus, a mTOR inhibitor, e.g. rapamycin or a derivative thereof, e.g. Sirolimus (RAPAMUNE®), Everolimus (Certican®), temsirolimus, zotarolimus, biolimus-7, biolimus-9, a rapalog, e.g.ridaforolimus, azathioprine, campath 1H, a S1P receptor modulator, e.g. fingolimod or an analogue thereof, an anti-IL-8 antibody, mycophenolic acid or a salt thereof, e.g. sodium salt, or a prodrug thereof, e.g. Mycophenolate Mofetil (CELLCEPT®), OKT3 (ORTHOCLONE OKT3®), Prednisone, ATGAM®, THYMOGLOBULIN®, Brequinar Sodium, OKT4, T10B9.A-3A, 33B3.1, 15-deoxyspergualin, tresperimus, Leflunomide ARAVA®, CTLAI-Ig, anti-CD25, anti-IL2R, Basiliximab (SIMULECT®), Daclizumab (ZENAPAX®), mizorbine, methotrexate, dexamethasone, ISAtx-247, SDZ ASM 981 (pimecrolimus, Elidel®), CTLA4lg (Abatacept), belatacept, LFA3lg, etanercept (sold as Enbrel® by Immunex), adalimumab (Humira®), infliximab (Remicade®), an anti-LFA-1 antibody, natalizumab (Antegren®), Enlimomab, gavilimomab, antithymocyte immunoglobulin, siplizumab, Alefacept efalizumab, pentasa, mesalazine, asacol, codeine phosphate, benorylate, fenbufen, naprosyn, diclofenac, etodolac and indomethacin, aspirin and ibuprofen.

Examples of types of therapeutic agents that can be include anti-inflammatory drugs, antimicrobial agents, antiangiogenesis agents, immunosuppressants, antibodies, steroids, ocular antihypertensive drugs and combinations thereof. Examples of therapeutic agents include amikacin, anecortane acetate, anthracenedione, anthracycline, an azole, amphotericin B, bevacizumab, camptothecin, cefuroxime, chloramphenicol, chlorhexidine, chlorhexidine digluconate, clortrimazole, a clotrimazole cephalosporin, corticosteroids, dexamethasone, desamethazone, econazole, eftazidime, epipodophyllotoxin, fluconazole, flucytosine, fluoropyrimidines, fluoroquinolines, gatifloxacin, glycopeptides, imidazoles, itraconazole, ivermectin, ketoconazole, levofloxacin, macrolides, miconazole, miconazole nitrate, moxifloxacin, natamycin, neomycin, nystatin, ofloxacin, polyhexamethylene biguanide, prednisolone, prednisolone acetate, pegaptanib, platinum analogues, polymicin B, propamidine isethionate, pyrimidine nucleoside, ranibizumab, squalamine lactate, sulfonamides, triamcinolone, triamcinolone acetonide, triazoles, vancomycin, anti-vascular endothelial growth factor (VEGF) agents, VEGF antibodies, VEGF antibody fragments, vinca alkaloid, timolol, betaxolol, travoprost, latanoprost, bimatoprost, brimonidine, dorzolamide, acetazolamide, pilocarpine, ciprofloxacin, azithromycin, gentamycin, tobramycin, cefazolin, voriconazole, gancyclovir, cidofovir, foscarnet, diclofenac, nepafenac, ketorolac, ibuprofen, indomethacin, fluorometholone, rimexolone, anecortave, cyclosporine, methotrexate, tacrolimus and combinations thereof.

Examples of immunosuppressive agents are calcineurin inhibitor, e.g., a cyclosporin or an ascomycin, e.g., Cyclosporin A (NEORAL®), FK506 (tacrolimus), pimecrolimus, a mTOR inhibitor, e.g., rapamycin or a derivative thereof, e.g., Sirolimus (RAPAMUNE®), Everolimus (Certican®), temsirolimus, zotarolimus, biolimus-7, biolimus-9, a rapalog, e.g., ridaforolimus, azathioprine, campath 1H, a S1P receptor modulator, e.g., fingolimod or an analogue thereof, an anti IL-8 antibody, mycophenolic acid or a salt thereof, e.g., sodium salt, or a prodrug thereof, e.g., Mycophenolate Mofetil (CELLCEPT®), OKT3 (ORTHOCLONE OKT3®), Prednisone, ATGAM®, THYMOGLOBULIN®, Brequinar Sodium, OKT4, T10B9.A-3A, 33B3.1, 15-deoxyspergualin, tresperimus, Leflunomide ARAVA®, CTLAI-Ig, anti-CD25, anti-IL2R, Basiliximab (SIMULECT®), Daclizumab (ZENAPAX®), mizorbine, methotrexate, dexamethasone, ISAtx-247, SDZ ASM 981 (pimecrolimus, Elidel®), CTLA4lg (Abatacept), belatacept, LFA3lg, etanercept (sold as Enbrel® by Immunex), adalimumab (Humira®), infliximab (Remicade®), an anti-LFA-1 antibody, natalizumab (Antegren®), Enlimomab, gavilimomab, antithymocyte immunoglobulin, siplizumab, Alefacept efalizumab, pentasa, mesalazine, asacol, codeine phosphate, benorylate, fenbufen, naprosyn, diclofenac, etodolac and indomethacin, aspirin and ibuprofen.

An aspect of the invention is a method for the treatment of a disorder, comprising administering to a host in need thereof surface-modified solid aggregating microparticles comprising an effective amount of a therapeutic agent, wherein the therapeutic agent containing surface-modified solid aggregating microparticles are injected into the body and aggregate in vivo to form at least one pellet of at least 500 Lm that provides sustained drug delivery for at least one month.

V. Pharmaceutically Acceptable Carriers

Any suitable pharmaceutically acceptable carrier, for example, ophthalmically acceptable viscous carrier, may be employed in accordance with the invention. The carrier is present in an amount effective in providing the desired viscosity to the drug delivery system. Advantageously, the viscous carrier is present in an amount in a range of from about 0.5 wt percent to about 95 wt percent of the drug delivery particles. The specific amount of the viscous carrier used depends upon a number of factors including, for example and without limitation, the specific viscous carrier used, the molecular weight of the viscous carrier used, the viscosity desired for the present drug delivery system being produced and/or used and like factors. Examples of useful viscous carriers include, but are not limited to, hyaluronic acid, sodium hyaluronate, carbomers, polyacrylic acid, cellulosic derivatives, polycarbophil, polyvinylpyrrolidone, gelatin, dextrin, polysaccharides, polyacrylamide, polyvinyl alcohol (which can be partially hydrolyzed polyvinyl acetate), polyvinyl acetate, derivatives thereof and mixtures thereof.

The carrier can also be an aqueous carrier. Example of aqueous carriers include, but are not limited to, an aqueous solution or suspension, such as saline, plasma, bone marrow aspirate, buffers, such as Hank's Buffered Salt Solution (HBSS), HEPES (4-(2-hydroxyethyl)-1-piperazineethanesulfonic acid), Ringers buffer, ProVisc®, diluted ProVisc®, ProVisc® diluted with PBS, Krebs buffer, Dulbecco's PBS, normal PBS; sodium hyaluronate solution (HA, 5 mg/mL in PBS), simulated body fluids, plasma platelet concentrate and tissue culture medium or an aqueous solution or suspension comprising an organic solvent.

In one embodiment, the carrier is PBS.

In one embodiment, the carrier is HA, 5 mg/mL in PBS.

In one embodiment, the carrier is ProVisc® diluted with water.

In one embodiment, the carrier is ProVisc® dilution in PBS.

In one embodiment, the carrier is ProVisc® 5-fold diluted with water.

In one embodiment, the carrier is ProVisc® 5-fold dilution in PBS.

In one embodiment, the carrier is ProVisc® 10-fold diluted with water.

In one embodiment, the carrier is ProVisc® 10-fold dilution in PBS.

In one embodiment, the carrier is ProVisc® 20-fold dilution with water.

In one embodiment, the carrier is ProVisc® 20-fold dilution in PBS.

In one embodiment, the carrier is HA, 1.25 mg/mL in an isotonic buffer solution with neutral pH.

The carrier may, optionally, contain one or more suspending agent. The suspending agent may be selected from carboxy methylcellulose (CMC), mannitol, polysorbate, poly propylene glycol, poly ethylene glycol, gelatin, albumin, alginate, hydroxyl propyl methyl cellulose (HPMC), hydroxyl ethyl methyl cellulose (HEMC), bentonite, tragacanth, dextrin, sesame oil, almond oil, sucrose, acacia gum and xanthan gum and combinations thereof.

The carrier may, optionally, contain one or more plasticizers. Thus the carrier may also include a plasticizer. The plasticizer may, for example, be polyethylene glycol (PEG), polypropylene glycol, poly (lactic acid) or poly (glycolic acid) or a copolymer thereof, polycaprolactone, and low molecule weight oligomers of these polymers, or conventional plasticizers, such as, adipates, phosphates, phthalates, sabacates, azelates and citrates. The carrier can also include other known pharmaceutical excipients in order to improve the stability of the agent.

In one embodiment, one or more additional excipients or delivery enhancing agents may also be included e.g., surfactants and/or hydrogels, in order to further influence release rate.

VI. Sustained Release of Pharmaceutically Active Compound

The rate of release of the pharmaceutically active compound can be related to the concentration of pharmaceutically active compound dissolved in the surface treated microparticle. In some embodiments, the polymeric composition of the surface treated microparticle includes non-therapeutic agents that are selected to provide a desired solubility of the pharmaceutically active compound. The selection of the polymeric composition can be made to provide the desired solubility of the pharmaceutically active compound in the surface treated microparticle, for example, a hydrogel may promote solubility of a hydrophilic material. In some embodiments, functional groups can be added to the polymer to increase the desired solubility of the pharmaceutically active compound in the surface treated microparticle. In some embodiments, additives may be used to control the release kinetics of the pharmaceutically active compound, for example, the additives may be used to control the concentration of the pharmaceutically active compound by increasing or decreasing the solubility of the pharmaceutically active compound in the polymer so as to control the release kinetics of the pharmaceutically active compound. The solubility may be controlled by including appropriate molecules and/or substances that increase and/or decrease the solubility of the dissolved form of the pharmaceutically active compound in the surface treated microparticle. The solubility of the pharmaceutically active compound may be related to the hydrophobic and/or hydrophilic properties of the surface treated microparticle and the pharmaceutically active compound. Oils and hydrophobic molecules can be added to the polymer(s) to increase the solubility of a pharmaceutically active compound in the surface treated microparticle.

Instead of, or in addition to, controlling the rate of migration based on the concentration of the pharmaceutically active compound dissolved in the surface treated microparticle, the surface area of the polymeric composition can be controlled to attain the desired rate of drug migration out of the surface treated microparticle comprising a pharmaceutically active compound. For example, a larger exposed surface area will increase the rate of migration of the pharmaceutically active compound to the surface, and a smaller exposed surface area will decrease the rate of migration of the pharmaceutically active compound to the surface. The exposed surface area can be increased in any number of ways, for example, by any of castellation of the exposed surface, a porous surface having exposed channels connected with the tear or tear film, indentation of the exposed surface, or protrusion of the exposed surface. The exposed surface can be made porous by the addition of salts that dissolve and leave a porous cavity once the salt dissolves. In the present invention, these trends can be used to decrease the release rate of the active material from the polymeric composition by avoiding these paths to quicker release. For example, the surface area can be minimized, or channels can be avoided.

Where more than one type of polymer is used, each surface treated microparticle may have a different solidifying or setting property. For example, the surface treated microparticles may be made from similar polymers but may have different gelling pHs or different melting temperatures or glass transition points.

In order for the surface treated microparticles to form a consolidated aggregate, the temperature around the particles, for example in the human or non-human animal where the composition is administered, is approximately equal to, or greater than, the glass transition temperature ($T_g$) of the polymer particles. At such temperatures the polymer particles will cross-link to one or more other polymer particles to form a consolidated aggregate. By cross-link it is meant that adjacent polymer particles become joined together. For example, the particles may cross-link due to entanglement of the polymer chains at the surface of one particle with polymer chains at the surface of another particle. There may be adhesion, cohesion or fusion between adjacent particles.

Typically, the injectable surface treated microparticles which are formed of a polymer or a polymer blend have a glass transition temperature ($T_g$) either close to or just above body temperature (such as from about 30° C. to 45° C., e.g., from about 35° C. to 40° C., for example, from about 37° C. to 40° C.). Accordingly, at room temperature the surface treated microparticles are below their $T_g$ and behave as discrete particles, but in the body the surface treated microparticles soften and interact/stick to themselves. Typically, agglomeration begins within 20 seconds to about 15 minutes of the raise in temperature from room to body temperature.

The surface treated microparticles may be formed from a polymer which has a $T_g$ from about 35° C. to 40° C., for example from about 37° C. to 40° C., wherein the polymer is a poly(α-hydroxyacid) (such as PLA, PGA, PLGA, or PDLLA or a combination thereof), or a blend thereof with PLGA-PEG. Typically, these particles will agglomerate at body temperature. The injectable surface treated microparticles may comprise only poly(α-hydroxyacid) particles or other particle types may be included. The microparticles can be formed from a blend of poly(D,L-lactide-co-glycolide) (PLGA), PLGA-PEG and PVA which has a $T_g$ at or above body temperature. In one embodiment, at body temperature the surface treated microparticles will interact to form a consolidated aggregate. The injectable microparticle may comprise only PLGA/PLGA-PEG/PVA surface treated microparticles or other particle types may be included.

The composition may comprise a mixture of temperature sensitive surface treated microparticles and non-temperature sensitive surface treated microparticles. Non-temperature sensitive surface treated microparticles are particles with a glass transition temperature which is above the temperature at which the composition is intended to be used. Typically, in a composition comprising a mixture of temperature sensitive surface treated microparticles and non-temperature sensitive particles the ratio of temperature sensitive to non-temperature sensitive surface treated microparticles is about 3:1, or lower, for example, 4:3. The temperature sensitive surface treated microparticles are advantageously capable of crosslinking to each other when the temperature of the composition is raised to or above the glass transition of these microparticles. By controlling the ratio of temperature sensitive surface treated microparticles to non-temperature sensitive surface treated microparticles it may be possible to manipulate the porosity of the resulting consolidated aggregate. The surface treated microparticles may be solid, that is with a solid outer surface, or they may be porous. The particles may be irregular or substantially spherical in shape.

The surface treated microparticles can have a size in their longest dimension, or their diameter if they are substantially spherical, of less than about 100 μm and more than about 1 μm. The surface treated microparticles can have a size in their longest dimension, or their diameter, of less than about 100 μm. The surface treated microparticles can have a size in their longest dimension, or their diameter, of between about 1 jam and about 40 jam, more typically, between about 20 jam and about 40 μm. Polymer particles of the desired size will pass through a sieve or filter with a pore size of about 40 μm.

Formation of the consolidated aggregate from the composition, once administered to a human or non-human animal, typically takes from about 20 seconds to about 24 hours, for example, between about 1 minute and about 5 hours, between about 1 minute and about 1 hour, less than about 30 minutes, less than about 20 minutes. Typically, the solidification occurs in between about 1 minute and about 20 minutes from administration.

Typically, the composition comprises from about 20 percent to about 80 percent injectable surface treated microparticle material and from about 20 percent to about 80 percent carrier; from about 30 percent to about 70 percent injectable surface treated microparticle material and from about 30 percent to about 70 percent carrier; e.g., the composition may comprise from about 40 percent to about 60 percent injectable surface treated microparticle material and from about 40 percent to about 60 percent carrier; the composition may comprise about 50 percent injectable surface treated microparticle material and about 50 percent carrier. The aforementioned percentages all refer to percentage by weight.

The surface treated microparticles are loaded, for example, in the surface treated microparticle or as a coating on the surface treated microparticle, with a pharmaceutically active compound.

The system of the invention can allow for the pharmaceutically active compound release to be sustained for some time, for example, release can be sustained for at least about 2 hours, at least about 4 hours, at least about 6 hours, at least about 10 hours, at least about 12 hours, at least about 24 hours, at least 48 hours, at least a week, more than one week, at least a month, at least two months, at least three months, at least four months, at least five months, at least six months, or at least seven months.

In one embodiment, the surface-modified solid aggregating microparticles that produce a pellet in vivo release the therapeutic agent without a burst of more than about 1 percent to about 5 percent of total payload over a 24 hour period.

In one embodiment, the surface-modified solid aggregating microparticles that produce a pellet in vivo release the therapeutic agent without a burst of more than about 10 percent of total payload over a 24 hour period.

In one embodiment, the surface-modified solid aggregating microparticles that produce a pellet in vivo release the therapeutic agent without a burst of more than about 15 percent of total payload over a 24 hour period.

In one embodiment, the surface-modified solid aggregating microparticles that produce a pellet in vivo release the therapeutic agent without a burst of more than about 20 percent of total payload over a 24 hour period.

In one embodiment, the surface-modified solid aggregating microparticles that produce a pellet in vivo release the therapeutic agent without a burst of more than about 1 percent to about 5 percent of total payload over a 12 hour period.

In one embodiment, the surface-modified solid aggregating microparticles that produce a pellet in vivo release the therapeutic agent without a burst of more than about 10 percent of total payload over a 12 hour period.

In one embodiment, the surface-modified solid aggregating microparticles that produce a pellet in vivo release the therapeutic agent without a burst of more than about 15 percent of total payload over a 12 hour period.

In one embodiment, the surface-modified solid aggregating microparticles that produce a pellet in vivo release the therapeutic agent without a burst of more than about 15 percent of total payload over a 12 hour period.

In one embodiment, the pharmaceutically active compound is released in an amount effective to have a desired local or systemic physiological or pharmacologically effect.

In one embodiment, delivery of a pharmaceutically active compound means that the pharmaceutically active compound is released from the consolidated aggregate into the environment around the consolidated aggregate, for example, the vitreal fluid.

In one embodiment, a surface treated microparticle comprising a pharmaceutically active compound of the invention allows a substantially zero or first order release rate of the pharmaceutically active compound from the consolidated aggregate once the consolidated aggregate has formed. A zero order release rate is a constant release of the pharmaceutically active compound over a defined time; such release is difficult to achieve using known delivery methods.

VII. Manufacture of Surface Treated Microparticles

Microparticle Formation

Microparticles can be formed using any suitable method for the formation of polymer microparticles known in the art. The method employed for particle formation will depend on a variety of factors, including the characteristics of the polymers present in the drug or polymer matrix, as well as the desired particle size and size distribution. The type of drug(s) being incorporated in the microparticles may also be a factor as some drugs are unstable in the presence of certain solvents, in certain temperature ranges, and/or in certain pH ranges.

Particles having an average particle size of between 1 micron and 100 microns are useful in the compositions described herein. In typical embodiments, the particles have an average particle size of between 1 micron and 40 microns, more typically between about 10 micron and about 40 microns, more typically between about 20 micron and about 40 microns. The particles can have any shape but are generally spherical in shape.

In circumstances where a monodisperse population of particles is desired, the particles may be formed using a method which produces a monodisperse population of microparticles.

Alternatively, methods producing polydispersed microparticle distributions can be used, and the particles can be separated using methods known in the art, such as sieving, following particle formation to provide a population of particles having the desired average particle size and particle size distribution.

Common techniques for preparing microparticles include, but are not limited to, solvent evaporation, hot melt particle formation, solvent removal, spray drying, phase inversion, coacervation, and low temperature casting. Suitable methods of particle formulation are briefly described below. Pharmaceutically acceptable excipients, including pH modifying agents, disintegrants, preservatives, and antioxidants, can optionally be incorporated into the particles during particle formation.

In one embodiment, surface treated microparticles are prepared using continuous chemistry manufacturing processes. In one embodiment, surface treated microparticles are prepared using step-wise manufacturing processes.

In one embodiment, microparticles containing a therapeutic agent can be prepared as described in PCT/US2015/065894. In one embodiment, the microparticles are prepared by:

(i) dissolving or dispersing the therapeutic agent or its salt in an organic solvent optionally with an alkaline agent;

(ii) mixing the solution/dispersion of step (i) with a polymer solution that has a viscosity of at least about 300 cPs (or perhaps at least about 350, 400, 500, 600, 700 or 800 or more cPs);

(iii) mixing the therapeutic agent polymer solution/dispersion of step (ii) with an aqueous non-acidic or alkaline solution (for example at least approximately a pH of 7, 8, or 9 and typically not higher than about 10) optionally with a surfactant or emulsifier, to form a solvent-laden therapeutic agent encapsulated microparticle, (iv) isolating the microparticles.

In one embodiment, the therapeutic agent is sunitinib.

It has been found that it may be useful to include the alkaline agent in the organic solvent. However, as described in PCT/US2015/065894, it has been found that adding an acid to the organic solvent can improve drug loading of the microparticle. Examples demonstrate that polyesters such as PLGA, PEG-PLGA (PLA) and PEG-PLGA/PLGA blend microparticles display sustained release of the therapeutic agent or its pharmaceutically acceptable salt. Polymer microparticles composed of PLGA and PEG covalently conjugated to PLGA (Mw 45 kDa) (PLGA45k-PEG5k) loaded with the therapeutic agent were prepared using a single emulsion solvent evaporation method. Loading improvement was achieved by increasing the alkalinity of the therapeutic agent in solution, up to 16.1% with PEG-PLGA, which could be further increased by adding DMF, compared to only 1% with no alkaline added. The therapeutic agent loading was further increased by increasing the pH of the aqueous solution as well as the polymer solution. Still further significant increases in therapeutic agent loading in the microparticles was achieved by increasing polymer concentration or viscosity. In one embodiment, the therapeutic agent is sunitinib.

Solvent Evaporation

In this method, the drug (or polymer matrix and drug) is dissolved in a volatile organic solvent, such as methylene chloride, acetone, acetonitrile, 2-butanol, 2-butanone, t-butyl alcohol, benzene, chloroform, cyclohexane, 1,2-dichloroethane, diethyl ether, ethanol, ethyl acetate, heptane, hexane, methanol, methyl tert-butyl ether, pentane, petroleum ether, iso-propanol, n-propanol, tetrahydrofuran, or mixtures thereof. The organic solution containing the drug is then suspended in an aqueous solution that contains a surface active agent such as poly(vinyl alcohol). The resulting emulsion is stirred until most of the organic solvent is evaporated, leaving solid microparticles. The resulting microparticles are washed with water and dried overnight in a lyophilizer. Microparticles with different sizes and morphologies can be obtained by this method.

Microparticles which contain labile polymers, such as certain polyanhydrides, may degrade during the fabrication process due to the presence of water. For these polymers, the following two methods, which are performed in completely anhydrous organic solvents, can be used.

Oil-in-Oil Emulsion Technique

Solvent removal can also be used to prepare particles from drugs that are hydrolytically unstable. In this method, the drug (or polymer matrix and drug) is dispersed or dissolved in a volatile organic solvent such as methylene chloride, acetone, acetonitrile, benzene, 2-butanol, 2-butanone, t-butyl alcohol, chloroform, cyclohexane, 1,2-dichloroethane, diethyl ether, ethanol, ethyl acetate, heptane, hexane, methanol, methyl tert-butyl ether, pentane, petroleum ether, iso-propanol, n-propanol, tetrahydrofuran, or mixtures thereof. This mixture is then suspended by stirring in an organic oil (such as silicon oil, castor oil, paraffin oil, or mineral oil) to form an emulsion. Solid particles form from the emulsion, which can subsequently be isolated from the supernatant. The external morphology of spheres produced with this technique is highly dependent on the identity of the drug.

Oil-in-Water Emulsion Technique

In this method, the drug (or polymer matrix and drug) is dispersed or dissolved in a volatile organic solvent such as methylene chloride, acetone, acetonitrile, benzene, 2-butanol, 2-butanone, t-butyl alcohol, chloroform, cyclohexane, 1,2-dichloroethane, diethyl ether, ethanol, ethyl acetate, heptane, hexane, methanol, methyl tert-butyl ether, pentane, petroleum ether, iso-propanol, n-propanol, tetrahydrofuran, or mixtures thereof. This mixture is then suspended by stirring in an aqueous solution of surface active agent, such as poly(vinyl alcohol), to form an emulsion. Solid particles form from the emulsion, which can subsequently be isolated from the supernatant. The external morphology of spheres produced with this technique is highly dependent on the identity of the drug.

As described in PCT/US2015/065894, microparticles with a therapeutic agent can be prepared using the oil-in-water emulsion method. In one example, sunitinib microparticles were prepared by dissolving 100 mg PEG-PLGA (5K, 45) in 1 mL methylene chloride, and dissolving 20 mg sunitinib malate in 0.5 mL DMSO and triethylamine. The solutions were then mixed together, homogenized at 5000 rpm, 1 minute into an aqueous solution containing 1% polyvinyl alcohol (PVA) and stirred for 2 hours. The particles were collected, washed with double distilled water, and freeze dried. In another example, sunitinib microparticles were also prepared according to PCT/US2015/065894 by dissolving 200 mg PLGA (2A, Alkermers) in 3 mL methylene chloride, and 40 mg sunitinib malate in 0.5 mL DMSO and triethylamine. The solutions were then mixed together and homogenized at 5000 rpm, 1 minute in 1% PVA and stirred for 2 hours. The particles were collected, washed with double distilled water, and freeze dried.

Spray Drying

In this method, the drug (or polymer matrix and drug) is dissolved in an organic solvent such as methylene chloride, acetone, acetonitrile, 2-butanol, 2-butanone, t-butyl alcohol, benzene, chloroform, cyclohexane, 1,2-dichloroethane, diethyl ether, ethanol, ethyl acetate, heptane, hexane, methanol, methyl tert-butyl ether, pentane, petroleum ether, iso-propanol, n-propanol, tetrahydrofuran, or mixtures thereof. The solution is pumped through a micronizing nozzle driven by a flow of compressed gas, and the resulting aerosol is suspended in a heated cyclone of air, allowing the solvent to evaporate from the microdroplets, forming particles. Particles ranging between 0.1-10 microns can be obtained using this method.

Phase Inversion

Particles can be formed from drugs using a phase inversion method. In this method, the drug (or polymer matrix and drug) is dissolved in a solvent, and the solution is poured into a strong non solvent for the drug to spontaneously produce, under favorable conditions, microparticles or nanoparticles. The method can be used to produce nanoparticles in a wide range of sizes, including, for example, about 100 nanometers to about 10 microns, typically possessing a narrow particle size distribution.

Coacervation

Techniques for particle formation using coacervation are known in the art, for example, in GB-B-929 406; GB-B-929 40 1; and U.S. Pat. Nos. 3,266,987, 4,794,000, and 4,460, 563. Coacervation involves the separation of a drug (or polymer matrix and drug) solution into two immiscible liquid phases. One phase is a dense coacervate phase, which contains a high concentration of the drug, while the second phase contains a low concentration of the drug. Within the dense coacervate phase, the drug forms nanoscale or microscale droplets, which harden into particles. Coacervation may be induced by a temperature change, addition of a non-solvent or addition of a micro-salt (simple coacervation), or by the addition of another polymer thereby forming an interpolymer complex (complex coacervation).

Low Temperature Casting

Methods for very low temperature casting of controlled release microspheres are described in U.S. Pat. No. 5,019,400 to Gombotz et al. In this method, the drug (or polymer matrix and sunitinib) is dissolved in a solvent. The mixture is then atomized into a vessel containing a liquid non-solvent at a temperature below the freezing point of the drug solution which freezes the drug droplets. As the droplets and non-solvent for the drug are warmed, the solvent in the droplets thaws and is extracted into the non-solvent, hardening the microspheres.

Scale Up

The processes for producing microparticles described in the Examples are amenable to scale up by methods known in the art. Examples of such methods include U.S. Pat. Nos. 4,822,534; 5,271,961; 5,945,126; 6,270,802; 6,361,798; 8,708,159; and U.S. publication 2010/0143479. U.S. Pat. No. 4,822,534 describes a method of manufacture to provide solid microspheres that involves the use of dispersions. These dispersions could be produced industrially and allowed for scale up. U.S. Pat. No. 5,271,961 disclosed the production of protein microspheres which involved the use of low temperatures, usually less than 45° C. U.S. Pat. No. 5,945,126 describes the method of manufacture to produce microparticles on full production scale while maintaining size uniformity observed in laboratory scale. U.S. Pat. Nos. 6,270,802 and 6,361,798 describe the large scale method of manufacture of polymeric microparticles whilst maintaining a sterile field. U.S. Pat. No. 8,708,159 describes the processing of microparticles on scale using a hydrocyclone apparatus. U.S. publication 2010/0143479 describes the method of manufacture of microparticles on large scale specifically for slow release microparticles.

XSpray has disclosed a device and the use of supercritical fluids to produce particles of a size below 10 µM (U.S. Pat. No. 8,167,279). Additional patents to XSpray include U.S. Pat. Nos. 8,585,942 and 8,585,943. Sun Pharmaceuticals has disclosed a process for the manufacture of microspheres or microcapsules, WO 2006/123359, herein incorporated by reference. As an example, Process A involves five steps that include 1) the preparation of a first dispersed phase comprising a therapeutically active ingredient, a biodegradable polymer and an organic solvent 2) mixing the first dispersed phase with an aqueous phase to form an emulsion 3) spraying the emulsion into a vessel equipped to remove an organic solvent and 4) passing the resulting microspheres or microcapsules through a first and second screen thereby collecting a fractionated size of the microspheres or microcapsules and 5) drying the microspheres or microcapsules.

Xu, Q. et al. have disclosed the preparation of monodispersed biodegradable polymer microparticles using a microfluidic flow-focusing device (Xu, Q., et al "Preparation of Monodispersed Biodegradable Polymer Microparticles Using a Microfluidic Flow-Focusing Device for Controlled Drug Delivery", Small, Vol 5(13): 1575-1581, 2009).

Duncanson, W. J. et al. have disclosed the use of microfluidic devices to generate microspheres (Duncanson, W. J. et al. "Microfluidic Synthesis of Monodisperse Porous Microspheres with Size-tunable Pores", Soft Matter, Vol 8, 10636-10640, 2012).

U.S. Pat. No. 8,916,196 to Evonik describes an apparatus and method for the production of emulsion based microparticles that can be used in connection with the present invention.

VIII. Process of Preparation of Surface Treated Microparticles

Abbreviations

DCM, $CH_2Cl_2$ Dichloromethane
DL Drug loading
DMSO Dimethyl sulfoxide
EtOH Ethanol
HA Sodium hyaluronate
hr, h Hour
min Minute
NaOH Sodium hydroxide
NSTMP Non-surface treated microparticles
PBS Dulbecco's phosphate-buffered saline
PCL Polycaprolactone
PEG Polyethylene glycol
PLA Poly(lactic acid)
PLGA Poly(lactic-co-glycolic acid)
PVA Polyvinyl alcohol
Rpm Revolutions per minute
RT, r.t. Room temperature
SD Standard deviation
STMP Surface treated microparticles
UV Ultraviolet General Methods All non-aqueous reactions were performed under an atmosphere of dry argon or nitrogen gas using anhydrous solvents. The structure of starting materials, intermediates, and final products was confirmed by standard analytical techniques, including NMR spectroscopy and mass spectrometry.

Materials

Sodium hydroxide (NaOH, catalog #: S318-1, Fisher Chemical), ethanol (EtOH, catalog #: A405-20, Fisher Chemical), Dulbecco's phosphate-buffered saline (PBS, catalog #: SH3085003, GE Healthcare HyClone™), sodium hyaluronate (HA, catalog #: AC251770010, Acros Organics) and Tween 20 (catalog #: BP337-100, Fisher BioReagents) were purchased from Fisher Scientific. Polyvinyl alcohol (PVA) (88 percent hydrolyzed, MW approximately 25 kD) (catalog#: 02975) was purchased from Polysciences, Inc. Sunitinib malate was purchased from LC Laboratories (catalog #: S-8803). ProVisc® (10 mg/mL, 0.85 mL, catalog#: 21989, Alcon) was purchased from Besse Medical. Poly (lactic-co-glycolic acid) (PLGA) polymer, poly(lactic-acid) (PLA) polymer, and diblock co-polymers of PLGA and polyethylene glycol (PLGA-PEG) were purchased from the Evonik Corporation (RESOMER Select 5050 DLG mPEG 5000 (10 wt percent PEG)). A FreeZone 4.5 liter benchtop freeze dry system was used for lyophilization.

ProVisc® OVD (Ophthalmic Viscosurgical Device) is a sterile, non-pyrogenic, high molecular weight, non-inflammatory highly purified fraction of sodium hyaluronate dissolved in physiological sodium chloride phosphate buffer. It is FDA approved and indicated for use as an ophthalmic surgical aid. Sodium hyaluronate is a derivative of hyaluronan for clinical use. Hyaluronan, also known as hyaluronic acid, is a naturally occurring glycosaminoglycan found throughout the body including in the aqueous and vitreous humors of the eye.

Example 1. Preparation of Biodegradable Non-Surface Treated Microparticles (NSTMP) Containing PLGA Polymer microparticles comprising PLGA and diblock copolymer of PLGA and PEG with or without sunitinib malate were prepared using a single emulsion solvent evaporation method. Briefly, PLGA (560 mg) and PLGA-PEG (5.6 mg) were co-dissolved in dichloromethane (DCM) (4 mL). Sunitinib malate (90 mg) was dissolved in dimethyl sulfoxide (DMSO) (2 mL). The polymer solution and the drug solution were mixed to form a homogeneous solution (organic phase). For empty NSTMP, DMSO (2 mL) without drug was used. For drug-loaded NSTMP, the organic phase was added to an aqueous 1% PVA solution in PBS (200 mL) and homogenized at 5,000 rpm for 1 minute using an L5M-A laboratory mixer (Silverson Machines Inc., East Longmeadow, Mass.) to obtain an emulsion. For empty NSTMP, 1 percent PVA solution in water (200 mL) was used.

The emulsion (solvent-laden microparticles) was then hardened by stirring at room temperature for more than 2 hours to allow the DCM to evaporate. The microparticles were collected by sedimentation and centrifugation, washed three times in water, and filtered through a 40-µm sterile Falcon® cell strainer (Corning Inc., Corning, N.Y.). The non-surface treated microparticles (NSTMP) were either used directly in the surface treatment process or dried by lyophilization and stored as a dry powder at −20° C. until used.

Example 2. Surface Treatment of Non-Surface Treated Microparticles (NSTMP) Using NaOH(Aq)/EtOH A pre-chilled solution containing 0.25 M NaOH (aq) and ethanol at a predetermined ratio was added to microparticles in a glass vial under stirring in an ice bath at approximately 4° C. to form a suspension at 100 mg/mL. The suspension was then stirred for a predetermined time (e.g., 3, 6 or 10 minutes) on ice and poured into a pre-chilled filtration apparatus to remove the NaOH (aq)/EtOH solution. The microparticles were further rinsed with pre-chilled water and transferred to a 50-mL centrifuge tube. The particles were then suspended in pre-chilled water and kept in a refrigerator for 30 minutes to allow the particles to settle. Following removal of the supernatant, the particles were resuspended and filtered through a 40-µm cell strainer to remove large aggregates. Subsequently, the particles were washed twice with water at room temperature and freeze-dried overnight. Detailed formulation information and conditions of NaOH (aq)/EtOH surface treatment experiments are listed in Table 1.

TABLE 1

Detailed batch information on NaOH(aq)/EtOH surface treated microparticles

| Microparticles before surface treatment | Batch size (mg) | Ratio of 0.25M NaOH (aq) to EtOH (v/v) | Treatment Time (min) | STMP ID |
|---|---|---|---|---|
| S-1 (99% PLGA 7525 4A, 1% PLGA-PEG) DL = 18.0% | 200 200 200 | 30/70 | 3 6 10 | S-2 S-3 S-4 |
| S-5 (90% PLGA 7525 4A, 10% PLGA-PEG) | 200 200 | 50/50 | 3 6 | S-6 S-7 |
| DL = 18.9% | 200 | 30/70 | 6 | S-8 |
| S-9 (99% PLGA 7525 4A, 1% PLGA-PEG) DL = 18.3% | 1000 | 30/70 | 3 | S-10 |
| S-11 (99% PLGA 7525 4A, 1% PLGA-PEG) DL = 11.1% | 2300 | 30/70 | 3 | S-12 |
| S-13 (99% PLGA 7525 4A, 1% PLGA-PEG) DL = 11.9% | 3600 | 30/70 | 3 | S-14 |
| S-15 (99% PLGA 7525 4A, 1% PLGA-PEG) DL = 2.15% | 2000 | 30/70 | 3 | S-16 |
| S-17 (99% PLGA 7525 4A, 1% PLGA-PEG) DL = 2.21% | 2000 | 30/70 | 3 | S-18 |

DL = Drug loading.

Example 3. In Vitro Assessment of Particle Aggregability

Surface treated microparticles (STMP) were suspended in phosphate buffered saline (PBS) at a concentration of 200 mg/mL. Thirty or fifty microliters of the suspension were injected into 1.5-2.0 mL of PBS or sodium hyaluronate solution (HA, 5 mg/mL in PBS) pre-warmed at 37° C. in a 2 mL microcentrifuge tube using a 0.5 mL insulin syringe with a permanent 27-gauge needle (Terumo or Easy Touch brand). The microcentrifuge tube was then incubated in a water bath at 37° C. for 2 hours. The aggregability of the microparticles was assessed by visual observation and/or imaging under gentle agitation by inverting and/or tapping and flicking the tubes containing the microparticles. Non-surface treated microparticles (NSTMP) were used as a control.

A successful surface treatment process is expected to result in STMP that maintain good suspendability, syringeability and injectability. Most importantly, after the injection into PBS or sodium hyaluronate and the 2 hour incubation at 37° C., the STMP are expected to form consolidated aggregate(s) that do not break into smaller aggregates or free floating particles under gentle agitation, a key feature that differentiates STMP from NSTMP and STMP with low aggregability.

Example 4. Effect of Temperature During Surface Treatment on Microparticle Properties The effect of temperature on surface treatment was studied by comparing particles treated at room temperature vs. treated at 4° C. The procedure for surface treatment at room temperature was identical to the procedure described in Example 2 except that it was conducted at room temperature instead of at 4° C.

When the surface treatment process was carried out at room temperature in a mixture of 0.25 M NaOH and EtOH (v/v: 30/70 or 70/30), the particles aggregated quickly and irreversibly during surface treatment. In contrast, particles treated at 4° C. in a mixture of NaOH/EtOH at the same volume ratio did not aggregate during the surface treatment process and maintained good suspendability and injectability upon reconstitution. For surface treatment at room temperature in 0.25 M NaOH without EtOH, the particles did not aggregate during the 1 hour surface treatment. In addition, STMP treated in NaOH failed to aggregate following incubation at 37° C. In contrast, STMP treated around 4° C. did not aggregate during surface treatment, but aggregated following incubation at 37° C. After lyophilization and reconstitution in a particle diluent, the STMP were easily loaded into syringes through a 27 gauge needle and injected without needle blockage.

Example 5. Effect of PEG Content on the Aggregability of Surface Treated Microparticles

TABLE 2

NSTMP and STMP containing different percentages of PLGA:PLGA-PEG

| Formulation # | PLGA (wt %) | PLGA-PEG (wt %) | Surface Treatment Condition |
|---|---|---|---|
| S-1 | 99% | 1% | None |
| S-3 | 99% | 1% | 0.25M NaOH/EtOH (30/70, v/v), 6 min |
| S-5 | 90% | 10% | None |
| S-8 | 90% | 10% | 0.25M NaOH/EtOH (30/70, v/v), 6 min |

Two batches of NSTMP (S-1 and S-5) and two batches of STMP (S-3 and S-8) containing different weight percentages of PLGA/PLGA-PEG were surface treated following the procedure described below and their aggregability in both PBS and HA gel were evaluated.

As listed in Table 2 above, formulation S-3 contained 1% PLGA-PEG and S-8 contained 10% of PLGA-PEG. Samples S-3 and S-8 were individually treated in a mixture of 0.25M NaOH and EtOH at a volume ratio of 30/70 at 4° C. for 6 minutes. Following injection in PBS and incubation at 37° C. for 2 hours, the microcentrifuge tubes were inverted and the aggregability of the particles was assessed by visual inspection. As illustrated in FIG. 1, the NSTMP S-1 and S-5 started to disperse immediately after the tubes were inverted, while the STMP, S-3 and S-8, remained aggregated at the bottom of the tubes without dispersion throughout the entire period of observation (about 10 minutes).

Figure 2:
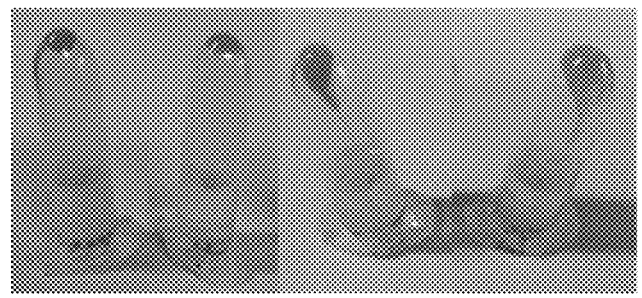
FIG. 2 illustrates the aggregation of surface treated microparticles (STMP) (S-3 and S-8) after injection into HA and incubation at 37° C. for 2 hours. Samples left to right are S-1, S-3, S-5 and S-8 (Example 5).

A similar second experiment was conducted by injecting the same particle suspensions into HA solutions and incubating the samples at 37° C. for 2 hours. Immediately after the tubes were inverted, none of the particles became dispersed, including NSTMP; refer to FIG. 2. This is likely due to the higher viscosity of HA that prevents particles from diffusing rapidly in the gel solution. Different from S-1 which remained aggregated throughout the experiment, S-5 started to become dispersed in HA 2 minutes after the tube was inverted. Without wishing to be bound to any one theory, this may be related to the higher PEG content in S-1 that affects the interaction between particles and between the particle surfaces and HA, and thus the diffusion of S-5 in HA was less hindered than that of S-1. Though S-8 remained aggregated after injection and incubation in PBS, it appeared more dispersive in HA solution. In contrast, S-3, which contains less PEG than S-8, was able to aggregate in both PBS and HA solution. These data indicate that the aggregation and dispersion of STMP can be affected by both the particle composition and properties of the medium where the STMP are injected.

Figure 3:
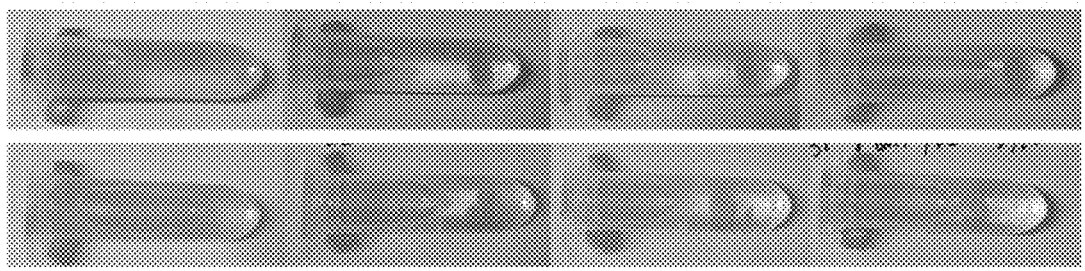
FIG. 3 illustrates the result of in vitro aggregation and dispersion of particles after a 2-hour incubation in PBS at 37° C. followed by agitation to detach the aggregates from the bottom of the tubes. Top row from left to right samples: S-1, S-2, S-3, S-4; Bottom row from left to right samples: S-5, S-6, S-7 and S-8 (Example 5).

In a third experiment, samples containing S-1, S-2, S-3, S-4, S-5, S-6, S-7 and S-8 were incubated in PBS at 37° C. for 2 hours. After assessing the aggregability by inverting the tubes, stronger agitation was applied by tapping the tubes on the bench, which caused the particle aggregates to detach from the bottom of the tubes. The integrity of the aggregates was then examined and compared among different formulations. As shown in FIG. 3, S-3 (1 percent PLGA-PEG) remained as an integrated single aggregate after detachment from the bottom of the tube. In comparison, though most particles in S-8 (10% PLGA-PEG) remained as one large aggregate, many dispersed small aggregates or particles were visible in the tube. The assay with stronger agitation allowed further differentiation of the aggregability of different particle formulations. Overall, the data suggest that STMP with lower PEG content generally form stronger and more consolidated aggregates than STMP with higher PEG content.

Example 6. Effect of Surface Treatment with PBS/EtOH on Microparticles

Since NaOH is a strong base that may cause partial degradation of polymers and lead to rapid modification of the surface properties of particles, a neutral phosphate buffered saline (PBS) solution at pH 7.4 was evaluated as an alternative to NaOH and the effect of surface treatment using PBS/EtOH on microparticles was studied. The surface treatment procedure was identical to that described in Example 2, except that the NaOH solution was replaced with PBS (pH 7.4). The experiment was performed in an ice bath at approximately 4° C. Detailed formulation composition and surface treatment conditions are listed in Table 3. The aggregability of the surface treated microparticles (STMP) was tested following the procedure described in Example 3.

TABLE 3

Formulation composition and conditions of surface treatment with PBS/EtOH

| Particle ID before treatment | Composition | Drug Loading | Batch size (mg) | PBS/EtOH (v/v) | Treatment Time (min) | STMP ID |
|---|---|---|---|---|---|---|
| S-11 | 99% PLGA | 11.1% | 200 | 30/70 | 3 | S-21 |
| S-19 | 7525 4A, 1% PLGA-PEG | 11.8% | 500 | | | S-22 |
| | | | 500 | | | S-23 |
| | | | 500 | | 6 | S-24 |
| S-20 | | 0% | 200 | | 6 | S-25 |
| | | | 200 | | 12 | S-26 |

Figure 4:
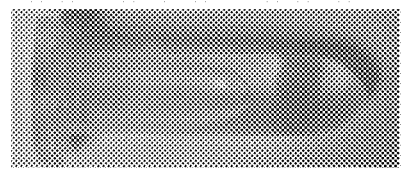
FIG. 4 illustrates in vitro aggregation of representative surface treated microparticles (STMP) treated with PBS/EtOH (sample S-21) after a 2 hour incubation in PBS at 37° C. followed by agitation by tapping and flicking the tube (Example 6).

The results of the aggregability test demonstrated that similar to surface treatment with NaOH/EtOH, all of the STMP treated with PBS/EtOH were able to form an aggregate after injection into PBS and incubation for 2 hours at 37° C. The aggregates appeared stable and resistant to gentle agitation; refer to FIG. 4, a photo of S-21. There was no apparent difference in particle aggregability under in vitro aggregation assay (procedure was conducted as described in Example 3) between these STMP and the STMP generated by treatment in NaOH/EtOH. Both drug-loaded STMP and empty STMP were able to aggregate in PBS, suggesting the surface treatment process likely has good compatibility with various particle formulations with or without drug.

Example 7. Modification of the Surface Treatment Conditions Using NaOH(Aq)/EtOH To further optimize the surface treatment conditions with NaOH(aq)/EtOH, the impact of various parameters, such as NaOH concentration, aqueous/EtOH ratio, and treatment time, on surface treatment were studied (Table 4). It is worth noting that in this Example, the overall molar concentration of NaOH in the entire aqueous/EtOH mixture was used as a variable independent of the ratio of aqueous solution to EtOH instead of using the molarity of NaOH in the aqueous phase only as in Example 2. For example, 0.25M NaOH (aq)/EtOH (v/v: 30/70) in Example 2 is equivalent to 0.075M of NaOH in an aqueous/EtOH (v/v: 30/70) mixture. Thus the volume ratio of aqueous to EtOH was modified from 30/70 to 50/50 and 70/30 with the same total amount of NaOH in the mixture. In addition, the amount of NaOH was decreased by 10- or 100-fold without changing the ratio of aqueous solution to EtOH. The different treatment time was chosen to achieve comparable effectiveness of surface treatment. The procedure for surface treatment on microparticles was the same as Example 2.

TABLE 4

Detailed batch information on modified NaOH(aq)/EtOH STMP

| Microparticles before surface treatment | Batch size (mg) | NaOH concentration in H$_2$O/EtOH mixture (M) | H$_2$O/EtOH ratio (v/v) | Treatment Time (min) | STMP ID |
|---|---|---|---|---|---|
| S-27 (99% PLGA 7525 4A, 1% PLGA-PEG) DL = 11.3% | 200 | 0.075 | 50/50 | 10 | S-28 |
| | 200 | | 50/50 | 20 | S-29 |
| | 200 | | 70/30 | 15 | S-30 |
| | 200 | | 70/30 | 30 | S-31 |
| | 200 | 0.0075 | 30/70 | 3 | S-32 |
| | 200 | | 30/70 | 10 | S-33 |
| | 200 | 0.00075 | 30/70 | 3 | S-34 |
| | 200 | | 30/70 | 10 | S-35 |

Example 8. Effect of Surface Treatment Using HCl/EtOH on Microparticles

As surface treatment using an aqueous solution of basic pH (Example 2 and Example 7) or neutral pH (Example 6) had been tested previously, the effect of aqueous solution of acidic pH was evaluated in Example 8. HCl was selected as a representative acid. As shown in Table 5, microparticles were treated for 3 minutes in 0.075 M or 0.0075 M of HCl in H$_2$O/EtOH (v/v: 30/70) mixture, respectively. The procedure for HCl/EtOH surface treatment was the same as in Example 2 except that HCl (aq) was used to replace NaOH (aq).

TABLE 5

Detailed batch information of HCl/EtOH treated STMP

| Microparticles before surface treatment | Batch size (mg) | HCl concentration in H$_2$O/EtOH mixture (M) | H$_2$O/EtOH ratio (v/v) | Treatment Time (min) | Final surface treated particles |
|---|---|---|---|---|---|
| S-27 (99% PLGA 7525 4A, 1% PLGA-PEG) DL = 11.3% | 200 | 0.075 | 30/70 | 3 | S-36 |
| | 200 | 0.0075 | 30/70 | 3 | S-37 |

Example 9. Surface Treatment on Wet Microparticles

In addition to conducting surface treatment on NSTMP by first re-suspending NSTMP dry powder in an aqueous solution as illustrated in the previous examples, the feasibility of surface treatment on NSTMP prior to drying (i.e., "wet" microparticles) was also evaluated. It is expected to be easier to integrate a surface treatment step using "wet" NSTMP into the entire process of scale-up production of STMP than a step using dry powder of NSTMP. After obtaining "wet" NSTMP prior to lyophilization as shown in Example 1, an aliquot of the suspension was lyophilized to determine the particle mass per volume. The particle suspension was then concentrated or diluted accordingly to reach desired concentration and cooled down to desired temperature. Other reagents needed for surface treatment were then added to the suspension to reach desired conditions (e.g., concentration of each chemical reagent) as described in Table 6 to start the surface treatment process. The rest of the surface treatment process is the same as described on dry particles in Example 2. The detailed batch information and experimental conditions are listed in Table 6.

TABLE 6

Detailed batch information and experimental conditions of surface treatment on "wet" microparticles

| | | | Final surface treatment solvent | | | |
|---|---|---|---|---|---|---|
| Microparticles before surface treatment | Batch size (mg) | Solute (base, acid or salt) | Solute concentration in H$_2$O/EtOH mixture (M) | H$_2$O/EtOH ratio (v/v) | Treatment Time (min) | STMP ID |
| S-38 (99% PLGA 7525 4A, 1% PLGA-PEG) DL = 11.6% | 450 | NaOH | 0.075 | 30/70 | 3 | S-39 |
| | 450 | | 0.0075 | 30/70 | 10 | S-40 |
| | 450 | | 0.075 | 70/30 | 15 | S-41 |
| | 450 | | 0.00075 | 70/30 | 30 | S-42 |
| | 450 | HCl | 0.0075 | 30/70 | 3 | S-43 |
| | 450 | KCl | 0.075 | 30/70 | 20 | S-44 |
| | 450 | | 0.35 | 30/70 | 20 | S-45 |

Example 10. Optimized Method for Assessing Particle Aggregability In Vitro

To improve the method for assessing particle aggregability in vitro, an orbital shaker was used to replace the manual agitation used in Example 3.

Fifty microliters of STMP suspension in PBS at 200 mg/mL was injected in 2 mL of PBS pre-warmed at 37° C. in a 16-mm round-bottom glass test tube using a 1 mL insulin syringe with a permanent 27-gauge needle (Terumo or Easy Touch brand). The test tube was then incubated in a water bath at 37° C. for 2 hours. The aggregability of the microparticles was assessed by visual inspection and/or imaging after shaking for 30 seconds at 400 rpm on an orbital shaker (Thermo Scientific™ Multi-Platform Shakers: Catalog No. 13-687-700). The test tube containing particles/aggregates was then turned horizontally for visual assessment of the particle aggregability. NSTMP were used as a control.

Figure 17:
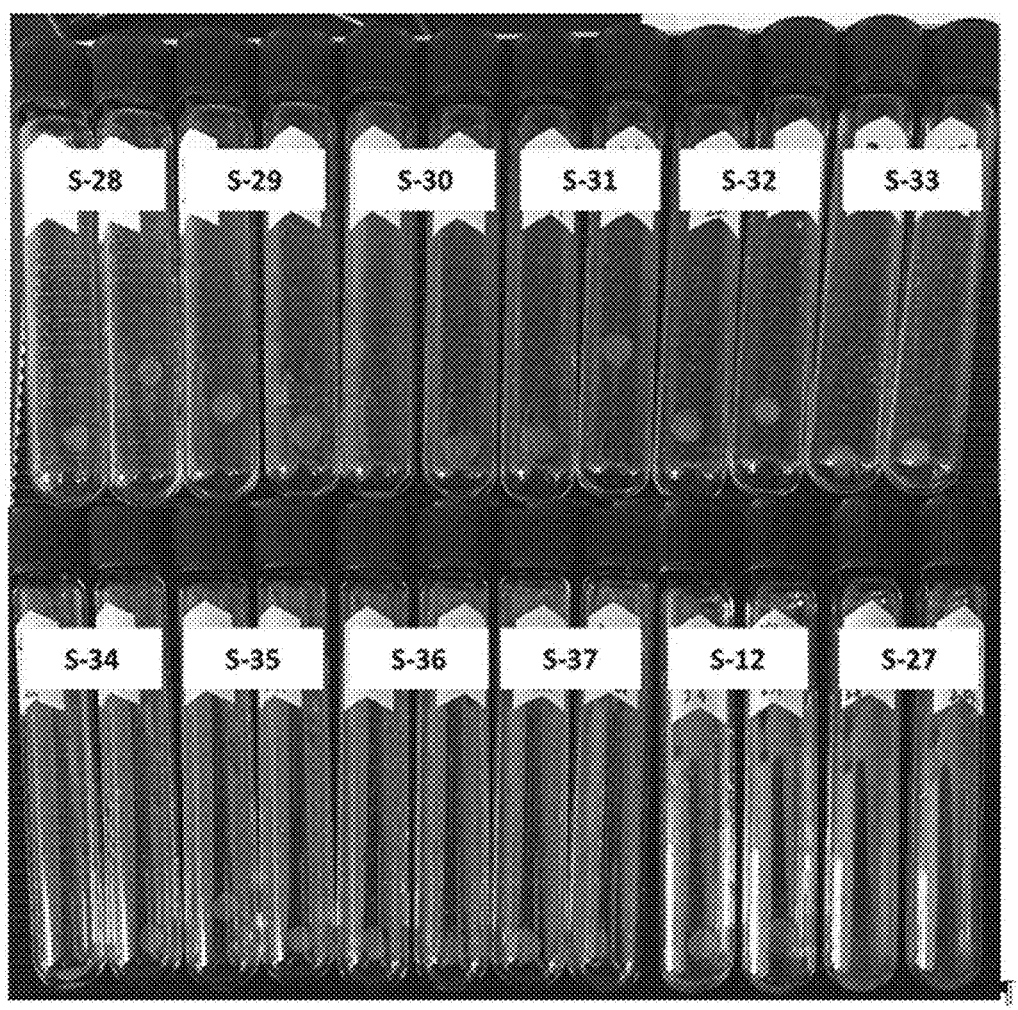
FIG. 17 illustrates the aggregation of surface treated microparticles (STMP) (S-28 to S-37 and S-12) after injection into PBS and incubation at 37° C. for 2 hours. After the 2 hour-incubation, the non-surface treated microparticles (NSTMP), S-27, became dispersed when the test tube was placed on an orbital shaker at 400 rpm for 30 seconds, while the surface treated microparticles (STMP), S-28 to S-37 and S-12, remained aggregated under the same agitation condition. Samples from left to right, top row to bottom row are S-28, S-29, S-30, S-31, S-32, S-33, S-34, S-35, S-36, S-37, S-12 and S-27 (Example 10).

As shown in FIG. 17, all the STMP in Examples 7 and 8 formed an aggregate after the 2-hour incubation and the aggregates remained mostly intact following 30-second shaking on an orbital shaker. In contrast, NSTMP in S-27 became fully dispersed following the same agitation. S-12 described in Example 2 was also included in this assessment to compare the aggregability of microparticles treated under different conditions. The results suggest all the modified surface treatment conditions in Examples 7 and 8 resulted in STMP with aggregability similar to that of S-12.

Figure 18:
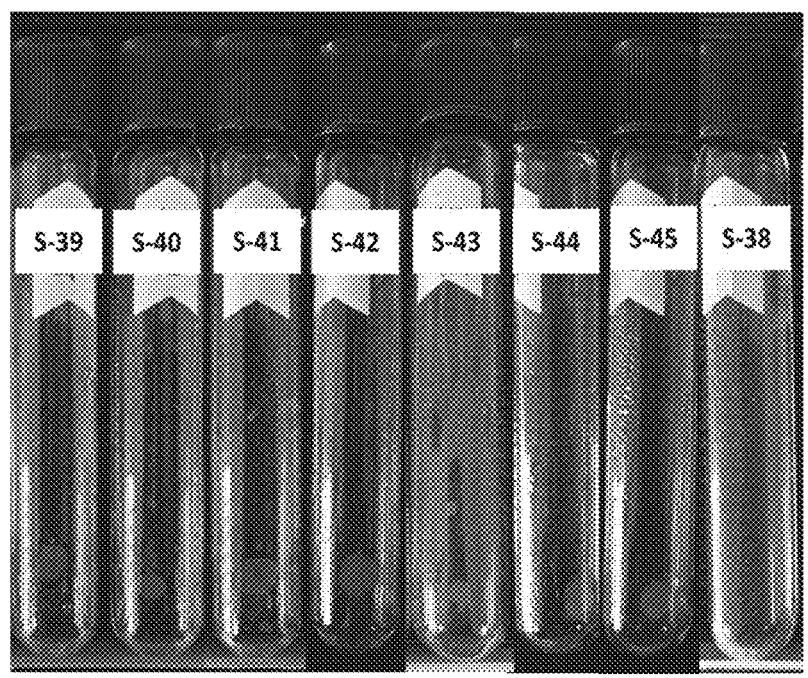
FIG. 18 illustrates the aggregation of surface treated microparticles (STMP) (S-39 to S-45) after injection into PBS and incubation at 37° C. for 2 hours. After the 2 hour-incubation, the non-surface treated microparticles (NSTMP), S-38, became dispersed when the test tube was placed on an orbital shaker at 400 rpm for 30 seconds, while the surface treated microparticles (STMP), S-39 to S-45, remained aggregated under the same agitation condition. Samples from left to right, top row to bottom row are S-39, S-40, S-41, S-42, S-43, S-44 and S-45 (Example 10).

As shown in FIG. 18, all the STMP (S-39, S-40, S-41, S-42, S-43, S-44, S-45) in Example 9 formed an aggregate after the 2-hour incubation and the aggregates remained mostly intact following 30-second shaking on an orbital shaker, while NSTMP (S-38) became fully dispersed following the same agitation. S-42, S-44 and S-45 appeared to aggregate better than other STMP samples in FIG. 18 and as well as surface treatment on dry particle in FIG. 17. The results demonstrate the success and feasibility of surface treatment on wet microparticles.

Example 11. Determination of Drug Loading

Drug loading was determined by UV-Vis spectrophotometry. Microparticles containing sunitinib (10 mg total weight) were dissolved in anhydrous DMSO (1 mL) and further diluted until the concentration of drug was in the linear range of the standard curve of UV absorbance of the drug. The concentration of the drug was determined by comparing the UV absorbance to a standard curve. Drug loading is defined as the weight ratio of drug to microparticles.

Example 12. In Vitro Drug Release Study

Figure 5:
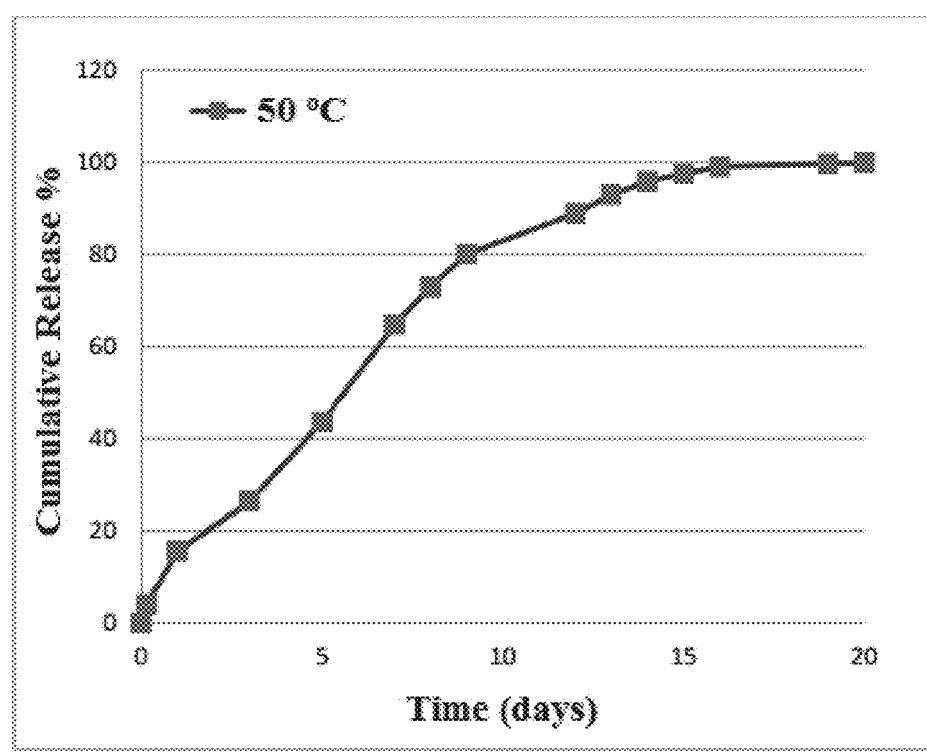
FIG. 5 illustrates the in vitro accelerated drug release profile of a representative batch of surface treated microparticles (STMP) (S-12) (Example 12). The x-axis is time measured in days and the y-axis is cumulative release percent.

Microparticles containing sunitinib (10 mg total weight) were suspended in PBS (4 mL) containing 1% Tween 20 in a 6-mL glass vial and incubated at 37° C. under shaking at 150 rpm. At predetermined time points, 3 mL of the supernatant was withdrawn after particles settled to the bottom of the vial and replaced with 3 mL of fresh release medium. The drug content in the supernatant was determined by UV-Vis spectrophotometry or HPLC. Alternatively, the above procedure can be run at 50° C. to determine an accelerated in vitro drug release rate as shown in FIG. 5.

Example 13. Studies on the Effects of Surface Treatment on Microparticles

Besides aggregability, the effect of surface treatment on other properties of microparticles was also studied to fully evaluate the feasibility of surface treatment. As shown in Table 7, in general, the yield and drug loading of STMP (in Example 2) treated for longer periods of time were slightly lower than those treated for shorter period of time, suggesting that at 0.25M NaOH/EtOH (v/v: 3:7), the time window for producing STMP with high yield and loading is narrow (on the order of minutes). However, under the modified conditions presented in Example 7, the treatment time can be further extended to tens of minutes without reducing DL and yield (Table 7) as well as aggregability (Example 10). STMP treated with HCl(aq)/EtOH in Example 8 maintained the DL prior to surface treatment with relatively high yield (S-36 and S-37). In addition, STMP (S-42, S-44 and S-45) produced by surface treatment on wet microparticles in Example 9 also maintained the DL prior to surface treatment with comparable yield as STMP produced by surface treatment on dry particles in Example 7 and 8.

TABLE 7

Yield and drug loading of STMP

| Sample | Yield | Drug loading (DL) prior to surface treatment | Drug loading after surface treatment |
| --- | --- | --- | --- |
| S-2 | 51% | 18.0% | 14.2% |
| S-3 | 50% | 18.0% | 15.3% |
| S-4 | 36% | 18.0% | 6.3% |
| S-6 | 30% | 18.9% | 15.0% |
| S-7 | 35% | 18.9% | 14.7% |
| S-8 | 28% | 18.9% | 11.6% |
| S-10 | 67% | 18.3% | 18.6% |
| S-12 | 68% | 11.1% | 11.6% |
| S-14 | 70% | 11.9% | 12.0% |
| S-16 | 56% | 2.15% | 2.11% |
| S-28 | 43% | 11.3% | 11.8% |
| S-29 | 49% | 11.3% | 11.0% |
| S-30 | 60% | 11.3% | 10.1% |
| S-31 | 61% | 11.3% | 10.6% |
| S-32 | 44% | 11.3% | 12.0% |
| S-33 | 48% | 11.3% | 11.5% |
| S-34 | 49% | 11.3% | 11.5% |
| S-35 | 58% | 11.3% | 12.0% |
| S-36 | 61% | 11.3% | 10.3% |
| S-37 | 69% | 11.3% | 11.6% |
| S-42 | 44% | 11.6% | 11.2% |
| S-44 | 50% | 11.6% | 12.0% |
| S-45 | 43% | 11.6% | 12.1% |

Figure 6:
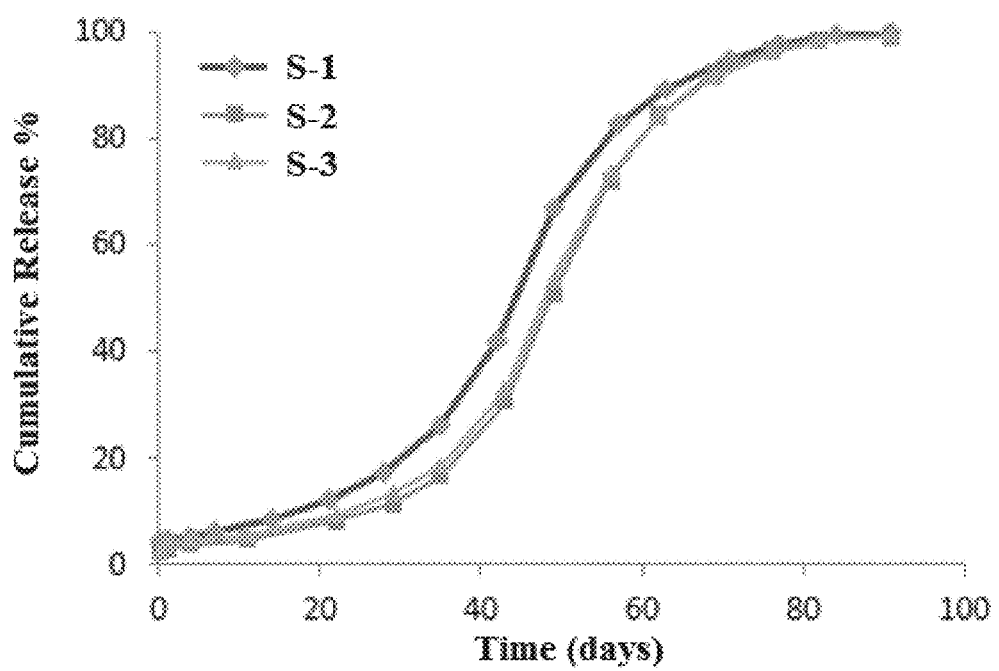
FIG. 6 illustrates the in vitro drug release profiles for samples S-1, S-2, and S-3 in PBS with 1% Tween 20 at 37° C. (Example 13). The x-axis is time measured in days and the y-axis is cumulative release percent.

FIG. 6 illustrates representative in vitro drug release profiles of NSTMP (S-1) and the corresponding STMP (S-2 and S-3) generated from the same batch of NSTMP. Overall, the release profiles are similar for microparticles before and after surface treatment except that the initial release rate of STMP was lower than that of NSTMP. This suggests that under the surface treatment conditions drug molecules that are bound to or near the microparticle surface may have been removed during the surface treatment process.

Example 14. Wettability of Surface Treated Microparticles

The wettability of representative batches of STMP and NSTMP was characterized using the Washburn method. Briefly, two glass capillary tubes with filter bases were separately filled with equivalent masses of STMP and NSTMP dry powder. The bottom of the capillary tubes were then inserted into a beaker with water and water was drawn into the tubes over time due to capillary action. The increase in mass of the tube and the height of water in the tubes were determined as a function of time. The rate of water absorption was relatively rapid in the tube containing NSTMP, but relatively slow for STMP. Similarly, at the end of the test, the mass increase of the tubes was much higher for NSTMP than for STMP, indicating that the surface modification leads to reduction of wettability of the microparticles likely due to removal of surfactant or both surfactant and polymer from particle surface.

Figure 7:
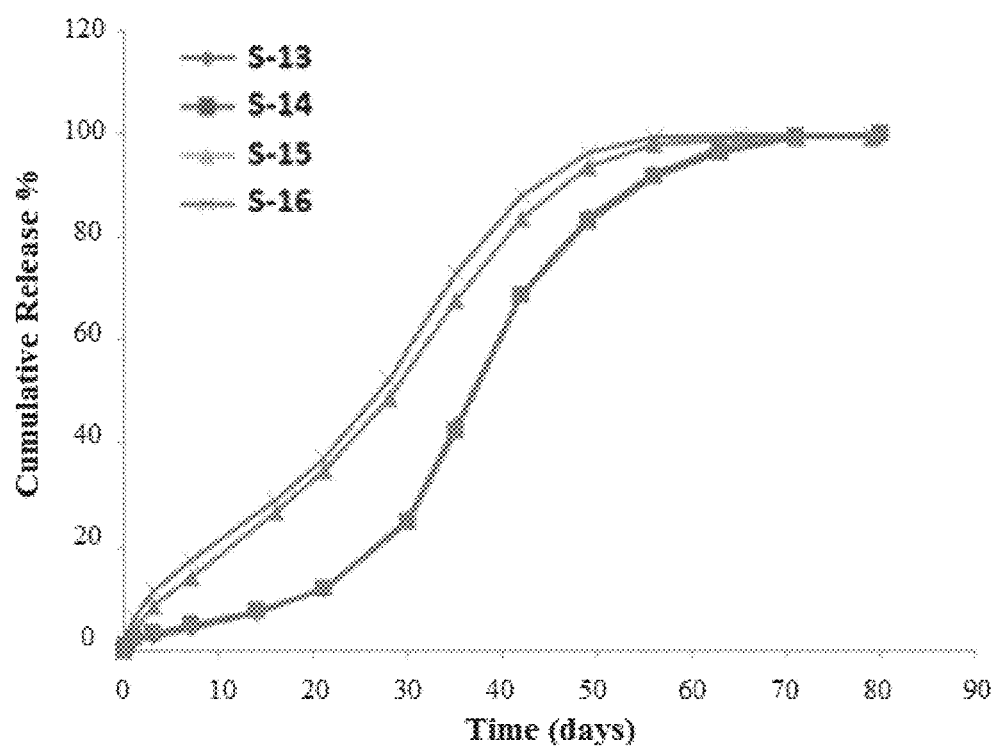
FIG. 7 illustrates the in vitro drug release profile of S-13, S-14, S-15 and S-16 in PBS with 1% Tween 20 at 37° C. (Example 15). The x-axis is time measured in days and the y-axis is cumulative release percent.

Example 15. Preparation of Samples S-10, S-12, S-14, S-16, and S-18 and the Study of their Drug Release Profiles Samples S-10 to S-16 and S-18 were prepared at a larger scale of 1 to 3.6 grams. The yield and drug loading of these batches are shown in Table 6 above. It is worth noting that the drug loading was not significantly changed by surface treatment. The average particle size of these STMP samples was similar to that of the corresponding NSTMP prior to surface treatment (data not shown). As shown in FIG. 7, the release profiles of the STMP prepared at a larger scale (S-14 and S-16) were similar to the corresponding NSTMP as well, indicating that the surface treatment process had minimal effect on the overall drug release.

Example 16. Injectability and Dosing Consistency of Surface Treated Microparticles (STMP)

A suspension of STMP (ST-1-5, approximately 10 percent drug loading) at approximately 200 mg/mL was prepared by suspending the microparticles in 5-fold diluted ProVisc® solution containing 2 mg/mL of HA. After an incubation period of 2 hours at room temperature, 10 µL of the STMP suspension was loaded into a 50 µL Hamilton syringe with an attached 27-gauge needle. Following brief vortexing to fully suspend the STMP, the syringe was held horizontally for 2 minutes and vertically for 2 minutes prior to injection into a microcentrifuge tube. The injection was repeated using 3 different syringes and each syringe was tested 3 times. The STMP in each tube was then dissolved in DMSO and the dose of drug was determined by UV-Vis spectrophotometry. As shown in Table 8, excellent dosing consistency between injections using the same syringe and between different syringes was observed, suggesting that the STMP suspension in diluted ProVisc® remained stable at room temperature for a sufficient amount of time to allow consistent dosing of the relatively small volume of injection (e.g., 10 µL).

Example 17. Impact of Microparticle Concentration and Particle Diluent on the Aggregation of Surface Treated Microparticles (STMP)

To investigate the effect of particle concentration and diluent on the aggregation of STMP, STMP suspensions (50 µL) in 5-fold diluted ProVisc® at 2 different microparticle concentrations (100 mg/mL and 200 mg/mL) were injected into 4 mL of PBS or HA solution and incubated at 37° C. for 2 hours.

As illustrated in the top panel of FIG. 8C and FIG. 3D, the STMP at 200 mg/mL in diluted ProVisc® were able to form a consolidated aggregate in both PBS and HA following a 2 hour incubation at 37° C. Compared to 200 mg/mL STMP suspended in PBS, the aggregation of 200 mg/mL STMP in diluted ProVisc® appeared slower, but the aggregate became more consolidated over time, suggesting the HA molecules in the particle diluent may hinder the contact between STMP and slow down the aggregation process. On the other hand, due to its viscoelastic properties, HA may help keep particles localized and allow sufficient time for STMP to form an aggregate. The particle aggregates formed in HA also appeared to have a more spherical morphology than those formed in PBS, suggesting that if a viscoelastic solution is used as the particle diluent, an optimal range of diluent concentration needs to be identified to improve the overall performance of STMP aggregation.

After the 2 hour incubation, the strength of the aggregates was tested by shaking the test tubes at 250 rpm on an orbital shaker. As illustrated in the bottom panel of FIG. 8C and FIG. 8D, the aggregates were able to endure the shear stress generated by shaking with no or limited dispersion of microparticles.

In comparison, even though the STMP of 100 mg/mL appeared to form an aggregate in PBS (top panel, FIG. 8A), the aggregate appeared less dense than that of the 200 mg/mL STMP in PBS (top panel, FIG. 8C) and tended to disaggregate into individual microparticles under agitation (bottom panel, FIG. 8A). In addition, the STMP of 100 mg/mL was not able to form one consolidated aggregate in HA at the end of the 2 hour incubation period (top panel, FIG. 8B) and many STMP became dispersed in HA upon shaking at 250 rpm (bottom panel, FIG. 8B). Similar to HA

TABLE 8

Injectability and dosing consistency of STMP

| Sample Name | UV Reading | Dose (mg) | Average dose per syringe n = 3 (mg) | Standard deviation (mg) | Standard deviation (%) | Average dose n = 9 (mg) | Standard deviation (mg) | Standard deviation (%) |
|---|---|---|---|---|---|---|---|---|
| Syringe 1-a | 1.019 | .1966 | .1974 | .0140 | 7.0942 | | | |
| Syringe 1-b | .953 | .1838 | | | | | | |
| Syringe 1-c | 1.098 | .2118 | | | | | | |
| Syringe 2-a | 1.136 | .2191 | .2058 | .0122 | 5.9332 | .2031 | .0129 | 6.3345 |
| Syringe 2-b | 1.052 | .2029 | | | | | | |
| Syringe 2-c | 1.012 | .1952 | | | | | | |
| Syringe 3-a | 1.052 | .2029 | .2062 | .0156 | 7.5633 | | | |
| Syringe 3-b | 1.157 | .2232 | | | | | | |
| Syringe 3-c | .998 | .1925 | | | | | | | molecules in particle diluent, the HA molecules in the test medium may further decrease particle-particle contact and reduce the chance of forming a consolidated aggregate. The results suggest that the aggregability of STMP decreases at lower microparticle concentration, possibly due to increased average particle-particle distance and decreased chance of direct contact between particles. The aggregation may also be further hindered by other molecules, such as HA, in the test medium.

In summary, the aggregation of STMP can be affected by particle concentration, particle diluent and the environment into which the particles are delivered. Overall the data demonstrate that under appropriate conditions, the STMP have good aggregability in different particle diluents and test media.

Example 18. Aggregation of Surface Treated Microparticles (STMP) in Cow Eyes Ex Vivo To evaluate the aggregability of STMP following intravitreal injection ex vivo, enucleated cow eyes (J.W. Treuth & Sons, Catonsville, Md.) were utilized. The eyes were kept on ice prior to use. Briefly, 30 µL of 200 mg/mL STMP, S-10, suspended in 5-fold diluted ProVisc® was injected into the central vitreous of cow eyes using a 0.5 mL insulin syringe (Terumo) with a 27-gauge needle and three injections were performed in each cow eye at different locations. After a 2 hour incubation at 37° C., the eyes were cut open and the aggregates of STMP were examined using a dissecting microscope. As shown in FIG. 9, the injected STMP formed consolidated aggregates in cow vitreous and no apparent particle dispersion was observed.

Figure 10A:
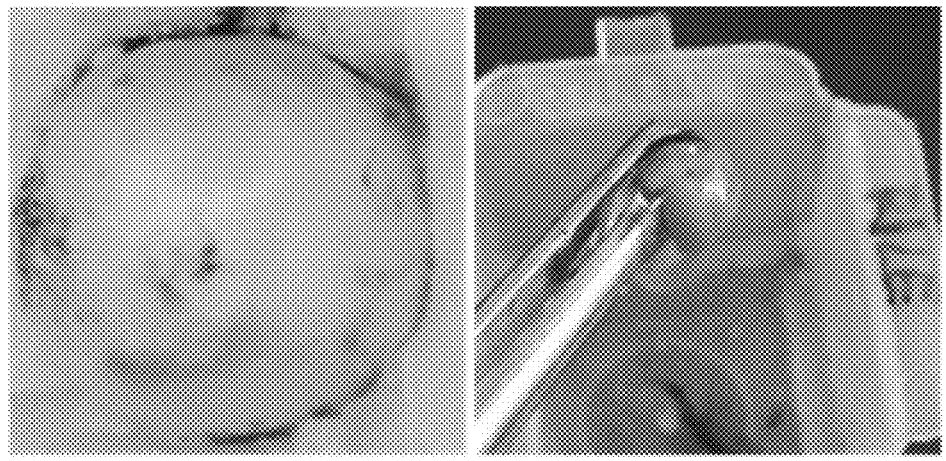
FIG. 10A are photos of particle aggregates in the vitreous (left) and out of the vitreous (right) following injection of STMP, S-10, suspended in PBS into the central vitreous of rabbit eyes (Example 19).
Figure 10B:
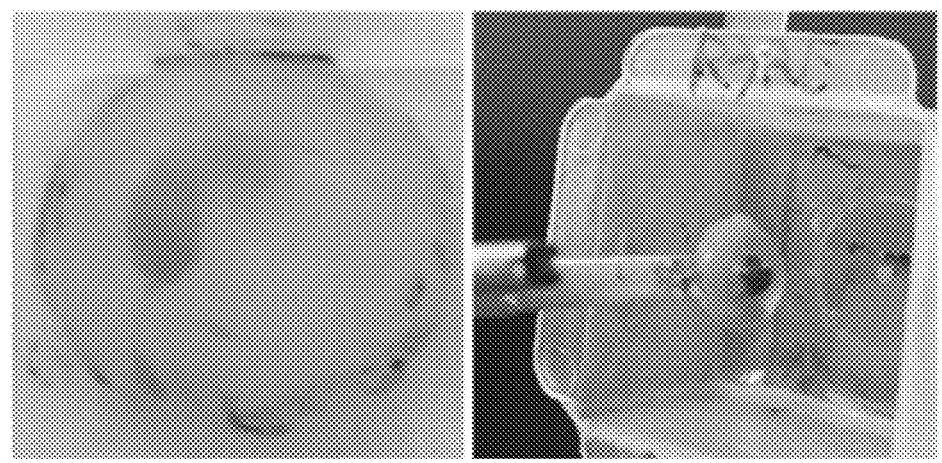
FIG. 10B are photos of particle aggregates in the vitreous (left) and out of the vitreous (right) following injection of STMP, S-10, suspended in 5-fold diluted ProVisc into the central vitreous of rabbit eyes (Example 19).

Example 19. Aggregation of Surface Treated Microparticles (STMP) in Rabbit Eyes In Vivo To study the aggregation of surface treated microparticles in rabbit eyes in vivo, 50 µL of 200 mg/mL STMP, S-10, suspended in PBS (FIG. 10A) or 5-fold diluted ProVisc® (FIG. 10B) were injected to the central vitreous of Dutch Belted rabbit eyes using a 0.5 mL insulin syringe (Terumo) with a 27 gauge needle. Four days after the dosing, the rabbits were sacrificed and the eyes were nucleated and frozen immediately. The frozen eyes were cut into halves and the posterior half of the eye was thawed at room temperature for 3 minutes to allow isolation of the vitreous from the eye cup, as shown in the left photo of FIG. 10A and FIG. 10B. The frozen vitreous containing particles was placed in a cassette to allow the vitreous to thoroughly thaw. The aggregates of STMP in the vitreous could be easily separated from vitreous using forceps, proving the formation of consolidated STMP aggregates in rabbit eyes.

Example 20. Distribution, Tolerability and Pharmacokinetics of Sunitinib-Encapsulated Surface Treated Microparticles (STMP) Following an Intravitreal (IVT) Injection in Rabbits The distribution and tolerability of STMP and NSTMP were studied in pigmented New Zealand rabbits (F1) following an intravitreal injection of the microparticles. ProVisc® was diluted 5-fold in PBS and used as a diluent to prepare particle suspensions of about 200 mg/mL for injection. Detailed study groups and conditions are presented in Table 9.

Figure 11A:
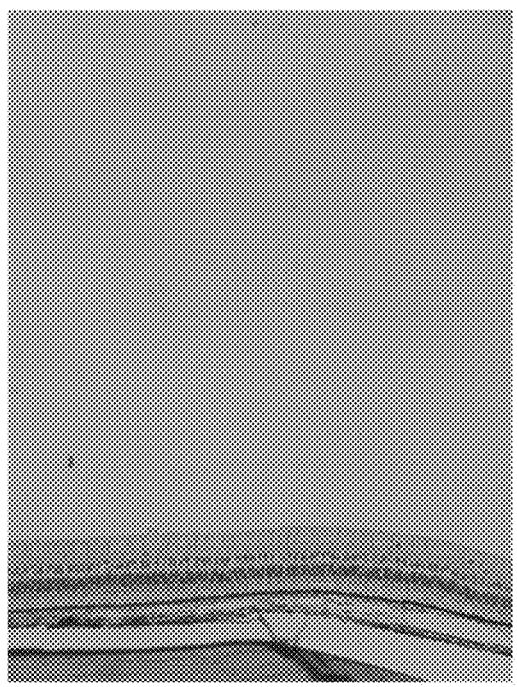
FIG. 11A illustrates representative 1-month histology images of rabbit eyes injected with surface treated microparticles (STMP) (Example 20).
Figure 11B:
FIG. 11B illustrates representative 1-month histology images of rabbit eyes injected with non-surface treated microparticles (NSTMP) (Example 20).

Complete ocular examinations were performed for up to 7 months after the dosing, using a slit lamp biomicroscope and an indirect ophthalmoscope, to evaluate ocular surface morphology, anterior segment and posterior segment inflammation, cataract formation, and retinal changes. A retinal lens was used to examine the location, morphology and distribution of the microspheres in vitreous. Histological analysis was also performed on enucleated and fixed eyes for up to 7 months. At pre-determined time points for up to 7 months, the drug levels of sunitinib (ng/g) in various ocular tissues (e.g. vitreous, retina, and RPE/choroid) and plasma were also analyzed. FIG. 11A illustrates a representative 1-month histology image following injection with surface treated microparticles (STMP) and FIG. 11B illustrates a representative 1-month histology images following injection with non-surface treated microparticles (NSTMP).

TABLE 9

Detailed information on rabbit study groups and dosing conditions

| Microsphere Type | | Group # | Microsphere Mass | *SM Dose | Microsphere Drug Loading | Injection Volume |
|---|---|---|---|---|---|---|
| With surface treatment | Drug-loaded | #1 | 2 mg | 0.2 mg | 10% | 10 uL |
| | | #2 | 10 mg | 1.0 mg | 10% | 50 uL |
| | | #3 | 10 mg | 0.2 mg | 2% | 50 uL |
| | Empty | #7 | 2 and 10 mg | None | None | 10 uL (Left eye) 50 uL (Right eye) |
| Without surface treatment | Drug-loaded | #4 | 2 mg | 0.2 mg | 10% | 10 uL |
| | | #5 | 10 mg | 1.0 mg | 10% | 50 uL |
| | | #6 | 10 mg | 0.2 mg | 2% | 50 uL |
| | Empty | #8 | 2 and 10 mg | None | None | 10 uL (Left eye) 50 uL (Right eye) |

*SM = Sunitinib Malate Dose

Immediately following dosing, the microspheres remained localized at the site of injection in the vitreous as a depot for all the injections. At 1 and 2 months, fundus examination using a retina lens showed that in the eyes injected with STMP, most particle injections remained consolidated in the vitreous without dispersion and no vision impairment or disturbance was observed. In contrast, particle dispersion was more commonly observed in the eyes injected with NSTMP.

Histological analysis for up to 7 months showed that overall the injections were well tolerated with minimal evidence of ocular inflammation or toxicity. No evidence of retinal toxicity (thinning and degeneration, etc.) was observed with any treatment. With STMP, the only eyes with observed inflammation were those with injection-related lens trauma/cataract and associated secondary lens-induced uveitis, which is believed to be associated with the injection procedure and not the STMP; no other evidence of inflammation in eyes dosed with surface treated microspheres was observed (FIG. 11, left). In some of the eyes dosed with NSTMP, very mild, but present, inflammation in the vitreous that may be associated with the NSTMP was observed (FIG. 11, right). The results suggest that surface treatment not only reduces the chance of particle dispersion in the vitreous that can cause visual impairment or disturbance, but it may also reduce potential intraocular inflammation associated with microspheres and improve the overall safety of the treatment.

Figure 14:
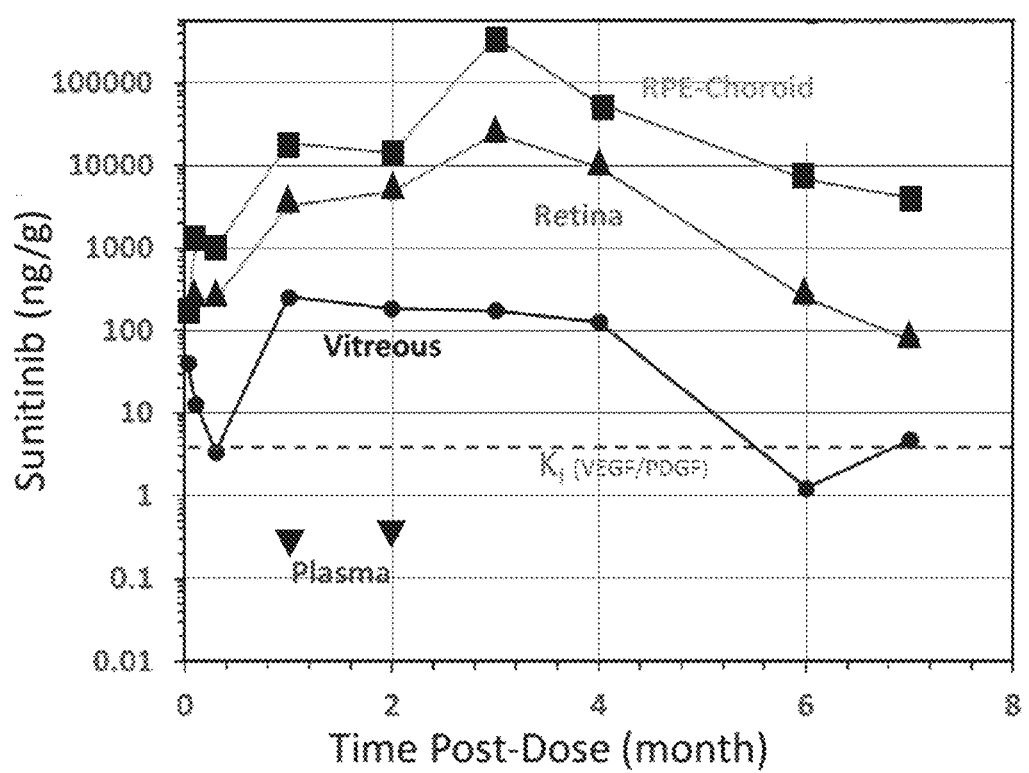
FIG. 14 illustrates subitinib levels (ng/g) in rabbits injected with 10 mg of STMP containing 1 mg sunitinib for 7 months post-dose. The rabbits were sacrificed at 4 months and sunitinib levels (ng/g) were determined in the vitreous, retina, plasma, and RPE-Choroid. Sunitinib levels were above the Ki for sunitinib against VEGFR and PDGFR (Example 20). The x-axis represents time post-dose in month and the y-axis represents the concentration of sunitinib measured in ng/g.
Figure 15:
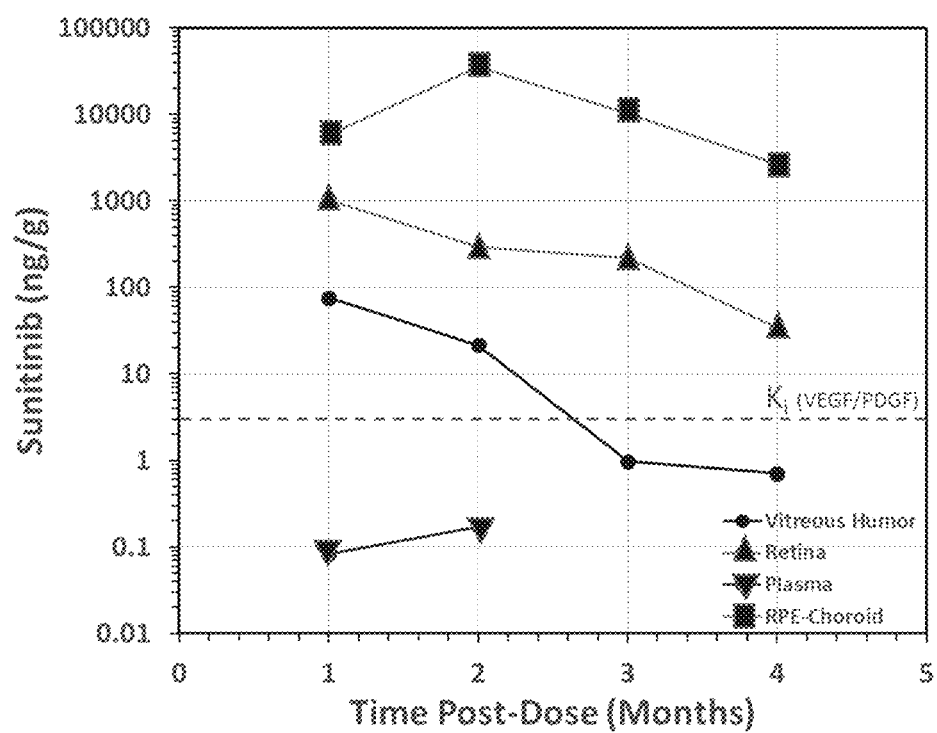
FIG. 15 illustrates sunitinib levels (ng/g) in rabbits injected with 2 mg of STMP containing 0.2 mg sunitinib (10% w/w STMP) for 4 months post-dose. The rabbits were sacrificed at 4 months and sunitinib levels (ng/g) were determined in the vitreous, retina, plasma, and RPE-Choroid. Sunitinib levels were above the Ki for sunitinib against VEGFR and PDGFR in the RPE-Choroid and retina (Example 20). The x-axis represents time post-dose in months and the y-axis represents the concentration of sunitinib measured in ng/g.
Figure 16:
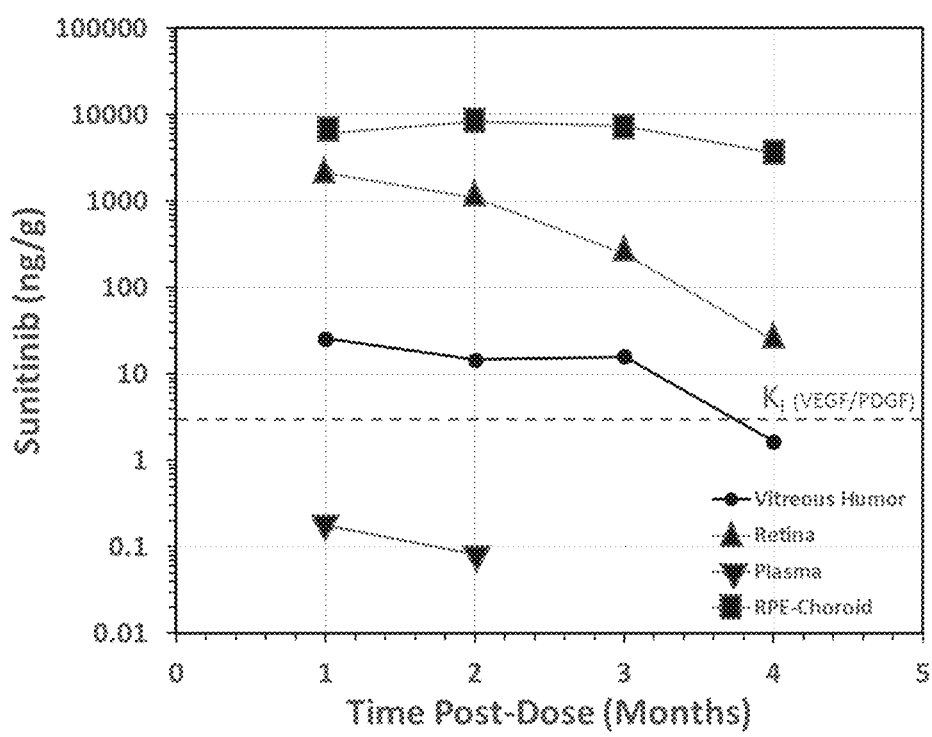
FIG. 16 illustrates sunitinib levels (ng/g) in rabbits injected with 10 mg of STMP containing 0.2 mg sunitinib (2% w/w STMP). The rabbits were sacrificed at 4 months and sunitinib levels (ng/g) were determined in the vitreous, retina, plasma, and RPE-Choroid. Sunitinib levels were above the Ki for sunitinib against VEGFR and PDGFR in the RPE-Choroid and retina (Example 20). The x-axis represents time post-dose in month and the y-axis represents the concentration of sunitinib measured in ng/g.

As shown in FIGS. 14, 15, and 16, the sunitinib levels in the retina or RPE/choroid of rabbits receiving STMP containing 1 or 0.2 mg of sunitinib malate were above the Ki for sunitinib against VEGFR and PDGFR at 1, 2, and 4 months, respectively. Low levels of sunitinib were detected in plasma only at 1 and 2 months.

Example 21. Determination of Drug Purity and Impurities in Particles

Sample S-12 (10.5 mg) was measured into an amber vial. N,N-dimethylacetamide (0.3 mL) and acetonitrile (0.6 mL) were added to dissolve the particles. Water (2.1 mL) was added and the mixture was thoroughly mixed. The final concentration of particles in N,N-dimethylacetamide/acetonitrile/water (v/v 1:2:7) mixture was 3.5 mg/mL. The purity of active compound in STMP S-12 was determined by HPLC and is reported in Table 10. The results suggest that the surface treatment did not affect the purity of encapsulated drug.

TABLE 10

HPLC analysis of drug purity in STMP

| Peak Number | Retention time | Area (%) |
|---|---|---|
| 1 | 0.24 | 0.157 |
| 2 | 0.78 | 0.283 |
| 3 | 0.82 | 0.044 |
| 4 | 1.00 | 99.39 |
| 5 | 1.12 | 0.046 |
| 6 | 1.41 | 0.084 |

Example 22. Measurement of Average Size and Size Distribution of Surface Treated Microparticles (STMP)

Figure 12:
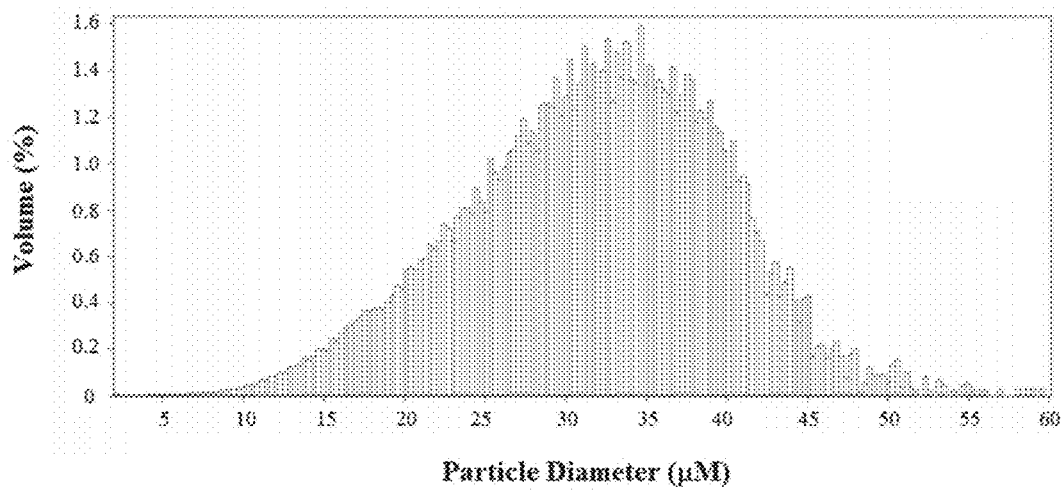
FIG. 12 illustrates the size distribution of a representative batch of surface treated microparticles (STMP) (S-12) (Example 22). The x-axis represents particle diameter measured in micrometers and the y-axis represents volume percent.

Several milligrams of S-12 were suspended in water. The mean particle size and distributions were determined using a Coulter Multisizer IV (Beckman Coulter, Inc., Brea, Calif.). The distribution shown in FIG. 12 has the following statistics: D10 of 20.98 µm, D50 of 32.32 µm, D90 of 41.50 µm, mean of 31.84 µm, and standard deviation of 8.07 µm.

Example 23. Determination of Endotoxin Level in Particle Suspension

Microparticles (5-10 mg, S-12) were added to a sterile vial in a biosafety cabinet. The particles were suspended in endotoxin-free PBS. Using a ToxinSensor™ chromogenic LAL endotoxin assay kit (GenScript USA Inc., Piscataway, N.J.) and the instructions provided by the manufacture, the sample's total level of endotoxin was measured. S-12 had a low endotoxin level of less than 10 EU/mg.

Example 24. Toxicity Studies

An acute, non-GLP IVT study was conducted to evaluate the ocular tolerability and toxicity of sunitinib malate (free drug) for up to 7 days following a single IVT injection. Sunitinib malate was formulated in phosphate buffered saline and injected bilaterally (0.1 mL) at 0.125 or 1.25 mg per eye. At the 1.25 mg/eye dose, histologically significant findings related to sunitinib included residual test article, lenticular vacuoles/degeneration, mild to minimal inflammatory cell infiltration in vitreous, retinal degeneration, detachment, and necrosis. No toxicologically significant findings were observed at the 0.125 mg/eye dose, which is considered the no-observed-adverse-effect-level (NOAEL) dose.

Figure 13A:
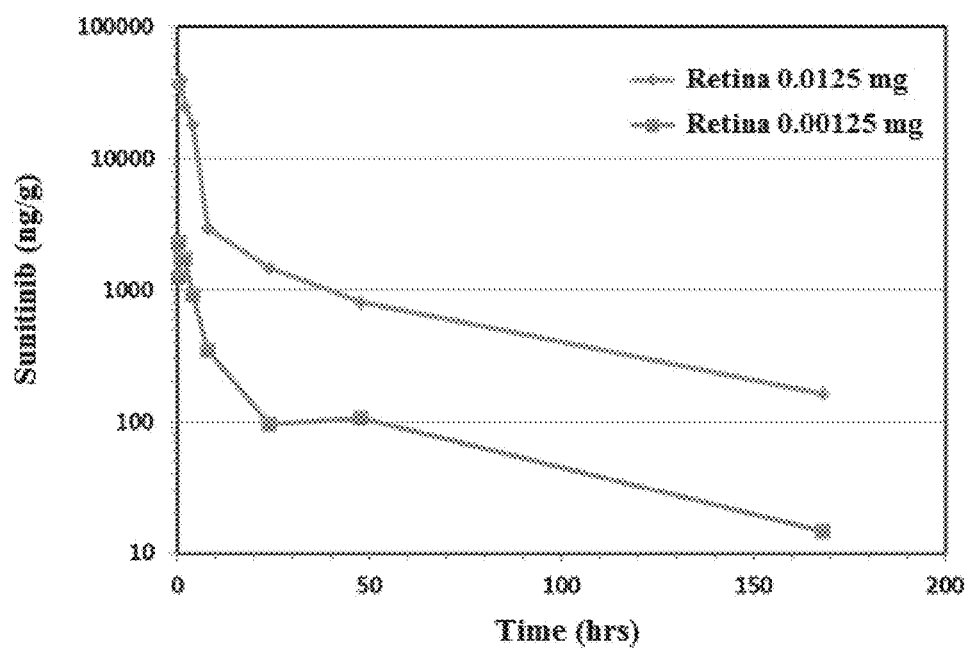
FIG. 13A illustrates select PK profiles for sunitinib in the retina following a bilateral injection of sunitinib malate (free drug) at a dose of 0.0125 mg/eye or 0.00125 mg/eye in pigmented rabbits (Example 24). The x-axis is time measured in hours and the y-axis is the concentration of sunitinib in ng/g.
Figure 13B:
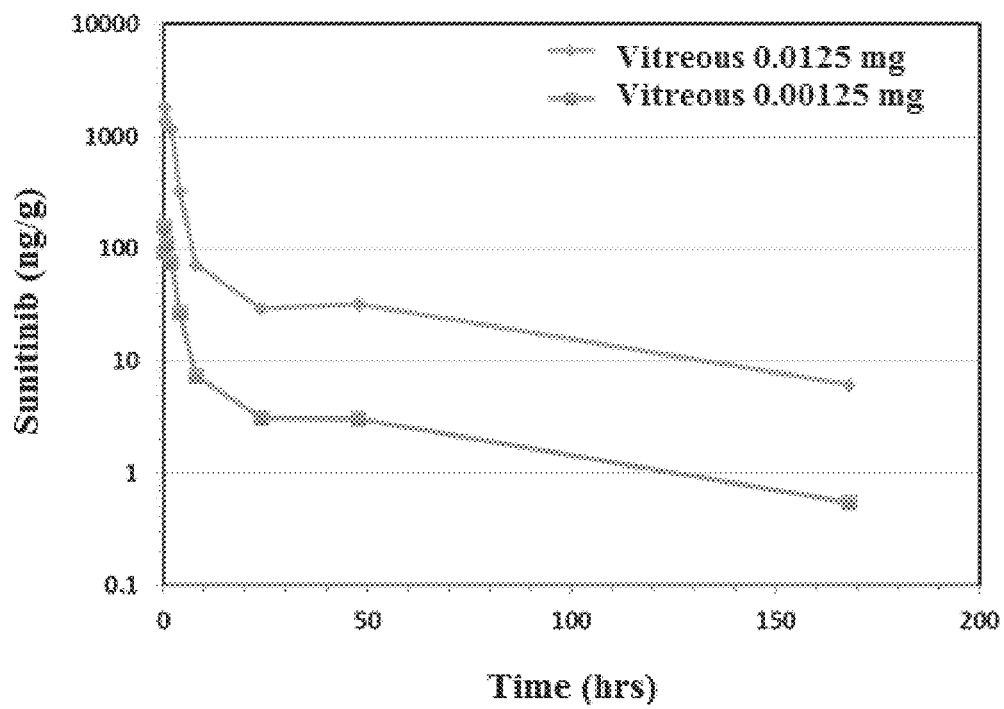
FIG. 13B illustrates select PK profiles for sunitinib in the vitreous following a bilateral injection of sunitinib malate (free drug) at a dose of 0.0125 mg/eye or 0.00125 mg/eye in pigmented rabbits (Example 24). The x-axis is time measured in hours and the y-axis is the concentration of sunitinib in ng/g.
Figure 13C:
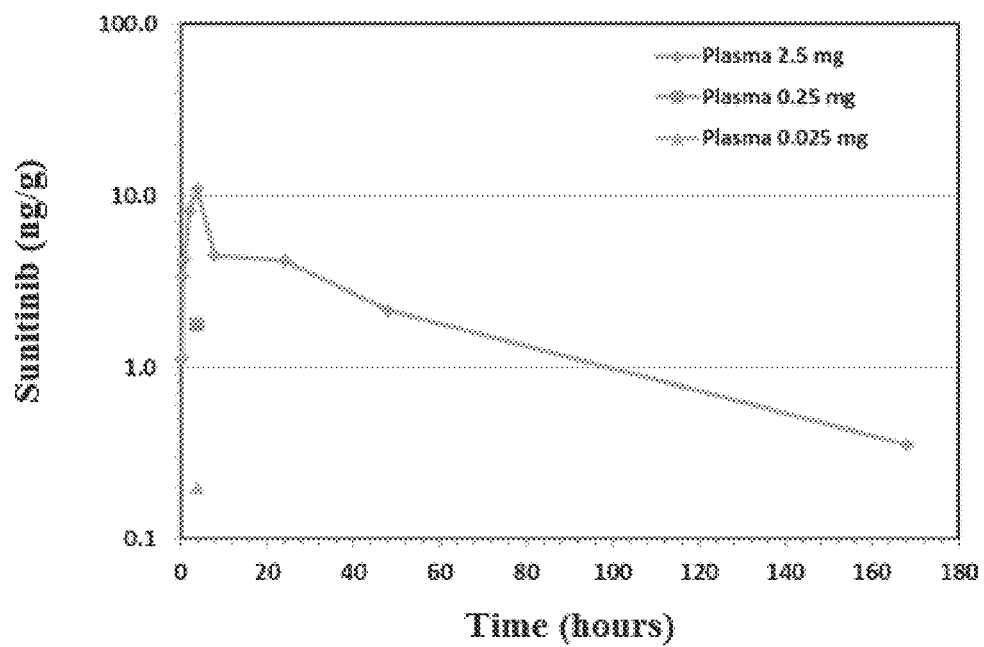
FIG. 13C illustrates select PK profiles for sunitinib in the plasma following a bilateral injection of sunitinib malate (free drug) at a dose of 2.5 mg/eye, 0.25 mg/eye, or 0.025 mg/eye in pigmented rabbits (Example 24). The x-axis is time measured in hours and the y-axis is the concentration of sunitinib in ng/g.

FIG. 13A, FIG. 13B, and FIG. 13C illustrate select PK profiles for sunitinib malate in the retina, vitreous, and plasma, respectively, from pigmented rabbits.

Example 25. Preparation of Sunitinib Microparticles (not Surface Treated)

PLGA (555 mg) and PLGA-PEG5K (5.6 mg) were dissolved in DCM (4 mL). Sunitinib malate (90 mg) was dissolved in DMSO (2 mL). The polymer and drug solutions were then mixed. The resulting reaction mixture was filtered through a 0.22 µm PTFE syringe filter. The resulting reaction mixture was diluted with 1% PVA in PBS (200 mL) in a 250 mL beaker and then homogenized at 5,000 rpm for 1 minute. (The polymer/drug solution was poured into the aqueous phase using homogenization conditions and homogenized at 5,000 rpm for 1 minute) The reaction was next stirred at 800 rpm at room temperature for 3 hours in a biosafety cabinet. The particles were allowed to settle in the beaker for 30 minutes and approximately 150 mL of the supernatant was decanted off. The microparticle suspension underwent centrifugation at 56×g for 4.5 minutes, the solvent was removed, and the microparticles were then washed three times with water. The microparticle size and size distribution was determined using a Coulter Multisizer IV prior to lyophilization. The microparticles were lyophilized using a FreeZone 4.5 liter benchtop lyophilizer. Light exposure was avoided throughout the entire process.

Example 26. General Procedure for the Preparation of Surface Treated Sunitinib Microparticles Microparticle dry powder was weighed and placed in a small beaker and a stirring bar was added. The beaker was placed in an ice bath and cooled to about 4° C. A NaOH/EtOH solution was prepared by mixing NaOH in water (0.25M) with EtOH at 3:7 (v/v) and cooling to about 4° C. The cold NaOH/EtOH solution was added with stirring to the beaker containing the microparticles to afford a particle suspension of 100 mg/mL. The suspension was stirred for 3 minutes at about 4° C. and poured into a filtration apparatus to quickly remove the NaOH/EtOH solution. (The filtration apparatus needed to be pre-chilled in a −20° C. freezer prior to use.) Following filtration, the microparticles were rinsed in the filtration apparatus with ice cold deionized water and transferred to 50 mL centrifuge tubes. Each 50 mL centrifuge tube with filled with cold water to afford a 40 mL particle suspension at a concentration of 5-10 mg/mL. The centrifuge tubes were placed in a regenerator and the particles were allowed to settle for 30 minutes. The supernatant was then decanted. The particles were resuspended in cold water and filtered through a 40 µm cell strainer to remove any large aggregates. The particles were collected by centrifugation (56×g for 4.5 minutes) and washed twice with water. The product was lyophilized using a FreeZone 4.5 liter benchtop lyophilizer. The surface treatment process was conducted at approximately 4° C. and light exposure was avoided throughout the entire process.

Example 27. Method for Determining Accelerating In Vitro Drug Release at 50° C.

Microparticles (10 mg) were added to glass scintillation vials. Four milliliters of the release medium (1% Tween 20 in 1×PBS at pH 7.4) was added into the vials and the mixtures were vortexed. The vials were shaken on an orbital shaker at 150 rpm in a Fisher general-purpose incubator at 50° C. At pre-determined time points, the appropriate vial was cooled and the particles were allowed to settle for 10 minutes. Release medium (3 mL) was then carefully removed from the top of the vial and replaced with fresh release medium (3 mL). The vial was then returned to the orbital shaker and the amount of drug in the release medium was measured by UV spectroscopy. The concentration of drug was determined by comparing to a standard curve for the drug.

Example 28. Preparation of Biodegradable Surface-Treated Microparticles (STMP) Comprising PLA NSTMP were first produced similarly as described in Example 1. Briefly, PLA and PLGA-PEG were co-dissolved in dichloromethane (DCM) and sunitinib malate was dissolved in dimethyl sulfoxide (DMSO). The polymer solution and the drug solution were mixed to form a homogeneous solution (organic phase). For empty microparticles, DMSO without drug was used. The organic phase was added to an aqueous 1% PVA solution and homogenized at 5,000 rpm for 1 minute using an L5M-A laboratory mixer (Silverson Machines Inc., East Longmeadow, Mass.) to obtain an emulsion. The emulsion (solvent-laden microparticles) was then hardened by stirring at room temperature for more than 2 hours to allow the DCM to evaporate. The microparticles were collected by sedimentation and centrifugation, washed three times in water, and filtered through a 40-μm sterile Falcon® cell strainer (Corning Inc., Corning, N.Y.). The non-surface-treated microparticles (NSTMP) were either used directly in the surface treatment process or dried by lyophilization and stored as a dry powder at −20° C. until used.

A pre-chilled solution containing NaOH and ethanol was added to microparticles in a glass vial under stirring in an ice bath at approximately 4° C. to form a suspension. The suspension was then stirred for a predetermined time on ice and poured into a pre-chilled filtration apparatus to remove the NaOH (aq)/EtOH solution. The microparticles were further rinsed with pre-chilled water and transferred to a 50-mL centrifuge tube. The STMP were then suspended in pre-chilled water and kept in a refrigerator for 30 minutes to allow the particles to settle. Following removal of the supernatant, the particles were resuspended and filtered through a 40-μm cell strainer to remove large aggregates. Subsequently, the particles were washed twice with water at room temperature and freeze-dried overnight.

TABLE 11

Detailed formulation information of STMP comprising PLA

| STMP ID | NSTMP | | | | Surface Treatment | | |
| --- | --- | --- | --- | --- | --- | --- | --- |
| | Polymer | Drug | Aqueous Phase | Mixing | Solution | Particle Conc. | Treatment Time |
| S-46 | 800 mg PLA 100 4A and 8 mg PLGA-PEG in 4 mL DCM | 100 mg sunitinib malate in 1 mL DMSO | 200 mL of 1% PVA in PBS | 5000 rpm 1 min | 0.075M NaOH and 50% EtOH | 200 mg/mL | 3 min |
| S-47 | 800 mg PLA 100 4A and 8 mg PLGA-PEG in 4 mL DCM | 1 mL DMSO | 200 mL of 1% PVA in water | 5000 rpm 1 min | 0.075M NaOH and 50% EtOH | 200 mg/mL | 3 min |
| S-48 | 640 mg PLA 100 4A and 6.4 mg PLGA-PEG in 4 mL DCM | 2 mL DMSO | 200 mL of 1% PVA in water | 5000 rpm 1 min | 0.075M NaOH and 50% EtOH | 200 mg/mL | 3 min |

The in vitro aggregability of the STMP was characterized similarly as described in Example 3. Briefly, STMP were suspended in PBS at 200 mg/mL and 30-50 uL of the suspension was injected into 1.5-2.0 mL of PBS pre-warmed at 37° C. After incubation at 37° C. for 2 hours, the aggregability of the microparticles was assessed by visual observation and/or imaging following gentle mechanical agitation. Overall all STMP described in Table 11 were able to aggregate upon incubation at 37° C. for 2 hours.

Figure 19:
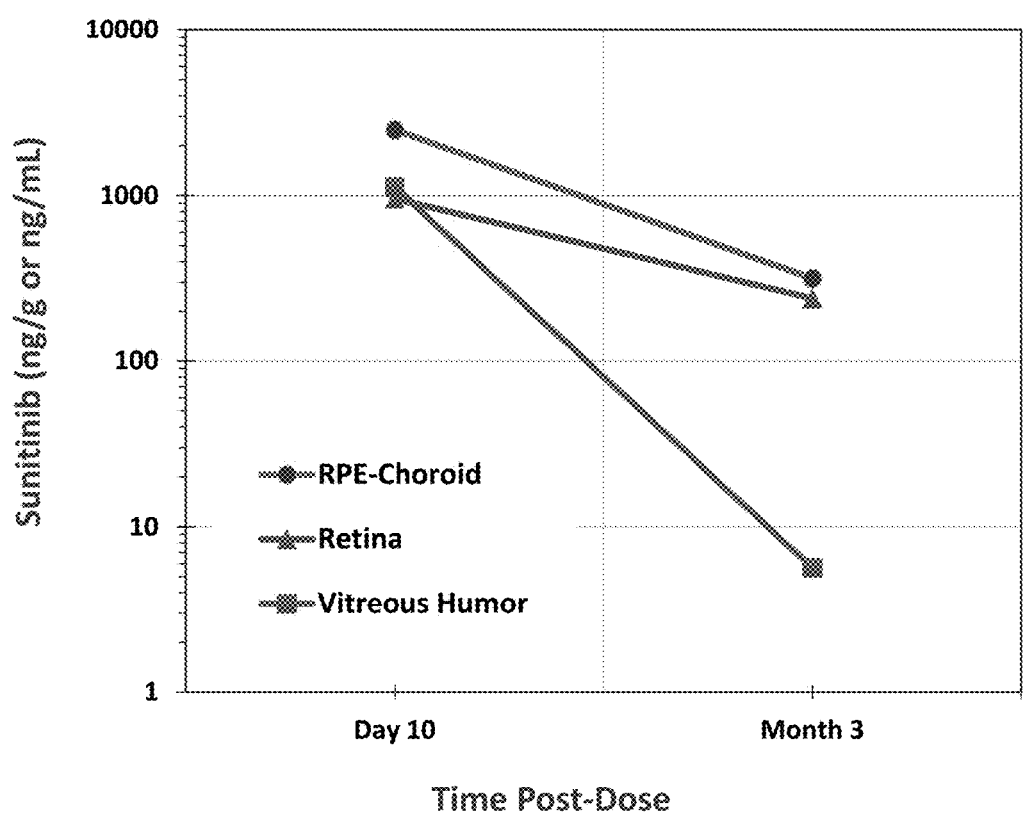
FIG. 19 is a graph depicting PK after a single IVT injection of STMP containing 1 mg sunitinib malate in rabbits. The rabbits were sacrificed at 10 days and 3 months and sunitinib levels (ng/g) were determined in the vitreous, retina, and RPE-Choroid. Sunitinib levels were above the Ki for sunitinib against VEGFR and PDGFR in the RPE-Choroid and retina (Example 29). The x-axis represents time post-dose in moths and the y-axis represents the concentration of sunitinib measured in ng/g.

Example 29. Distribution, Tolerability and Pharmacokinetics of Sunitinib-Encapsulated STMP Comprising PLA Following an Intravitreal (IVT) Injection in Rabbits Sunitinib-encapsulated STMP comprising PLA were suspended in ProVisc® diluted 5-fold in PBS to achieve a target dose of 1 mg sunitinib malate in a 50 uL particle suspension. The tolerability and pharmacokinetics were studied in pigmented New Zealand rabbits (F1) following an intravitreal injection of the STMP suspension. At pre-determined time points after the dosing, complete ocular examinations were performed and the drug levels of sunitinib (ng/g) in various ocular tissues (e.g. vitreous, retina, and RPE/choroid) were also analyzed (FIG. 19).

Ocular examinations for up to 6 months showed that the STMP were well tolerated in rabbit eyes and remained consolidated in the vitreous without dispersion and no vision impairment or disturbance was observed. As shown in FIG. 19, the sunitinib levels in retina or RPE/choroid of rabbits receiving STMP containing 1 mg of sunitinib malate were above the Ki for sunitinib against VEGFR and PDGFR at 10 days and 3 months.

Example 30. Production of Surface-Treated Microparticles (STMP) on a Larger Scale (100 g and Higher)

NSTMP were produced using a continuous flow, oil-in-water emulsification method. The scale of the pilot batches was 100-200 g. A dispersed phase (DP) and a continuous phase (CP) were first prepared. For placebo microparticles, the DP was prepared by co-dissolving PLGA and PLGA-PEG polymers in DCM. The CP was a 0.25% PVA solution in water. For drug-loaded microparticles, the DP was prepared by dissolving sunitinib malate in DMSO and mixing with the polymer solution in DCM. The CP was a 0.25% PVA solution in PBS (pH approximately 7). Detailed formulation parameters are listed in Table 12. An emulsion was produced by mixing the DP and the CP using a high shear inline mixer. The solvents in the DP were diluted by the CP, causing the emulsion droplets to solidify and become polymer microparticles. The microparticles were then washed with water using the volume exchange principle with the addition of fresh water and removal of solvent-containing water with a hollow fiber filter. The washed microparticles were subsequently suspended in a solution containing NaOH and ethanol for surface modification of the NSTMP. This step was performed in a jacketed vessel and the temperature of the suspension was maintained around 8° C. Several surface treatment conditions have been tested as shown in Table 12. Following additional washing in water and analysis of the microparticle and drug concentration of in-process samples, the STMP suspension was adjusted to target concentration prior to filling of glass vials. In some batches, mannitol was added to the final suspension. The vials were then lyophilized and sealed. The manufacturing process can be completed aseptically and the final product in vials may also be terminally sterilized by E-Beam or gamma irradiation.

The in vitro aggregability of the STMP was characterized by a similar method to that in Example 3. Briefly, STMP was suspended in PBS at 200 mg/mL and 30-50 uL of the suspension was injected into 1.5-2.0 mL of PBS pre-warmed to 37° C. After incubation at 37° C. for 2 hours, the aggregability of the microparticles was assessed by visual observation and/or imaging following gentle mechanical agitation. In general, all STMP treated with a solution containing 0.75 mM NaOH and EtOH of 40% or higher were able to aggregate upon incubation at 37° C. Following suspension in hyaluronate solution and injection in PBS, STMP treated with a higher concentration of EtOH showed a higher tendency of floatation in PBS, suggesting reduced wettability and increased surface hydrophobicity as a result of the surface treatment.

This specification has been described with reference to embodiments of the invention. However, one of ordinary skill in the art appreciates that various modifications and changes can be made without departing from the scope of the invention as set forth herein. Accordingly, the specification is to be regarded in an illustrative rather than a restrictive sense, and all such modifications are intended to be included within the scope of invention.

We claim:

1. Surface-modified solid aggregating microparticles comprising at least one biodegradable polymer, a surfactant, and a therapeutic agent that is encapsulated in the biodegradable polymer wherein the microparticles have a mean diameter between 10 μm and 60 μm that:
   (i) have a solid core with less than 10% porosity by ratio of void space to total volume;
   (ii) contain from about 0.001 percent to about 1 percent surfactant and have been surface-modified to contain less surfactant than a microparticle prior to the surface

TABLE 12

Formulation and process parameters of STMP produced on larger scale

| NSTMP | | | | | | | | | |
|---|---|---|---|---|---|---|---|---|---|
| DP | | | | | Mixing | Surface Treatment | | | |
| PLGA 7525 4A (g) | PLGA-PEG5k (g) | DCM (g) | Sunitinib Malate (g) | DMSO (g) | speed (rpm) | Time (min) | EtOH | NaOH (mM) | Excipient |
| 86 | 0.86 | 640 | 16.5 | 260 | 4000 | 30 | 30% | 0.53 | |
| 86 | 0.86 | 640 | 16.5 | 260 | 4000 | 60 | 30% | 75 | |
| 86 | 0.86 | 640 | 15.3 | 260 | 4000 | 30 | 40% | 0.075 | |
| 86 | 0.86 | 640 | 15.3 | 260 | 4000 | 30 | 40% | 0.75 | |
| 86 | 0.86 | 640 | 15.3 | 260 | 4000 | 30 | 40% | 0.75 | |
| 86 | 0.86 | 640 | 15.3 | 260 | 4000 | 30 | 40% | 0.75 | |
| 86 | 0.86 | 640 | | | 3600 | 30 | 50% | 0.75 | |
| 86 | 0.86 | 640 | | | 3600 | 30 | 40% | 0.75 | |
| 86 | 0.86 | 640 | | 260 | 3300 | 30 | 50% | 0.75 | |
| 86 | 0.86 | 640 | 15.3 | 260 | 4000 | 30 | 40% | 0.75 | |
| 86 | 0.86 | 640 | | | 3600 | 30 | 60% | 0.75 | |
| 86 | 0.86 | 640 | 15.3 | 260 | 4000 | 30 | 40% | 0.75 | |
| 86 | 0.86 | 640 | | | 3600 | 30 | 70% | 0.75 | |
| 86 | 0.86 | 640 | 15.3 | 260 | 4000 | 30 | 50% | 0.75 | Mannitol |
| 86 | 0.86 | 640 | 15.3 | 260 | 4000 | 30 | 60% | 0.75 | Mannitol |
| 86 | 0.86 | 640 | 15.3 | 260 | 4000 | 30 | 70% | 0.75 | Mannitol |
| 172 | 1.72 | 1280 | 30.6 | 520 | 4000 | 30 | 70% | 0.75 | Mannitol |
| 172 | 1.72 | 1280 | | | 3600 | 30 | 70% | 0.75 | |
| 172 | 1.72 | 1280 | | | 3600 | 25 | 70% | 0.75 | |
| 172 | 1.72 | 1280 | 30.6 | 520 | 4000 | 30 | 60% | 0.75 | Mannitol |
| 172 | 1.72 | 1280 | 30.6 | 520 | 4000 | 30 | 60% | 0.75 | Mannitol |
| 172 | 1.72 | 1280 | | | 3600 | 25 | 70% | 0.75 | Mannitol |
| 172 | 1.72 | 1280 | 30.6 | 520 | 3800 | 30 | 60% | 0.75 | Mannitol |
| 172 | 1.72 | 1280 | 30.6 | 520 | 4000 | 30 | 60% | 0.75 | |
| 172 | 1.72 | 1280 | 30.6 | 520 | 4000 | 30 | 60% | 0.75 | | modification wherein the surface has been modified at a temperature less than about 18° C.; and (iii) are capable of aggregating in vivo to form at least one pellet of at least 500 μm in vivo capable of sustained drug delivery in vivo for at least one month.

2. The surface modified solid aggregating microparticles of claim 1 suitable for injection.

3. The surface modified solid aggregating microparticles of claim 1 suitable for a delivery route selected from the group consisting of intravitreal, intrastromal, intracameral, subtenon, sub-retinal, retrobulbar, peribulbar, suprachoroidal, subchoroidal, conjunctival, subconjunctival, episcleral, posterior juxtascleral, circumcorneal, and tear duct injections.

4. The surface-modified solid aggregating microparticles of claim 1, wherein the at least one pellet is capable of sustained drug delivery for at least two months.

5. The surface-modified solid aggregating microparticles of claim 1, wherein the at least one pellet is capable of sustained drug delivery for at least three months.

6. The surface-modified solid aggregating microparticles of claim 1, wherein the at least one pellet is capable of sustained drug delivery for at least four months.

7. The surface-modified solid aggregating microparticles of claim 1, wherein the at least one pellet is capable of sustained drug delivery for at least five months.

8. The surface-modified solid aggregating microparticles of claim 1, wherein the at least one pellet is capable of sustained drug delivery for at least six months.

9. The surface-modified solid aggregating microparticles of claim 1, wherein the at least one pellet is capable of sustained drug delivery for at least seven months.

10. The surface-modified solid aggregating microparticles of claim 1, wherein the surface modification is carried out at a pH between about 6 and about 8.

11. The surface-modified solid aggregating microparticles of claim 1, wherein the surface modification is carried out at a pH between about 6.5 and about 7.5.

12. The surface-modified solid aggregating microparticles of claim 1, wherein the surface modification is carried out at a temperature of less than 16° C.

13. The surface-modified solid aggregating microparticles of claim 1, wherein the surface modification is carried out at a temperature of less than 10° C.

14. The surface-modified solid aggregating microparticles of claim 1, wherein the surface modification is carried out at a temperature of less than 8° C.

15. The surface-modified solid aggregating microparticles of claim 1, wherein the surface modification is carried out at a temperature of less than 5° C.

16. The surface-modified solid aggregating microparticles of claim 1, wherein the solid core comprises a biodegradable polymer with less than 8 percent porosity.

17. The surface-modified solid aggregating microparticles of claim 1, wherein the solid core comprises a biodegradable polymer with less than 7 percent porosity.

18. The surface-modified solid aggregating microparticles of claim 1, wherein the solid core comprises a biodegradable polymer with less than 6 percent porosity.

19. The surface-modified solid aggregating microparticles of claim 1, wherein the solid core comprises a biodegradable polymer with less than 5 percent porosity.

20. The surface-modified solid aggregating microparticles of claim 1, wherein the solid core comprises a biodegradable polymer with less than 4 percent porosity.

21. The surface-modified solid aggregating microparticles of claim 1, wherein the solid core comprises a biodegradable polymer with less than 3 percent porosity.

22. The surface-modified solid aggregating microparticles of claim 1, wherein the solid core comprises a biodegradable polymer with less than 2 percent porosity.

23. The surface-modified solid aggregating microparticles of claim 1, wherein the therapeutic agent is a pharmaceutical drug.

24. The surface-modified solid aggregating microparticles of claim 1, wherein the therapeutic agent is a biologic drug.

25. The surface-modified solid aggregating microparticles of claim 1, wherein the therapeutic agent is sunitinib, or its pharmaceutically acceptable salt.

26. The surface-modified solid aggregating microparticles of claim 1, wherein the therapeutic agent is a tyrosine kinase inhibitor.

27. The surface-modified solid aggregating microparticles of claim 1, wherein the microparticles have a mean diameter between about 20 and 30 μm.

28. The surface-modified solid aggregating microparticles of claim 1, wherein the microparticles have a mean diameter between about 20 and 50 μm.

29. The surface-modified solid aggregating microparticles of claim 1, wherein the microparticles have a mean diameter between about 25 and 35 μm.

30. The surface-modified solid aggregating microparticles of claim 1, wherein the microparticles have a mean diameter between about 20 and 40 μm.

31. The surface-modified solid aggregating microparticles of claim 1, wherein the microparticles have a mean diameter between about 25 and 40 μm.

32. The surface-modified solid aggregating microparticles of claim 1, wherein the at least one pellet has a diameter of at least 600 μm.

33. The surface-modified solid aggregating microparticles of claim 1, wherein the at least one pellet has a diameter at least 700 μm.

34. The surface-modified solid aggregating microparticles of claim 1, wherein the at least one pellet has a diameter of at least 1 mm.

35. The surface-modified solid aggregating microparticles of claim 1, wherein the at least one pellet has a diameter of at least 1.5 mm.

36. The surface-modified solid aggregating microparticles of claim 1, wherein the at least one pellet has a diameter of at least 2 mm.

37. The surface-modified solid aggregating microparticles of claim 1, wherein the at least one pellet has a diameter of at least 3 mm.

38. The surface-modified solid aggregating microparticles of claim 1, wherein the at least one pellet has a diameter of at least 4 mm.

39. The surface-modified solid aggregating microparticles of claim 1, wherein the at least one pellet has a diameter of at least 5 mm.

40. The surface-modified solid aggregating microparticles of claim 1, wherein the at least one pellet is capable of releasing not more than about 10 percent by weight of the therapeutic agent in vivo over a 24 hour period.

41. The surface-modified solid aggregating microparticles of claim 1, wherein the at least one pellet is capable of releasing not more than about 15 percent by weight of the therapeutic agent in vivo over a 24 hour period.

42. The surface-modified solid aggregating microparticles of claim 1, wherein the at least one pellet is capable of releasing not more than about 10 percent by weight of the therapeutic agent in vivo over a 12 hour period.

43. The surface-modified solid aggregating microparticles of claim 1, wherein the at least one pellet is capable of releasing not more than about 15 percent by weight of the therapeutic agent in vivo over a 12 hour period.

44. The surface-modified solid aggregating microparticles of claim 1, wherein the microparticles have a drug loading of 1-40 percent by weight.

45. The surface-modified solid aggregating microparticles of claim 1, wherein the microparticles have a drug loading of 5-25 percent by weight.

46. The surface-modified solid aggregating microparticles of claim 1, wherein the microparticles have a drug loading of 5-15 percent by weight.

47. The surface-modified solid aggregating microparticles of claim 1, wherein the microparticles have a drug loading of 0.1-5 percent by weight.

48. The surface-modified solid aggregating microparticles of claim 1, wherein the microparticles comprise poly(lactide-co-glycolide).

49. The surface-modified solid aggregating microparticles of claim 1, wherein the microparticles comprise poly(lactide-co-glycolide) covalently linked to polyethylene glycol.

50. The surface-modified solid aggregating microparticles of claim 1, wherein the microparticles comprise more than one biodegradable polymer.

51. The surface-modified solid aggregating microparticles of claim 1, wherein the microparticles comprise both poly(lactide-co-glycolide) and poly(lactide-co-glycolide) covalently linked to polyethylene glycol.

52. The surface-modified solid aggregating microparticles of claim 1, wherein the microparticles comprise poly(lactic acid).

53. The surface-modified solid aggregating microparticles of claim 1, wherein the microparticles comprise poly(lactic acid) covalently linked to polyethylene glycol.

54. The surface-modified solid aggregating microparticles of claim 1, wherein the microparticles comprise both poly(lactic acid) and poly(lactic acid) covalently linked to polyethylene glycol.

55. The surface-modified solid aggregating microparticles of claim 1, wherein the microparticles comprise both poly(lactic acid) and poly(lactide-co-glycolide) covalently linked to polyethylene glycol.

56. The surface-modified solid aggregating microparticles of claim 1 wherein the surfactant comprises polyvinyl alcohol.

57. An injectable material that comprises the microparticles of claim 1 in a pharmaceutically acceptable carrier for administration in vivo.

58. The injectable material of claim 57, further comprising a compound that inhibits aggregation of microparticles prior to injection.

59. The injectable material of claim 58 wherein the compound is a sugar.

60. The injectable material of claim 59 wherein the sugar is mannitol.

61. The injectable material of claim 57, further comprising a viscosity enhancer.

62. The injectable material of claim 61, wherein the viscosity enhancer comprises hyaluronic acid.

63. The injectable material of claim 61, wherein the viscosity enhancer comprises sodium hyaluronate.

64. The injectable material of claim 57, wherein the injectable material has a range of concentration of the surface-modified solid aggregating microparticles of about 100-600 mg/ml.

65. The injectable material of claim 57, wherein the injectable material has a range of concentration of the surface-modified solid aggregating microparticles of about 500 or less mg/ml.

66. The injectable material of claim 57, wherein the injectable material has a range of concentration of the surface-modified solid aggregating microparticles of about 300 or less mg/ml.

67. The injectable material of claim 57, wherein the injectable material has a range of concentration of the surface-modified solid aggregating microparticles of about 200 or less mg/ml.

68. The injectable material of claim 57, wherein the injectable material has a range of concentration of the surface-modified solid aggregating microparticles of about 150 or less mg/ml.

69. The surface-modified solid aggregating microparticles of claim 1, wherein the surface modification is carried out on wet microparticles.

70. The surface-modified solid aggregating microparticles of claim 1, wherein the surface treated microparticles are capable of releasing a therapeutic agent over a longer period of time compared to non-surface treated microparticles.

71. The surface-modified solid aggregating microparticles of claim 1, wherein the surface-modified solid aggregating microparticles are more hydrophobic than the microparticles prior to the surface modification.

72. The surface-modified solid aggregating microparticles of claim 1, wherein the surface-modified solid aggregating microparticles are less inflammatory than non-surface treated microparticles.

73. The surface-modified solid aggregating microparticles of claim 1, wherein the therapeutic agent is sunitinib malate.

74. The surface-modified solid aggregating microparticles of claim 73, wherein the microparticles comprise both poly(lactide-co-glycolide) and poly(lactide-co-glycolide) covalently linked to polyethylene glycol.

75. The surface-modified solid aggregating microparticles of claim 74, wherein the microparticles have a mean diameter between about 20 and 30 µm.

76. The surface-modified solid aggregating microparticles of claim 74, wherein the microparticles have a mean diameter between about 20 and 40 µm.

77. The surface-modified solid aggregating microparticles of claim 74, wherein the surfactant comprises polyvinyl alcohol.

78. The surface-modified solid aggregating microparticles of claim 1, wherein the microparticles comprise poly(lactide-co-glycolide), poly(lactic acid), and poly(lactide-co-glycolide) covalently linked to polyethylene glycol.

* * * * *